(12) United States Patent
Li et al.

(10) Patent No.: US 9,730,909 B2
(45) Date of Patent: Aug. 15, 2017

(54) METHODS FOR TARGETING CANCER STEM CELLS

(75) Inventors: Chiang Jia Li, Cambridge, MA (US); David Leggett, Milton, MA (US); Youzhi Li, Westwood, MA (US); Wei Li, Wayland, MA (US)

(73) Assignee: BOSTON BIOMEDICAL, INC, Cambridge, MA (US)

( * ) Notice: Subject to any disclaimer, the term of this patent is extended or adjusted under 35 U.S.C. 154(b) by 0 days.

(21) Appl. No.: 13/634,694

(22) PCT Filed: Mar. 21, 2011

(86) PCT No.: PCT/US2011/029283
§ 371 (c)(1),
(2), (4) Date: Oct. 16, 2012

(87) PCT Pub. No.: WO2011/116399
PCT Pub. Date: Sep. 22, 2011

(65) Prior Publication Data
US 2013/0028944 A1    Jan. 31, 2013

Related U.S. Application Data

(60) Provisional application No. 61/315,886, filed on Mar. 19, 2010, provisional application No. 61/315,890, filed on Mar. 19, 2010, provisional application No. 61/325,814, filed on Apr. 19, 2010.

(51) Int. Cl.
*A61K 31/343*   (2006.01)
*A61P 35/00*    (2006.01)
*A61K 9/14*     (2006.01)

(52) U.S. Cl.
CPC .................. *A61K 31/343* (2013.01)

(58) Field of Classification Search
CPC ..... A61K 31/343; A61K 31/27; C07D 307/92
USPC ........................... 514/468; 424/400
See application file for complete search history.

(56) References Cited

U.S. PATENT DOCUMENTS

| | | |
|---|---|---|
| 6,337,346 B1 | 1/2002 | Lee et al. |
| 6,395,773 B1 | 5/2002 | Hirai et al. |
| 6,828,337 B2 | 12/2004 | Belloni et al. |
| 7,019,147 B1 | 3/2006 | Barth et al. |
| 7,538,234 B2 | 5/2009 | Iida et al. |
| 7,910,752 B2 | 3/2011 | Tokuda et al. |
| 2004/0006009 A1 | 1/2004 | Larsen et al. |
| 2004/0092428 A1 | 5/2004 | Chen et al. |
| 2004/0138189 A1 | 7/2004 | Sebti et al. |
| 2005/0010060 A1 | 1/2005 | Blokhin et al. |
| 2005/0049207 A1 | 3/2005 | Kaufmann et al. |
| 2006/0019256 A1 | 1/2006 | Clarke et al. |
| 2006/0099251 A1 | 5/2006 | Johannsson et al. |
| 2006/0222696 A1 | 10/2006 | Okada et al. |
| 2006/0247318 A1 | 11/2006 | Song et al. |
| 2006/0252674 A1 | 11/2006 | Peritt et al. |
| 2006/0279011 A1* | 12/2006 | Palakodaty et al. ............ 264/11 |
| 2007/0060521 A1 | 3/2007 | Jove et al. |
| 2007/0238770 A1 | 10/2007 | Gougoutas et al. |
| 2009/0042977 A1 | 2/2009 | Tokuda et al. |
| 2010/0310503 A1 | 12/2010 | Li et al. |
| 2012/0252763 A1 | 10/2012 | Li et al. |

FOREIGN PATENT DOCUMENTS

| | | |
|---|---|---|
| CA | 2017806 A1 | 4/1994 |
| EP | 1134216 B1 | 9/2001 |
| EP | 1860103 B1 | 3/2006 |
| JP | 04139177 A | 5/1992 |
| JP | H11021284 A1 | 1/1999 |
| JP | 2004224802 A | 8/2004 |
| RU | 2350606 C2 | 3/2009 |
| WO | WO 9962909 A2 | 12/1999 |
| WO | WO 0044774 A2 | 8/2000 |
| WO | WO 2004026253 A3 | 4/2004 |
| WO | WO 2004/046120 A3 | 8/2004 |
| WO | WO 2005033048 A3 | 4/2005 |
| WO | WO2005058829 A1 | 6/2005 |
| WO | WO 2005110477 A2 | 11/2005 |
| WO | WO 2006056399 A2 | 6/2006 |
| WO | WO 2006091837 A2 | 8/2006 |
| WO | WO 2006098355 A1 | 9/2006 |
| WO | WO 2006113790 A2 | 10/2006 |
| WO | WO 2007100640 A2 | 9/2007 |
| WO | WO 2007115269 A2 | 10/2007 |

(Continued)

OTHER PUBLICATIONS

Haleblian J. Pharm. Sci. Aug. 1969, p. 911.*
Braatz Particle Size Control Encyclo. Pharma. Tech. 2007, p. 858.*
Ahmad, Dose transl. from animal to human, The FASEB Journal, 2007, p. 659.*
Ailles et al. "Cancer Stem Cells in Solid Tumors." *Curr. Opin. Biotechnol.* 18.5(2007):460-466.
Alvi et al. "Functional and Molecular Characterisation of Mammary Side Population Cells." *Breast Cancer Res.* 5.1(2003):R1-R8.
Baumann et al. "Exploring the Role of Cancer Stem Cells in Radioresistance." *Nat. Rev. Cancer.* 8.7(2008):545-554.

(Continued)

*Primary Examiner* — Suzanne Ziska
*Assistant Examiner* — Thurman Wheeler
(74) *Attorney, Agent, or Firm* — Boston Biomedical, Inc; Christopher D. Southgate, Esq.

(57) ABSTRACT

The invention provides naphthofuran compounds, polymorphs of naphthofuran compounds, naphthofuran compounds in particle form, purified compositions that contain one or more naphthofuran compounds, purified compositions that contain one or more naphthofuran compounds in particle form, methods of producing these naphthofuran compounds, polymorphs, purified compositions and/or particle forms, and methods of using these naphthofuran compounds, polymorphs, purified compositions and/or particle forms to treat subjects in need thereof.

37 Claims, 24 Drawing Sheets

(56) References Cited

FOREIGN PATENT DOCUMENTS

| WO | WO 2008094321 A2 | 8/2008 |
|---|---|---|
| WO | WO 2009/036099 A1 | 3/2009 |
| WO | WO-2009036101 A1 | 3/2009 |
| WO | WO 2009060282 A2 | 5/2009 |

OTHER PUBLICATIONS

Bonnet et al. "Human Acute Myeloid Leukemia is Organized as a Hierarchy That Originates From a Primitive Hematopoietic Cell." *Nat. Med.* 3.7(1997):730-737.
Bonnet. "Normal and Leukaemic Stem Cells." *Br. J. Haematol.* 130.4(2005):469-479.
Braat et al. "Crystallization: Particle Size Control." *Encyclopedia of Pharmaceutical Technology.* Swarbrick, ed. New York: Informa Healthcare. Third Edition (2007):858-871.
Collins et al. "Prospective Identification of Tumorigenic Prostate Cancer Stem Cells." *Cancer Res.* 65.23(2005):10946-10951.
Dalerba et al. "Phenotypic Characterization of Human Colorectal Cancer Stem Cells." *PNAS.* 104.24(2007):10158-10163.
Doyle et al. "Multidrug Resistance Mediated by the Breast Cancer Resistance Protein BCRP (ABCG2)." *Oncogene.* 22.47(2003):7340-7358.
Eyler et al. "Survival of the Fittest: Cancer Stem Cells in Therapeutic Resistance and Angiogenesis." *J. Clin. Oncol.* 26.17(2008):2839-2845.
Fagerholm et al. "Experimental Estimation of the Effective Unstirred Water Layer Thickness in the Human Jejunum, and its Importance in Oral Drug Absorption." *Eur. J. Pharm.* 3(1995):247-253.
Frank et al. "ABCB5-Mediated Doxorubicin Transport and Chemoresistance in Human Malignant Melanoma." *Cancer Res.* 65.10(2005):4320-4333.
Goodall et al. "Isolation and Functional Properties of Murine Hematopoietic Stem Cells That are Replicating In Vivo." *J. Exp. Med.* 183.4(1996):1797-1806.
Hambardzumyan et al. "Radiation Resistance and Stem-Like Cells in Brain Tumors." *Cancer Cells.* 10.6(2006):454-456.
Haraguchi et al. "Characterization of a Side Population of Cancer Cells From Human Gastrointestinal System." *Stem Cells.* 24.2(2006):506-513.
Hirai et al. "Furanonaphthoquinone Analogs Possessing Preferential Antitumor Activity Compared to Normal Cells." *Cancer Detect. Prev.* 23.6(1999):539-550.
Ho et al. "Side Population in Human Lung Cancer Cell Lines and Tumors is Enriched With Stem-Like Cancer Cells." *Cancer Res.* 67.10(2007):4827-4833.
Jones et al. "Cancer Stem Cells: Are We Missing the Target?" *J. Natl. Cancer Inst.* 96.8(2004):583-585.
Kondo et al. "Persistence of a Small Subpopulation of Cancer Stem-Like Cells in the C6 Glioma Cell Line." *PNAS.* 101.3(2004):781-786.
Lande et al. "The Relationship Between Membrane Fluidity and Permeabilities to Water, Solutes, Ammonia, and Protons." *J. Gen. Physiol.* 106(1995):67-84.
Li et al. "Identification of Pancreatic Cancer Stem Cells." *Cancer Res.* 67.3(2007):1030-1037.
Lipinski et al. "Experimental and Computational Approaches to Estimate Solubility and Permeability in Drug Discovery and Development Settings." *Adv. Drug Deliv. Rev.* 46.1-3(2001):3-26.
Ma et al. "Identification and Characteristic of Tumorigenic Liver Cancer Stem/Progenitor Cells." *Gastroenterology.* 132.7(2007):2542-2556.
Prince et al. "Identification of a Subpopulation of Cells With Cancer Stem Cell Properties in Head and Neck Squamous Cell Carcinoma." *PNAS.* 104.3(2007):973-978.
Rao et al. "Plant Anticancer Agents." *J. Nat. Prod.* 45.5(1982):600-604.
Ricci-Vitiani et al. "Identification and Expansion of Human Colon-Cancer-Initiating Cells." *Nature.* 445.7123(2007):111-115.
Schatton et al. "Identification of Cells Initiating Human Melanomas." *Nature.* 451.7176(2008):345-349.
Singh et al. "Identification of a Cancer Stem Cell in Human Brain Tumors." *Cancer Res.* 63.18(2003):5821-5828.
Takano et al. "Tumor-Specific Cytotoxicity and Type of Cell Death Induced by Naphtho[2,3- b]furan-4,9-diones and Related Compounds in Human Tumor Cell Lines: Relationship to Electronic Structure." *Anticancer Res.* 29.1(2009):455-464.
Wang et al. "Identification of Cancer Stem Cell-Like Side Population Cells in Human Nasopharyngeal Carcinoma Cell Line." *Cancer Res.* 67.8(2007):3716-3724.
Ministry of Health of the Russian Federation, Guidelines for the Experimental (Preclinical) Investigation of New Pharmaceutical Substances, p. 111, Moscow (2000).
Ling X et al, "Mesenchymal Stem Cells Overexpressing IFN-• Inhibit Breast Cancer Growth and Metastases through Stat3 Signaling in a Syngeneic Tumor Model," Cancer Microenviron, Mar. 19, 2010; 3 (I):83-95.
Russian Notice of Allowance issued in Russian Patent Application No. 2012144420 on Feb. 2, 2016.
Pinzon-Guzman C. et al., "Protein kinase C regulates rod photoreceptor differentiation through modulation of STAT3 signaling," Adv Exp Med Biol, 2010; 664:21-8.
STN Accession No. 1986 568912.
STN Accession No. 1992:245248.
STN Accession No. 1999:157137.
STN Accession No. 2002:33229.
Achcar Expression of activated and latent signal transducer and activator of transcription 3 in 303 non-small cell lung carcinomas and 44 malignant mesotheliomas: possible role for chemotherapeutic intervention. Arch Petal Lab Med. (2007) 131(9):1350-60.
Al-Hajj "Therapeutic implications of cancer stem cells," Cuff Opin Genet Dev, 14(1):43-7(2004).
Alvarez "Identification of a genetic signature of activated signal transducer and activator of transcription 3 in human tumors." Cancer Res. (2005) 15; 65(12):5054-62.
Amin "Selective inhibition of STAT3 induces apoptosis and G(1) cell cycle arrest in ALK-positive anaplastic large cell lymphoma." Oncogene (2004) 23,5426-5434.
Anderson "The process of structure-based drug design" Chem and Biol 10:787-797, 2003.
Aoki "Inhibition of STAT3 signaling induces apoptosis and decreases survivin expression in primary effusion lymphoma" Blood (2003) 101:1535-1542.
Arany "Correlation between pretreatment levels of interferon response genes and clinical responses to an immune response modifier (Imiquimod) in genital warts," Antimicrob Agents Chemother, 44(7):1869-73(2000).
Barton "Signal transducer and activator of transcription 3 (STAT3) activation in prostate cancer: Direct STAT3 inhibition induces apoptosis in prostate cancer lines." Mot Cancer Ther. (2004) 3(1):11-20.
Benekli "Constitutive activity of signal transducer and activator of transcription 3 protein in acute myeloid leukemia blasts is associated with short disease-free survival." Blood (2002) 99:252-257.
Benkhart "Role of Stat3 in lipopolysaccharide-induced IL-10 gene expression," J Immunol, 165(3):1612-7 (2000).
Berishaj "Stat3 is tyrosine-phosphorylated through the interleukin-6/glycoprotein 130/Janus kinase pathway in breast cancer" Breast Cancer Res. (2007) 9(3): R32.
Blaskovich "Discovery of JSI-124 (cucurbitacin I), a selective Janus kinase/signal transducer and activator of transcription 3 signaling pathway inhibitor with potent antitumor activity against human and murine cancer cells in mice" Cancer Res (2003) 63: 1270-1279.
Bleau "New Strategy for the analysis of phenotypic marker antigens in brain tumor-derived neurospheres in mice and humans," NEurosurg Focus, 24(3-4):E28(2008).
Bromberg "Stat3 as an oncogene," Cell, 98(3):295-303(1999).
Buettner, "Activated STAT signaling in human tumors provides novel molecular targets for the therapeutic intervention," Clin Cancer Res, 8(4):945-54(2002).

(56) References Cited

OTHER PUBLICATIONS

Burdelya "Stat3 activity in melanoma cells affects migration of immune effector cells and nitric oxide-mediated antitumor effects," J Immunol, 174(7):3925-31(2005).
Byrn Solid-State Chemistry of Drugs, 2d, Chapter 11 hydrates and solvates/hydrates, 233-247 (1999).
Caira, Crystalline Polymorphism of Organic Compounds, Topics in Chemistry, vol. 198 (1998).
Campbell "Cytokine-mediated inflammation, tumorigenesis, and disease associated JAKISTAT/SOCS signaling circuits in the CNS," Brain Res Brain Res Rev, 48(2):166-77(2005).
Carson "Interferon-alpha-induced activation of signal transducer and activator of transcription proteins in malignant melanoma," Clin Cancer Res, 4(9):2219-28(1998).
Catlett-Falcone "Constitutive activation of Stat3 signaling confers resistance to apoptosis in human U266 myeloma cells," Immunity, 10(1):105-15(1999).
Cesari "Inflammatory markers and onset of cardiovascular events: results from the Health ABC study," Circulation, 108(19):2317-22(2003).
Chan "Disruption of Stat3 reveals a critical role in both the initiation and the promotion stages of epithelial carcinogenesis" J. Clin. Invest. (2004) 114: 720-728.
Chang "Activation of STAT3 in thymic epithelial tumours correlates with tumour type and clinical behavior" J Pathol (2006) 210:224-33.
Chen "Signal transducer and activator of transcription 3 is involved in cell growth and survival of human rhabdomyosarcoma and osteosarcoma cells" BMC Cancer (2007) 7:111.
Chen, "Stat3 activation in human endometrial and cervical cancers," Br J Cancer, 96(4):591-9(2007).
Cho-Vega, "Suppressor of cytokine signaling 3 expression in anaplastic large cell lymphoma" Leukemia (2004) 18, 1872-1878.
Clarke "Cancer Stem Cells—Perspectives on Current Status and Future Directions: AACR Workshop on Cancer Stem Cells." Cancer Research. 66.19(2006):9339-9344.
Colman "Effect of a small molecule inhibitor of the JAK2/STAT3 pathway on self-renewal of glioblastoma stem cells." Journal of Clinical Oncology. 26.1565(2008):abstract 2003.
Corvinus "Persistent STAT3 activation in colon cancer is associated with enhanced cell proliferation and tumor growth," Neoplasia, 7(6):545-55(2005).
De Araujo "STAT3 expression in salivary gland tumours" Oral Oncology. (2007); 44(5):439-45.
Desmond, "The synthetic furanonaphthoquinone induces growth arrest, apoptosis and differentiation in a variety of leukaemias and multiple myeloma cells." British Journal of Haematology. 131.4(2005):520-529.
Diaz "Activation of stat3 in primary tumors from high-risk breast cancer patients is associated with elevated levels of activated SRC and survivin expression" Clin Cancer Research (2006) 1;12(1):20-8.
Dien et al., "Signal transducers and activators of Transcription-3 up-regulates tissue inhibitor of metalloproteinase-1 expression and decreases invasiveness of breast cancer" Am. J. Pathol. (2006) 169 (2) 633-642.
Epling-Burnette "Inhibition of STAT3 signaling leads to apoptosis of leukemic large granular lymphocytes and Decreased Mcl-1 expression," J Clin Invest, 107(3):351-62(2001).
Eyong "Semisynthesis and antitumoral activity of 2-acetylfuranonaphthoquinone and other naphthoquinone derivatives from lapachol," Bioorganic & Medicinal Chemistry Letters, 18:5387-5390 (2008).
Faloppi "The correlation between LDH serum levels and clinical outcome in advanced biliary tract cancer patients treated with first line chemotherapy." Scientific Reports 6:24136, 2016.
Fotsing "Identification of an Anti-Inflammatory Principle from the Stem Bark of Millettia versicolor", Planta Med, (2003), 69(8) 767-770.
Frank "ABCB5-mediated doxorubicin transport and chemoresistance in human malignant melanoma," Cancer Res, 65(10):4320-33 (2005).
Fu, "STAT3 in immune responses and inflammatory bowel disease," Cell Res, 16(2):214-9(2006).
Gafner "Antifungal and Antibacterial Naphthoquinones from Newbouldia laevis Roots." Phytochemistry. 42.5 (1996):1315-1320.
Gao, "Constitutive activation of JAK-STAT3 signaling by BRCA1 in human prostate cancer cells," FEBS Lett, 488 (3):179-84(2001).
Gao "Inhibition of STAT3 expression by siRNA suppresses growth and induces apoptosis in laryngeal cancer cells." Acta Pharmacol Sin. (2005) 26(3):377-83.
Gao "Knockdown of Stat3 expression using RNAi inhibits growth of laryngeal tumors in vivo" Acta Pharmacol Sin. (2006) 27(3):347-52.
Garcia "Constitutive activation of Stat3 in fibroblasts transformed by diverse oncoproteins and in breast carcinoma cells." Cell Growth Differ (1997) 8(12):1267-1276.
Garcia "Constitutive activation of Stat3 by the Src and JAK tyrosine kinases participates in growth regulation of human breast carcinoma cells" Oncogene (2001) 20(20): 2499-2513.
Nielsen, "Inhibition of constitutively activated Stat3 correlates with altered Bcl-2/Bax expression and induction of apoptosis in mycosis fungoides tumor cells" Leukemia. (1999) 13(5):735-8.
Ning, "Signal transducer and activator of transcription 3 activation is required for Asp(816) mutant c-Kit-mediated cytokine-independent survival and proliferation in human leukemia cells" Blood (2001) 97:3559-3567.
Niu, "Gene therapy with dominant-negative Stat3 suppresses growth of the murine melanoma B16 tumor in vivo" Cancer Res. (1999) 15;59(20):5059-63.
Niu, "Roles of activated Src and Stat3 signaling in melanoma tumor cell growth" Oncogene (2002) 21(46):7001-10.
Niu, "Constitutive Stat3 activity up-regulates VEGF expression and tumor angiogenesis," Oncogene, 21 (13):2000-8 (2002).
Ogawa, "Cytotoxic Activity toward KB Cells of 2-Substituted Naphtho[2,3-b]furan-4,9-diones and Their Related Compounds," Biosci. Biotechnol. Biochem., 70(4), 1009-1012, (2006).
Orshal, "Interleukin-6 impairs endothelium-dependent NO-cGMP-mediated relaxation and enhances contraction in systemic vessels of pregnant rats," Am J Physiol Regul Integr Comp Physiol, 286(6):1013-23 (2004).
Paridaens "Paclitaxel Versus Doxorubicin as First-Line Single-Agent Chemotherapy for Metastatic Breast Cancer: A European Organization for Research and Treatment of Cancer Randomized Study With Cross-Over." J. Clin. Oncol. 18.4(2000):724-733.
Pedranzini, "Stat3 is required for the development of skin cancer," J Clin Invest, 114 (5):619-22(2004).
Peraza-Sanchez "Cytotoxic Constituents of the Roots of Ekmanianthe longiflora," Journal of Natural Products, (2000), vol. 63, pp. 492-495.
Pereira et al., "Invasion-associated MMP-2 and MMP-9 are up-regulated intracellularly in concert with apoptosis linked to melanoma cell detachment," Clinical and Experimental Metastasis (2005) 22:285-295.
Ponti, "Isolation and in vitro propagation of tumorigenic breast cancer cells with stem/progenitor cell properties," Cancer Res, 65(13):5506-11(2005).
Punjabi, "Persistent activation of STAT3 by latent Kaposi's sarcoma-associated herpesvirus infection of endothelial cells," J Virol, 81(5):2449-58(2006).
Puthier, "IL-6 up-regulates mcl-1 in human myeloma cells through JAK/STAT rather than ras/MAP kinase pathway," Eur J lmmunol, 29(12):3945-50(1999).
Qiu, "RNA interference-mediated signal transducers and activators of transcription 3 gene silencing inhibits invasion and metastasis of human pancreatic cancer cells" Cancer Sci. (2007) 98(7)1099-106.
Qiuwen, "Evaluation of the potential cancer chemotherapeutic efficacy of natural product isolates employing in vivo hollow fiber tests," Journal of Natural Products, 65:842-850 (2002).
Rahaman, "Inhibition of constitutively active Stat3 suppresses proliferation and induces apoptosis in glioblastoma multiforme cells" Oncogene (2002) 21 55:8404-8413.

(56) References Cited

OTHER PUBLICATIONS

Rawat, "Constitutive activation of STAT3 is associated with the acquisition of an interleukin 6-independent phenotype by murine plasmacytomas and hybridomas" Blood. (2000) 15; 96(10):3514-21.
Roder, "STAT3 is constitutively active in some patients with Polycythemia rubra vera," Exp Hematol, 29 (6):694-702 (2001).
Rosen, "The role of constitutively active signal transducer and activator of transcription 3 in ovarian tumorigenesis and prognosis" Cancer (2006) 107(11) 2730-40.
Savarese, "Coexpression of oncostatin M and its receptors and evidence for STAT3 activation in human ovarian carcinomas," Cytokine, 17(6):324-34(2002).
Schaefer, "Constitutive activation of Stat3alpha in brain tumors: localization to tumor endothelial cells and activation by the endothelial tyrosine kinase receptor (VEGFR-2)," Oncogene, 21(13):2058-65(2002).
Scheper, "Sulindac induces apoptosis and inhibits tumor growth in vivo in head and neck squamous cell carcinoma" Neoplasia (2007) 9(3): 192-199.
Scholz, "Activated signal transducer and activator of transcription 3 (STAT3) supports the malignant phenotype of human pancreatic cancer" Gastroenterology (2003) 125:891-905.
Schlette, "Survivin expression predicts poorer prognosis in anaplastic large-cell lymphoma," J Clin Oncol, 22 (9):1682-8(2004).
Sengupta, "Activation of monocyte effector genes and STAT family transcription factors by inflammatory synovial fluid is independent of interferon gamma," J Exp Med, 181(3):1015-25(1995).
Shouda, "Induction of the cytokine signal regulator SOCS3/CIS3 as a therapeutic strategy for treating inflammatory arthritis," J Clin Invest, 108(12):1781-8(2001).
Simeone-Penney, "Airway epithelial STAT3 is required for allergic inflammation in a murine model of asthma," J Immunol, 178(10):6191-9(2007).
Silver, "Activated signal transducer and activator of transcription (STAT) 3: localization in focal adhesions and function in ovarian cancer cell motility" Cancer Res. (2004) 15;64(10):3550-8.
Solorzano "Decreased glycolytic metabolism accelerates apoptosis in response to 2-acetyl furanonaphthoquinone in K1735 melanoma irrespective of bcl-2 overexpression" Cancer Biol. Ther. (2005) vol. 4, No. 3, pp. 329-335.
Sommer, "In vivo activation of STAT3 in cutaneous T-cell lymphoma. Evidence for an antiapoptotic functions of STAT3," Leukemia, 18(7):1288-95(2004).
Song and Grandis, "STAT signaling in head and neck cancer," Oncogene, 19(21):2489-95(2000).
Song, "Activation of Stat3 by receptor tyrosine kinases and cytokines regulates survival in human non-small cell carcinoma cells," Oncogene, 22(27):4150-65(2003).
Song "A low-molecular-weight compound discovered through virtual database screening inhibits Stat3 function in breast cancer cells." Proc. Natl. Acad Sci.102.13(2005): 4700-4705.
Spiekerman, "Constitutive activation of STAT transcription factors in acute myelogenous leukemia" Eur J Haematol (2001) 67: 63-71.
Steinert "HPLC separation and determination of naphtho[2,3-b]furan-4,9-diones and related compounds in extracts of Tabebuia avellanedae (Bignoniaceae)" J Chromato A 693:281-287, 1995.
Stelmasiak, "Interleukin-6 concentration in serum and cerebrospinal fluid in multiple sclerosis patients," Med Sci Monit, 6(6)1104-8(2000).
Stephens, "A common functional variant in the interleukin-6 gene is associated with increased body mass indexin subjects with type 2 diabetes mellitus," Mol Genet Metab, 82(2)180-6(2004).
Stout (Blog entitled "No Cancer", available online at http://nocancer.blogspot.com/2005/05/14-pau-darco.html, published, 2005).
Sun "Comparison of Effects of the Tyrosine Kinase Inhibitors AG957, AG490, and STI571 on BCR-ABL-Expressing Cells, Demonstrating Synergy Between AG490 and STI571." Blood. 97.7(2001):2008-2015.
Szotek, "Ovarian cancer side population defines cells with stem cell-like characteristics and Mullerian Inhibiting Substance responsiveness," Proc Natl Acad Sci USA, 103(30):11154-9(2006).
Taylor, "Herbal Secrets of the Rainforest", 2nd Edition (2003).
Tefferi, "Classification, diagnosis and management of myeloproliferative disorders in the JAK2V617F era," Hematology Am Soc Hematol Educ Program, 240-5 (2006).
Toyonaga, "Blockade of constitutively activated Janus kinase/signal transducer and activator of transcription-3 pathway inhibits growth of human pancreatic cancer," Cancer Lett, 201(1):107-16(2003).
Trovato, "Distinctive expression of STAT3 in papillary thyroid carcinomas and subset of follicular adenomas" Histol Histopathol (2003) 18: 393-399.
Tsareva, "Signal transducer and activator of transcription 3 activation promotes invasive growth of colon carcinomas through matrix metalloproteinase induction" Neoplasia (2007) 9, 4: 279-291.
Wang Zhianghiga Bins Li Xi.* Za Zhi (V07) 36(6):3Z9-83.
Nang, "Effect of STAT3 siRNA-induced inhibition of STAT3 gene expression on the growth and apoptosis of lewis lung cancer cells" J. Clin. Oncol. (2006) 3: 392-399.
Watson, "Elevated levels of members of the STAT family of transcription factors in breast carcinoma nuclear extracts" British Journal of Cancer (1995) 71(4): 840-844.
Weber-Nordt, "Constitutive activation of STAT proteins in primary lymphoid and myeloid leukemia cells and in Epstein-Barr virus (EBV)-related lymphoma cell lines," Blood, 88(3):809-16(1996).
Gormann "Furanonaphthoquinones, atraric acid and a benzofuran from the stem barks of Newbouldia laevis" Phytochemistry. 64.2(2003):583-587.
Grandis "STAT signaling in head and neck cancer" Oncogene (2000) 15;19(21): 2489-95.
Gritsko "Persistent activation of stat3 signaling induces survivin gene expression and confers resistance to apoptosis in human breast cancer cells" Clinical Cancer Research (2006) 12(1): 11-19.
Han Li., "Unusual naphthoquinone derivatives from the twigs of Avicennia marina" J. Nat. Prod. (2007) 70, 923-927.
Harris "Cutting edge: An in vivo requirements for STAT3 signaling in TH17 development and TH17-dependent autoimmunity," J Immunol, 179(7):4313-7(2007).
Haura "Activated epidermal growth factor receptor-Stat-3 signaling promotes tumor survival in vivo in non-small cell lung cancer" Clin Cancer Res (2005) 11(23) 8288-94.
Holtick "STAT3 is essential for Hodgkin lymphoma cell proliferation and is a target of tyrphostin AG17 which confers sensitization for apoptosis" Leukemia. (2005) 19 (6):936-44.
Horiguchi "Activation of signal transducer and activator of transcription 3 in renal cell carcinoma: a study of incidence and its association with pathological features and clinical outcome" The Journal of Urology (2002) 168 (2):762-765.
Hsiao "Constitutive activation of STAT3 and STAT5 is present in the majority of nasopharyngeal carcinoma and correlates with better prognosis." Br J Cancer. (2003) 21;89 (4344-9).
Huang "Constitutive activation of stat 3 oncogene product in human ovarian carcinoma cells" Gynecol Oncol. (2000) 79(1):67-73.
Ishihara "IL-6 in autoimmune disease and chronic inflammatory proliferative disease," Cytokine Growth Factor Rev, 13(4-5):357-68(2002).
Itoh "Requirement of STAT3 activation for maximal collagenase-1 (MMP-1) induction by epidermal growth factor and malignant characteristics in T24 bladder cancer cells." Oncogene (2006) 25, 1195-1204.
Itoigawa "Cancer chemopreventive activity of naphthoquinones and their analogs from Avicennia plants." Cancer Letters. 174. 2(2001):135-139.
Iwamaru "A novel inhibitor of the STAT3 pathway induces apoptosis in malignant glioma cells both in vitro and in vivo" Oncogene (2006) 26, 2435-2444.
Ivashkiv "Can SOCS make arthritis better?", J Clin Invest, 111(6):795-7(2003).

(56) References Cited

OTHER PUBLICATIONS

Johnson "Abrogation of Signal Transducer and Activator of Transcription 3 Reactivation After Src Kinase Inhibition Results in Synergistic Antitumor Effects." Clin. Cancer Res. 13.14(2007):4233-4244.
Johnston "STAT3 Signaling: Anticancer Strategies and Challenges." MoL Intent. 11.1(2011)18-26.
Kanda "STAT3 is constitutively activated and supports cell survival in association with survivin expression in gastric cancer cells," Oncogene, 23(28):4921-9,(2004).
Kang, "A new route to naphtho[2,3-b]furan-4,9-diones from thiosubstituted 1,4-naphthoquinones," Journal of the Chemical Society. Perkin transactions 1, 1990(3):441-445.
Kijima "STAT3 activation abrogates growth factor dependence and contributes to head and neck squamous cell carcinoma tumor growth in vivo" Cell Growth Diff. (2002) 13: 355-362.
Katoh. "STAT3-induced WNT5A signaling loop in embryonic stem cells, adult normal tissues, chronic persistent inflammation, rheumatoid arthritis and cancer (Review)." International Journal of Molecular Medicine. 19.2 (2007):273-278.
Kim "Inhibition of signal transducer and activator of transcription 3 activity results in down-regulation of Survivin following irradiation" Mol. Cancer Thera. 5.11(2006):2659-2665.
Kim, "JAK-STAT signaling mediates gangliosides-induced inflammatory responses in brain microglial cells," J Biol Chem, 277(43):40594-601(2002).
Konnikova, "Knockdown of STAT3 expression by RNAi induces apoptosis in astrocytoma cells" BMC Cancer (2003) 3:23.
Koyanagi "A Facile Synthesis of 2-Acteylnaphtho[2,3-b]furan-4,9-dione," Journal of Heterocyclic Chemistry, (1995), vol. 32, pp. 1289-1291.
Koyanagi "A New Synthetic of 2-Substituted Naphtho[2,3-b]furan-4,9-dione," Journal of Heterocyclic Chemistry, (1997), vol. 34, pp. 407-412.
Koyoma "Micellar electrokinetic chromatography (MEKC) separation of furanophthoquinones from Tabeuia impetiginosa" Chem. Pharm. Bull. (Tokyo), 2000, 48(6) 873-875.
Krause "Rheumatoid arthritis synoviocyte survival is dependent on Stat3," J Immunol, 169(11):6610-6(2002).
Kusaba, "Expression of p-STAT3 in human colorectal adenocarcinoma and adenoma; correlation with clinicopathological factors" Journal of Clinical Pathology (2005) 58(8) 833-838.
Lai, "Signal transducer and activator of transcription-3 activation contributes to high tissue inhibitor of metalloproteinase-1 expression in anaplastic lymphoma kinase-positive anaplastic large cell lymphoma," Am J Pathol, 164(6)2251-8(2004).
Lai, "STAT3 is activated in a subset of the Ewing sarcoma family of tumours," J Pathol, 208(5):624-32(2006).
Lassmann, "STAT3 mRNA and protein expression in colorectal cancer: effects on STAT3-inducible targets linked to cell survival and proliferation" J Clin Pathol. (2007);60(2):173-9.
Lau, "Inhibition of Stat3 activity by YC-1 enhances chemo-sensitivity in hepatocellular carcinoma" Cancer Blot Ther. (2007) 6(12):1900-7.
Lee "Efficient Synthesis of Cytotoxic Furonaphthoquinone Natural Products," Synthetic Communications, 31(3), 381-386 (2001).
Leong, "Targeted inhibition of Stat3 with a decoy oligonucleotide abrogates head and neck cancer cell growth" Proc Nati Aced Sci USA (2003) 1;100(7): 4138-43.
Li, "Autocrine-mediated activation of STAT3 correlates with cell proliferation in breast carcinoma lines" J. Biol. Chem. (2002) 277, 17397-17405.
Li, "Inhibition of growth and metastasis of human hepatocellular carcinoma by antisense oligonucleotide targeting signal transducer and activator of transcription 3" Clin Cancer Res. (2006) 1;12(23):7140-8.
Libby, "Inflammation and atherosclerosis," Circulation, 105(9):1135-43(2002).
Lim, "Stat3 contributes to keloid pathogenesis via promoting collagen production, cell proliferation and migration," Oncogene, 25(39):5416-25(2006).
Lin, "Constitutive activation of JAK3/STAT3 in colon carcinoma tumors and cell lines: inhibition of JAK3/STAT3 signaling induces apoptosis and cell cycle arrest of colon carcinoma cells" Am J Pathol (2005) 167:969-980.
Lin, "Significance of the expression of phosphorylated signal transducer and activator of transcription-3-Akt, and cyclin D1 in angiosarcoma" J. Derm. Soi. (2007) 48(1) 64-66 Lin, J. Derm. Sci. (2007) 48(1) 71-73.
Liu, "Expression and clinical significance of COX-2, p-Stat3, and p-Stat5 in esophageal carcinoma." Ai Zheng (2007) 26(6):468 62.
Lopes "Efficient Synthesis of Cytotoxic Quinones: 2-Acteyl-4H,9H-naphtho[2,3-b]furan-4,9-dione (6) and (±)-2-(1-Hydroxyethyl)-4H,9H-naphtho[2,3-b]furan-4,9-dione (7)," Journal of Heterocyclic Chemistry, (1984), vol. 21, pp. 621-622.
Lovato, "Constitutive STAT3 activation in intestinal T cells from patients with Crohn's disease," J Biol Chem, 278 (19):16777-81(2003).
Ma, "Constitutive activation of Stat3 signaling pathway in human colorectal carcinoma" World J Gastroent. (2004) 10(11): 1569-1573.
Manolagas, "Role of cytokines in bone resorption," Bone, 17(2 Suppl):63S-67S(1995).
Masuda, Constitutive activation of signal transducers and activators of transcription 3 correlates with cyclin D1 overexpression and may provide a novel prognostic marker in head and neck squamous cell carcinoma Cancer Res. (2002) 62: 3351-3355.
Mizoguchi, "Activation of STAT3, MAPK, and AKT in malignant astrocytic gliomas: correlation with EGFR status, tumor grade, and survival" Journal of Neuropathology and Experimental Neurology (2006) 65(12)1181-1188.
Mora, "Constitutive activation of Stat3 in human prostate tumors and cell lines: direct inhibition of Stat3 signaling induces apoptosis of prostate cancer cells" Cancer Res (2002) 62(22): 6659-6666.
Morrissett "High-throughput crystallization: polymorphs, salts, co-crystals and solvates of pharmaceutical solids" Adv. Drug Delivery Rev. 2004, 56, 275-300.
Wermuth "Molecular Variations Based on Isoteric Replacements," The Practice of Medicinal Chemistry, Academic Press, 1996. pp. 203-237.
Williams "Two New Cytotoxic Naphthoquinones from Mendoncia cowanii from the Rainforest of Madagascar." Planta Medica. 72.6(2006):564-566.
Xie, "Stat3 activation regulates the expression of matrix metalloproteinase-2 and tumor invasion and metastasis," Oncogene, 23(20):3550-60(2004).
Yao, "Experimental study on the growth inhibition of bladder cancer cells by signal conduction blocker AG490." Journal of Clinical Urology. 21.5 (2006):379-382.
Yau "Inhibition of Integrin-Linked Kinase by QLT0254 Inhibits Akt-Dependent Pathways and is Growth Inhibitory in Orthotopic Primary Pancreatic Cancer Xenografts." Cancer Res. 65A(2005):1497-1504.
Zani "Furanonaphthoquinones from Tabebuia Ochracea," Phytochemistry, (1991), vol. 30, No. 7, pp. 2379-2381.
Zhang, "Intratumoral delivery and suppression of prostate tumor growth by attenuated *Salmonella enterica* serovar typhimurium carrying plasmid-based small interfering RNAs," Cancer Res, 67(12):5859-64(2007).
Zhou, "Activation of the PTEN/mTOR/STAT3 pathway in breast cancer stem-like cells is required for viability and maintenance." PNAS. 104.41(2007):16158-16163.
Zhou, "Corrections: Activation of the PTEN/mTOR/STAT3 pathway in breast cancer stem-like cells is required for viability and maintenance." PNAS. 104.49(2007):19655-19656.

\* cited by examiner

Process Flow Diagram

Step 1: Synthesis of 3,4-Dibromobutene-2-one

Step 2: De-bromination of 3-Bromobutene-2-one

Step 3: Synthesis of Compound 1

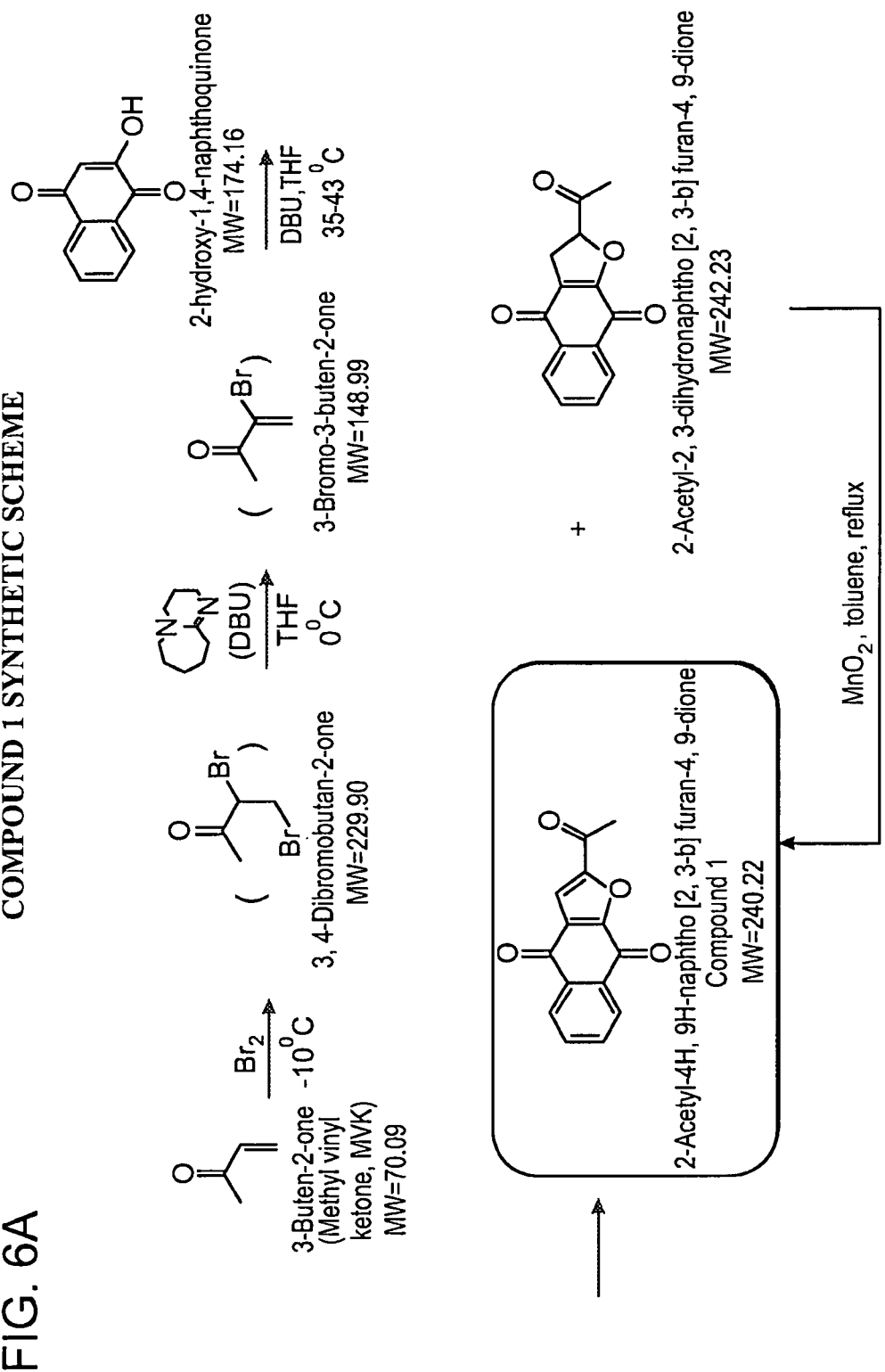
FIG. 6A COMPOUND 1 SYNTHETIC SCHEME

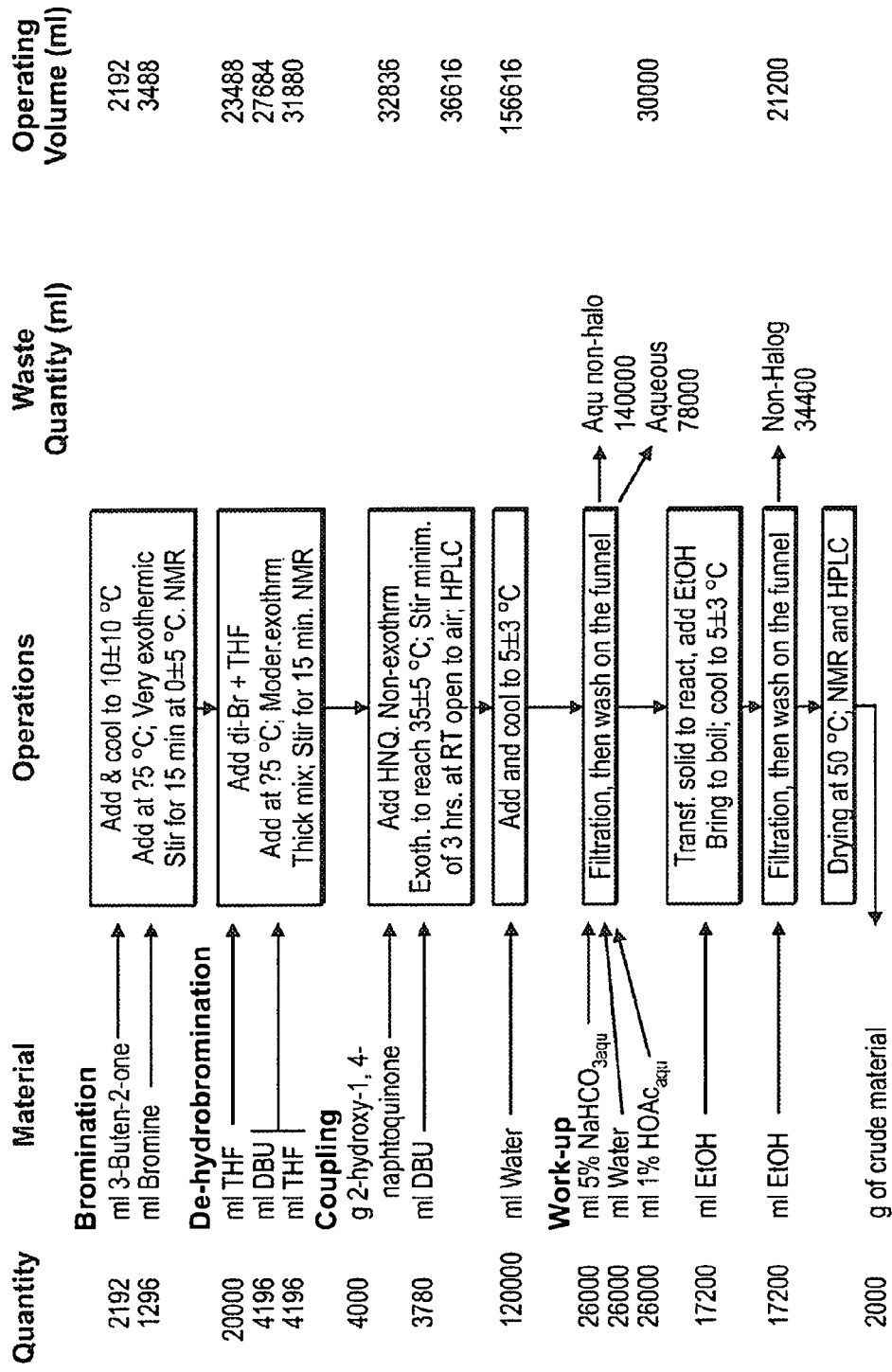
FIG. 6B Process Flow Diagram: Step 1: Synthesis of crude Compound 1

Compound 1 Median PFS = 13 weeks
BSC Median PFS = 8 weeks
Hazard Ratio for PFS=0.362 95% CI, 0.146 to 0.9183; P=0.013

METHODS FOR TARGETING CANCER STEM CELLS

RELATED APPLICATIONS

This application is a national stage application, filed under 35 U.S.C. §371, of International Application No. PCT/US2011/029283, filed Mar. 21, 2011, which claims the benefit of U.S. Provisional Application No. 61/315,886, filed Mar. 19, 2010; U.S. Provisional Application No. 61/315,890, filed Mar. 19, 2010 and U.S. Provisional Application No. 61/325,814, filed Apr. 19, 2010. The contents of each of these applications are hereby incorporated by reference in their entirety.

FIELD OF THE INVENTION

The invention provides naphthofuran compounds, polymorphs of naphthofuran compounds, naphthofuran compounds in particle form, purified compositions that contain one or more naphthofuran compounds, purified compositions that contain one or more naphthofuran compounds in particle form, methods of producing these naphthofuran compounds, polymorphs, purified compositions and/or particle forms, and methods of using these naphthofuran compounds, polymorphs, purified compositions and/or particle forms to treat subjects in need thereof.

BACKGROUND OF THE INVENTION

Cancer fatalities in the United States alone number in the hundreds of thousands each year. Despite advances in the treatment of certain forms of cancer through surgery, radiotherapy, and chemotherapy, many types of cancer are essentially incurable. Even when an effective treatment is available for a particular cancer, the side effects of such treatment can be severe and result in a significant decrease in quality of life.

Most conventional chemotherapy agents have toxicity and limited efficacy, particularly for patients with advanced solid tumors. Chemotherapeutic agents cause damage to non-cancerous as well as cancerous cells. The therapeutic index of such compounds (a measure of the ability of the therapy to discriminate between cancerous and normal cells) can be quite low. Frequently, a dose of a chemotherapy drug that is effective to kill cancer cells will also kill normal cells, especially those normal cells (such as epithelial cells) which undergo frequent cell division. When normal cells are affected by the therapy, side effects such as hair loss, suppression of hematopoiesis, and nausea can occur. Depending on the general health of a patient, such side effects can preclude the administration of chemotherapy, or, at least, be extremely unpleasant and uncomfortable for the patient and severely decrease quality of the remaining life of cancer patients. Even for cancer patients who respond to chemotherapy with tumor regression, such tumor response often is not accompanied by prolongation of progression-free survival (PFS) or prolongation of overall survival (OS). As a matter of fact, cancer often quickly progress and form more metastasis after initial response to chemotherapy. Such recurrent cancers become highly resistant or refractory to chemotherapeutics. Such rapid recurrence and refractoriness, after chemotherapy, are considered to be caused by cancer stem cells.

Recent studies have uncovered the presence of cancer stem cells (CSC, also called tumor initiating cells or cancer stem-like cells) which have self-renewal capability and are considered to be fundamentally responsible for malignant growth, relapse and metastasis. Importantly, CSCs are inherently resistant to conventional therapies. Therefore, a targeted agent with activity against cancer stem cells holds a great promise for cancer patients (J Clin Oncol. 2008 Jun. 10; 26(17)). Therefore, conventional chemotherapies can kill the bulk of cancer cells, but leave behind cancer stem cells. Cancer stem cells can grow faster after reduction of non-stem regular cancer cells by chemotherapy, which is consider the mechanism for the quick relapse after chemotherapies.

STAT3 is an oncogene which is activated in response to cytokines and/or growth factors to promote proliferation, survival, and other biological processes. STAT3 is activated by phosphorylation of a critical tyrosine residue mediated by growth factor receptor tyrosine kinases, Janus kinases, or the Src family kinases. Upon tyrosine phosphorylation, STAT3 forms homo-dimers and translocates to the nucleus, binds to specific DNA-response elements in target gene promoters, and induces gene expression. STAT3 activates genes involved in tumorigenesis, invasion, and metastasis, including Bcl-xl, Akt, c-Myc, cyclin D1, VEGF, and survivin. STAT3 is aberrantly active in a wide variety of human cancers, including all the major carcinomas as well as some hematologic tumors. Persistently active STAT3 occurs in more than half of breast and lung cancers, colorectal cancers, ovarian cancers, hepatocellular carcinomas, and multiple myelomas, etc; and more than 95% of head/neck cancers. STAT3 is considered to be one of the major mechanism for drug resistance of cancer cells. However, STAT3 has proven a difficult target for discovering pharmaceutical inhibitor. So far, no direct inhibitor of STAT3 with clinically-relevant potency has been identified after decades of efforts in the industry.

Accordingly, there exists a need for discovering compounds and pharmaceutical compositions for selectively targeting cancer cells, for targeting cancer stem cells, and for inhibiting STAT3, and methods of preparing these compounds and pharmaceutical compositions for clinical applications.

The references cited herein are not admitted to be prior art to the claimed invention.

SUMMARY

The invention provides naphthofuran compounds, polymorphs of naphthofuran compounds, purified compositions that contain one or more naphthofuran compounds, and naphthofuran compounds in particle form. These naphthofuran compounds (including those in particle form), polymorphs, and purified compositions are selective inhibitors of cancer stem cells and STAT3. WO 2009/036099 and WO 2009/036101 disclose that naphthofuran compounds target cancer stem cells. It also inhibits non-stem cancer cells through inhibiting STAT3. Those compounds are capable of killing many different types of cancer cells, without causing damage to normal cells under certain exposure conditions. The compounds can therefore be used for cancer treatment, especially for the treatment and prevention of refractory, recurrent, metastatic cancers, or STAT3-expressing cancers. The publications also describe the processes for preparing naphthofuran compounds, derivatives, and intermediates thereof, and the pharmaceutical composition of relevant compounds.

These naphthofuran compounds (including those in particle form), polymorphs, and purified compositions described herein are useful in a variety of indications, including, for example, treating, delaying the progression of, preventing a relapse of, or alleviating a symptom of a cell proliferation disorder. For example, the naphthofuran compounds (including those in particle form), polymorphs, and purified compositions are useful in treating, delaying the progression of, preventing a relapse of, alleviating a symptom of, or otherwise ameliorating a cancer.

In some embodiments, the naphthofuran compound is a polymorph of the compound shown below, referred to herein as "Compound 1,"

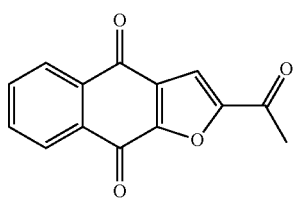

(1)

For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. X-ray powder diffraction analysis shown in FIG. 1 was performed using a Philips PW1800 diffractometer using Cu radiation at 40 KV/30 mA over the range of 5° to 70° with a step size of 0.03° and a counting time of 3 hours. Analysis was performed from 2-45° 2-theta using the following conditions: divergence slit: 0.6 mm, anti-scatter slit: 0.6 mm, receiving slit: 0.1 mm, detector slit: 0.6 mm, step size: 0.02°, step time: 5 seconds. In some embodiments, the polymorph is a polymorph of 2-acetyl-4H, 9H-naphtho[2,3-b]furan-4,9-dione characterized by an X-ray diffraction pattern substantially similar to that set forth in FIG. 2. In some embodiments, the polymorph is a polymorph of 2-acetyl-4H, 9H-naphtho[2,3-b]furan-4,9-dione characterized by an X-ray diffraction pattern substantially similar to that set forth in FIG. 3. X-ray powder diffraction analysis shown in FIGS. 2 and 3 was performed using a Bruker D8 Advance diffractometer. Analysis was performed from 2-45° 2-theta using the following conditions: divergence slit: 0.6 mm, anti-scatter slit: 0.6 mm, receiving slit: 0.1 mm, detector slit: 0.6 mm, step size: 0.02°, step time: 5 seconds.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

The present invention also provides naphthofuran compounds in particle form. For example, the naphthofuran compound in particle form is a particle of a compound of Formula I shown below, which is active, i.e., has an efficacy and/or an antitumor activity in vivo. The efficacious particle or particles have a defined requirement for particle size, for example, has a diameter of less than or equal to about 200 μm, about 150 μm, about 100 μm, about 40 μm, or about 20 μm, about 10 μm, about 5 μm, about 4 μm, about 3 μm, about 2 μm, about 1 μm, about 0.5 μm, or about 0.2 μm. The particle or particles that are larger than the defined particle size are either inactive or less active.

In some embodiments, the naphthofuran compound in particle form is a particle of a compound according to Formula I or a salt or solvate thereof,

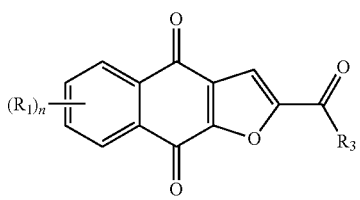

Formula I wherein the particle has a diameter of less than or equal to about 200 μm; wherein each ($R_1$) is independently selected from the group consisting of hydrogen, halogen, fluorine, cyano, nitro, $CF_3$, $OCF_3$, alkyl, methyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NH_2$; wherein n is 4; wherein $R_3$ is selected from the group consisting of hydrogen, halogen, fluorine, cyano, $CF_3$, $OCF_3$, alkyl, methyl, substituted alkyl, halogen-substituted alkyl, hydroxyl-substituted alkyl, amine-substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NR_bR_c$; wherein $R_a$ is/are independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, and substituted aryl; and wherein $R_b$ and $R_c$ are independently selected from the group consisting of hydrogen, alkyl, substituted alkyl, cycloalkyl, substituted cycloalkyl, heterocycle, substituted heterocycle, aryl, and substituted aryl, or $R_b$ and $R_c$ together with the N to which they are bonded form a heterocycle or substituted heterocycle.

In some embodiments, each ($R_1$) is independently selected from the group consisting of hydrogen, methyl, F (fluorine), Cl, Br, I, OH, and $NH_2$; $R_3$ is selected from the group consisting of methyl and $C(R_8)_3$, and each ($R_8$) is independently selected from the group consisting of hydrogen, methyl, F (fluorine), Cl, Br, I, OH, and $NH_2$. In some embodiments, at most two of ($R_1$) and ($R_8$) are F (fluorine) with the remainder being hydrogen. In some embodiments, $R_3$ is methyl. In a further embodiment, the compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, an enantiomer, diastereomer, tautomer, and a salt or solvate thereof.

In some embodiments, the naphthofuran compound in particle form is a particle of Compound 1.

In some embodiments, the naphthofuran compound in particle form is a particle of a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. In some embodiments, the polymorph is a polymorph of 2-acetyl-4H, 9H-naphtho[2,3-b]furan-4,9-dione characterized by an X-ray diffraction pattern substantially similar to that set forth in FIG. 2. In some embodiments, the polymorph is a polymorph of 2-acetyl-4H, 9H-naphtho[2,3-b]furan-4,9-dione characterized by an X-ray diffraction pattern substantially similar to that set forth in FIG. 3.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

In some embodiments, the particle has a diameter of less than or equal to about 160 μm, about 150 μm, about 120 μm, about 100 μm, about 50 μm, about 40 μm, or about 20 μm. In a further embodiment, the particle has a diameter of less than or equal to about 10 μm, about 5 μm, about 4 μm, about 3 μm, about 2 μm, about 1 μm, about 0.5 μm, about 0.2 μm, or about 0.1 μm.

The present invention provides a particle or particles of a naphthofuran compound, for example, a compound of Formula I, which are active, i.e., have an efficacy and/or an antitumor activity. The active particle or particles have certain size, for example, has a diameter of less than or equal to about 200 μm, about 150 μm, about 100 μm, about 40 μm, or about 20 μm, about 10 μm, about 5 μm, about 4 μm, about 3 μm, about 2 μm, about 1 μm, about 0.5 μm, about 0.2 μm, or about 0.1 μm. The particle or particles that are larger than the certain size are either inactive or less active than the particles described herein.

In some embodiments according to the invention, a pharmaceutical composition includes particles of a compound, for example, a naphthofuran, according to Formula I or a salt or solvate thereof. For example, in some embodiments, a pharmaceutical composition includes particles of Compound 1. For example, in some embodiments, a pharmaceutical composition includes particles of a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. In some embodiments, the polymorph is a polymorph of 2-acetyl-4H, 9H-naphtho[2,3-b]furan-4,9-dione characterized by an X-ray diffraction pattern substantially similar to that set forth in FIG. 2. In some embodiments, the polymorph is a polymorph of 2-acetyl-4H, 9H-naphtho[2,3-b]furan-4,9-dione characterized by an X-ray diffraction pattern substantially similar to that set forth in FIG. 3.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

A fraction of the cumulative total of the particles can have a diameter of less than or equal to about 200 μm. In some embodiments, a fraction of a set of particles can be at least about 1%, at least about 5%, at least about 10%, at least about 20%, or at least about 30% of the total number of particles in the set. In some embodiments, the fraction is a substantial fraction. For example, a "substantial fraction" of a set of particles can be at least about 99%, at least about 95%, at least about 90%, at least about 85%, at least about 80%, at least about 75%, at least about 70%, at least about 60%, or at least about 50% of the total number of particles in the set. Each ($R_1$) can be independently selected from the group consisting of hydrogen, halogen, fluorine, cyano, nitro, $CF_3$, $OCF_3$, alkyl, methyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NH_2$. n can be a positive integer; for example, n can be 4. $R_3$ can be selected from the group consisting of hydrogen, halogen, fluorine, cyano, $CF_3$, $OCF_3$, alkyl, methyl, substituted alkyl, halogen-substituted alkyl, hydroxyl-substituted alkyl, amine-substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NR_bR_c$. The $R_a$ can be independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, and substituted aryl. $R_b$ and $R_c$ can be independently selected from the group consisting of hydrogen, alkyl, substituted alkyl, cycloalkyl, substituted cycloalkyl, heterocycle, substituted heterocycle, aryl, and substituted aryl, or $R_b$ and $R_c$ together with the N to which they are bonded form a heterocycle or substituted heterocycle.

In some embodiments according to the invention, each ($R_1$) can be independently selected from the group consisting of hydrogen, methyl, F (fluorine), Cl, Br, I, OH, and $NH_2$. $R_3$ can be selected from the group consisting of methyl and $C(R_8)_3$. Each ($R_8$) can be independently selected from the group consisting of hydrogen, methyl, F (fluorine), Cl, Br, I, OH, and $NH_2$. In some embodiments, at most two of ($R_1$) and $R_8$ can be F (fluorine) with the remainder being hydrogen.

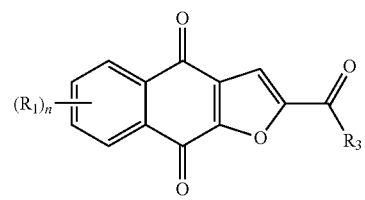

Formula I

In some embodiments according to the invention, a compound according to Formula I is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, and 2-ethyl-naphtho[2,3-b]furan-4,9-dione. In some embodiments, a compound according to Formula I is Compound 1. In some embodiments, a compound according to Formula I is a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. In some embodiments, the polymorph is a polymorph of 2-acetyl-4H, 9H-naphtho[2,3-b]furan-4,9-dione characterized by an X-ray diffraction pattern substantially similar to that set forth in FIG. 2. In some embodiments, the polymorph is a polymorph of 2-acetyl-4H, 9H-naphtho[2,3-b]furan-4,9-dione characterized by an X-ray diffraction pattern substantially similar to that set forth in FIG. 3.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

For example, the pharmaceutical composition can have at least about 90% of the cumulative total of particles having a particle size of less than or equal to about 160 μm, 100 μm, 40 μm, 20 μm, 10 μm, 5 μm, 3 μm, or 2 μm. For example, the pharmaceutical composition can have at least about 50% of the cumulative total of particles having a particle size of less than or equal to about 160 μm, 100 μm, 40 μm, 20 μm, 10 μm, 5 μm, 3 μm, 2 μm, 1 μm, or 0.5 μm. For example, the pharmaceutical composition can have at least about 10% of the cumulative total of the particles having a particle size of less than or equal to about 160 μm, 100 μm, 40 μm, 20 μm, 5 μm, 2 μm, 1 μm, 0.5 μm, or 0.1 μm. In the pharmaceutical composition, the particles can have a median diameter of, for example, less than or equal to about 160 μm, 40 μm, 20 μm, 10 μm, 5 μm, 4 μm 3 μm, 2 μm, 1 μm, 0.5 μm, 0.3 μm, or 0.2 μm. For example, the particles can have a median diameter of from about 0.2 μm to about 50 μm, or a median diameter of from about 0.5 μm to about 30 μm. For example, the pharmaceutical composition can have the cumulative total of particles having a ratio of mean diameter over median diameter of at most about 2 μm. The pharmaceutical invention can have particles that include the compound in a crystalline state, in at least two different polymorph states.

In some embodiments, the pharmaceutical composition includes a compound of Formula I or a polymorph thereof in particle form, where the particle or particles are less than 20 micron, 10 micron, 5 micron, 2 micron, 1 micron or 0.5 micron.

The present invention provides a substantially pure compound of Formula II,

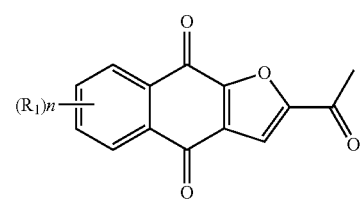

(II)

wherein each $R_1$ is independently H, Cl, or F; and n is 0, 1, 2, 3, or 4. In some embodiments, the compound of Formula II is in particle form.

In some embodiments, the substantially pure compound is Compound 1. In some embodiments, Compound 1 is in particle form.

In some embodiments, the substantially pure compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof.

In some embodiments, the substantially pure compound is a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. In some embodiments, the polymorph is a polymorph of 2-acetyl-4H, 9H-naphtho[2,3-b]furan-4,9-dione characterized by an X-ray diffraction pattern substantially similar to that set forth in FIG. 2. In some embodiments, the polymorph is a polymorph of 2-acetyl-4H, 9H-naphtho[2,3-b]furan-4,9-dione characterized by an X-ray diffraction pattern substantially similar to that set forth in FIG. 3.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

In some embodiments, the polymorph of Compound 1 is in particle form.

In some embodiments, the compound, product and or pharmaceutical composition has a purity of at least about 80%, about 85%, about 90%, about 95%, or about 99%. In some embodiments, the compound, product and or pharmaceutical composition has a purity of at least about 95.5%, about 96%, about 96.5%, about 97%, about 97.5%, about 98%, about 98.5%, about 99%, or about 99.5%. In some embodiments, the compound, product and or pharmaceutical composition has a purity of at least about 99.1%, about 99.2%, about 99.3%, about 99.4%, about 99.5%, about 99.6%, about 99.7%, about 99.8%, or about 99.9%.

In some embodiments, the compound, product and or pharmaceutical composition has impurities of at most about 10%, about 5%, about 1%, about 0.15%, or about 0.5%. In some embodiments, the compound, product and or pharmaceutical composition contains, for each single impurity, at most about 0.5%, about 0.2%, about 0.15%, or about 0.1%. In a further embodiment, the impurities are one or more from the group consisting of 2-acetyl-2,3-dihydronaphtho[2,3-b]furan-4,9-dione, 2,6-Diacetyl-naphtho[2,3-b]furan-4,9-dione, 2,7-Diacetyl-naphtho[2,3-b]furan-4,9-dione, 3-Acetyl-naphtho[2,3-b]furan-4,9-dione, Naphtho[2,3-b]furan-4,9-dione, Naphtho[2,3-b]furan-4,9-dione, Naphtho[2,3-b]furan-4,9-diol, and 1-(4,9-Dihydroxy-naphtho[2,3-b]furan-2-yl)-ethanone.

In some embodiments, the impurities include a residual solvent. In some embodiments, the solvent is selected from the group consisting of ethyl acetate (EtOAc), toluene, Ethanol, methanol, chloroform, and $CH_2Cl_2$/hexane.

In some embodiments, the purity is determined with HPLC (High Performance Liquid Chromatography). In some embodiments, the purity is determined with NMR (Nuclear Magnetic Resonance). In a further embodiment, the purity is determined with both HPLC and NMR.

The invention also provides a polymorph of Compound 1 in a particle form, where the compound is in a highly purified form, product and/or pharmaceutical composition. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. In some embodiments, the polymorph is a polymorph of 2-acetyl-4H, 9H-naphtho[2,3-b]furan-4,9-dione characterized by an X-ray diffraction pattern substantially similar to that set forth in FIG. 2. In some embodiments, the polymorph is a polymorph of 2-acetyl-4H, 9H-naphtho[2,3-b]furan-4,9-dione characterized by an X-ray diffraction pattern substantially similar to that set forth in FIG. 3.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

The polymorph of Compound 1 is in a particle form. In some embodiments, the polymorph of Compound 1 is in a particle form, where the particle has a diameter of less than or equal to about 160 µm, about 150 µm, about 120 µm, about 100 µm, about 50 µm, about 40 µm, or about 20 µm. In some embodiments, the polymorph of Compound 1 in particle form is in a population of particles, where the population of particles have a $D_{50}$ (i.e., the median point of the particle size distribution that divides the distribution in two equal parts) of less than or equal to about 160 µm, about 150 µm, about 120 µm, about 100 µm, about 50 µm, about 40 µm, or about 20 µm. In some embodiments, the polymorph of Compound 1 is in a particle form, where the particle has a diameter of less than or equal to about 10 µm, about 5 µm, about 4 µm, about 3 µm, about 2 µm, about 1 µm, about 0.5 µm, about 0.2 µm, or about 0.1 µm. In some embodiments, the polymorph of Compound 1 in particle form is in a population of particles, where the population of particles have a $D_{50}$ of less than or equal to about 10 µm, about 5 µm, about 4 µm, about 3 µm, about 2 µm, about 1 µm, about 0.5 µm, or about 0.2 µm.

The present invention provides a particle or a population of particles of a polymorph of Compound 1, which are active, i.e., have an efficacy and/or an antitumor activity. The active particle or particles have certain size, for example, has a diameter or $D_{50}$ of less than or equal to about 200 µm, about 150 µm, about 100 µm, about 40 µm, or about 20 µm, about 10 µm, about 5 µm, about 4 µm, about 3 µm, about 2 µm, about 1 µm, about 0.5 µm, or about 0.2 µm. The particle or particles that are larger than the certain size are either inactive or less active than the particles described herein.

A fraction of the cumulative total of the particles of a polymorph of Compound 1 can have a diameter or $D_{50}$ of less than or equal to about 200 µm. In some embodiments, a fraction of a set of particles can be at least about 1%, at least about 5%, at least about 10%, at least about 20%, or at least about 30% of the total number of particles in the set. In some embodiments, the fraction is a substantial fraction. For example, a "substantial fraction" of a set of particles can be at least about 99%, at least about 95%, at least about 90%, at least about 85%, at least about 80%, at least about 75%, at least about 70%, at least about 60%, or at least about 50% of the total number of particles in the set.

In some embodiments, the population of particles of a polymorph of Compound 1 can have at least about 90% of the cumulative total of particles having a particle size of less than or equal to about 160 μm, 100 μm, 40 μm, 20 μm, 10 μm, 5 μm, 3 μm, or 2 μm, 1 μm or 0.5 μm. For example, the population of particles of a polymorph of Compound 1 can have at least about 50% of the cumulative total of particles having a particle size of less than or equal to about 160 μm, 100 μm, 40 μm, 20 μm, 10 μm, 5 μm, 3 μm, 2 μm, 1 μm, or 0.5 μm. For example, the population of particles of a polymorph of Compound 1 can have at least about 10% of the cumulative total of the particles having a particle size of less than or equal to about 160 μm, 100 μm, 40 μm, 20 μm, 5 μm, 2 μm, 1 μm, 0.5 μm, or 0.1 μm. In the population of particles of a polymorph of Compound 1, the particles can have a median diameter of, for example, less than or equal to about 160 μm, 40 μm, 20 μm, 10 μm, 5 μm, 4 μm, 3 μm, 2 μm, 1 μm, 0.5 μm or 0.2 μm. For example, the particles can have a median diameter of from about 0.002 μm to about 50 μm, or a median diameter of from about 0.2 μm to about 30 μm. For example, the population of particles of a polymorph of Compound 1 can have the cumulative total of particles having a ratio of mean diameter over median diameter of at most about 2. The population of particles of a polymorph of Compound 1 can have particles that include the compound in a crystalline state, in at least two different polymorph states.

In some embodiments, the polymorph of Compound 1 is in a particle form, where the particle has a diameter of less than or equal to about 20 micron, 10 micron, 5 micron, or 2 3 micron, 2 micron, 1 micron, 0.5 micron, 0.2 micron, or 0.1 micron. In some embodiments, the polymorph of Compound 1 in particle form is in a population of particles, where the population of particles have a $D_{50}$ of less than or equal to about 20 micron, 10 micron, 5 micron, 4 micron, 5 micron, 3 micron, 2 micron, 1 micron, 0.5 micron or 0.2 micron.

The present invention also provides a pharmaceutical composition, which includes a therapeutically effective amount of the substantially pure naphthofuran compound and a pharmaceutically acceptable carrier, excipient, or diluent. The excipient can include, for example, a glycerol ester of a fatty acid, a glycerol ester of a saturated fatty acid, a glycerol ester of a saturated fatty acid having from 8 to 18 carbons, glyceryl laurate, polyethylene glycol, cellulose, microcrystalline cellulose, carboxymethylcellulose, a phosphatidylcholine, a lipid, a sterol, cholesterol, a surfactant, a polysorbate, and/or a polyoxyethylene sorbitan alkylate.

In some embodiments according to the invention, an item of manufacture can include a container containing a therapeutically effective amount of the pharmaceutical composition and a pharmaceutically acceptable excipient.

A method for producing a compound, product and/or pharmaceutical composition according to some embodiments of the invention can include milling the compound to form the particles. For example, the compound can be ball milled, roll milled, jet milled, wet milled, ultrasonically milled, ground, or treated with a combination of these and/or other milling procedures. The temperature of the compound can be reduced, for example, reduced to a cryogenic temperature, and milled. Such reduction in temperature can render the compound more brittle and more amenable to particle size reduction by milling.

A method for producing a compound, product and/or pharmaceutical composition according to some embodiments of the invention can include crystallization. The particle size distribution (PSD) obtained during crystallization is influenced by a combination of various mechanisms that occur during crystallization, such as nucleation, growth, aggregation, attrition, breakage, etc. When the particle size cannot be consistently controlled during crystallization to meet the desired specifications, an extra processing step such as dry milling can be included.

A method according to the invention of treating, delaying the progression of, preventing a relapse of, alleviating a symptom of, or otherwise ameliorating a human, mammal, or animal subject afflicted with a neoplasm can include administering a therapeutically effective amount of the compound, product and/or pharmaceutical composition, so that anti-neoplastic activity occurs. For example, the anti-neoplastic activity can be anticancer activity. For example, the anti-neoplastic activity can include slowing the volume growth of the neoplasm, stopping the volume growth of the neoplasm, or decreasing the volume of the neoplasm. The neoplasm can include a solid tumor, a malignancy, a metastatic cell, a cancer stem cell. The neoplasm can include a carcinoma, a sarcoma, an adenocarcinoma, a lymphoma, or a hematological malignancy. The neoplasm can be refractory to treatment by chemotherapy, radiotherapy, and/or hormone therapy. The compound, product and/or pharmaceutical composition can be administered to prevent relapse of the neoplasm. The compound, product and/or pharmaceutical composition can be administered as an adjuvant therapy to surgical resection. The compound, product and/or pharmaceutical composition can be administered, for example, orally and/or intravenously.

A method according to the invention also includes treating, delaying the progression of, preventing a relapse of, alleviating a symptom of, or otherwise ameliorating a disease or disorder in a human, mammal, or animal subject afflicted with that disease or disorder. In some embodiments, the disease or disorder is selected from the group consisting of an autoimmune disease, an inflammatory disease, inflammatory bowel diseases, arthritis, autoimmune demyelination disorder, Alzheimer's disease, stroke, ischemia reperfusion injury and multiple sclerosis.

Administration of the compounds, products and/or pharmaceutical compositions to a patient suffering from a disease or disorder is considered successful if any of a variety of laboratory or clinical results is achieved. For example, administration is considered successful one or more of the symptoms associated with the disease or disorder is alleviated, reduced, inhibited or does not progress to a further, i.e., worse, state. Administration is considered successful if the disorder, e.g., an autoimmune disorder, enters remission or does not progress to a further, i.e., worse, state.

In some embodiments, the compounds, products and/or pharmaceutical compositions described herein are administered in combination with any of a variety of known therapeutics, including for example, chemotherapeutic and other anti-neoplastic agents, anti-inflammatory compounds and/or immunosuppressive compounds. In some embodiments, the compounds, products and/or pharmaceutical compositions described herein are useful in conjunction with any of a variety of known treatments including, by way of non-limiting example, surgical treatments and methods, radiation therapy, chemotherapy and/or hormone or other endocrine-related treatment.

These "co-therapies" can be administered sequentially or concurrently. The compounds, products and/or pharmaceutical compositions described herein and the second therapy can be administered to a subject, preferably a human subject, in the same pharmaceutical composition. Alternatively, the compounds, products and/or pharmaceutical compositions described herein and the second therapy can be administered concurrently, separately or sequentially to a subject in separate pharmaceutical compositions. The compounds, products and/or pharmaceutical compositions described herein and the second therapy may be administered to a subject by the same or different routes of administration. In some embodiments, the co-therapies of the invention comprise an effective amount of the compounds, products and/or pharmaceutical compositions described herein and an effective amount of at least one other therapy (e.g., prophylactic or therapeutic agent) which has a different mechanism of action than the compounds, products and/or pharmaceutical compositions described herein. In some embodiments, the co-therapies of the present invention improve the prophylactic or therapeutic effect of the compounds, products and/or pharmaceutical compositions described herein and of the second therapy by functioning together to have an additive or synergistic effect. In certain embodiments, the co-therapies of the present invention reduce the side effects associated with the second therapy (e.g., prophylactic or therapeutic agents).

In some embodiments, the disease or disorder can be treated by administering the compound, product and/or pharmaceutical composition as follows. The blood molar concentration of the compound can be at least an effective concentration and less than a harmful concentration for a first continuous time period that is at least as long as an effective time period and shorter than a harmful time period. The blood molar concentration can be less than the effective concentration after the first continuous time period. For example, the effective concentration can be about 0.1 µM, about 0.2 µM, about 0.5 µM, about 1 µM, about 2 µM, about 3 µM, about 4 µM, about 5 µM, about 6 µM, about 10 µM, or another concentration determined to be effective by one of skill in the art. For example, the harmful concentration can be about 1 µM, about 3 µM, about 10 µM, about 15 µM, about 30 µM, about 100 µM, or another concentration determined to be harmful by one of skill in the art. For example, the effective time period can be about 1 hour, 2 hour, about 4 hours, about 6 hours, about 8 hours, about 10 hours, about 12 hours, about 24 hours, or another time period determined to be effective by one of skill in the art. For example, the harmful time period can be about 12 hours, about 24 hours, about 48 hours, about 72 hours, about 144 hours, or another time period determined to be harmful by one of skill in the art.

In some embodiments, the therapeutically effective amount of the compound, product and/or pharmaceutical composition is selected to produce a blood concentration greater than the $IC_{50}$ of cells of the tumor and less than the $IC_{50}$ of normal cells. In some embodiments, the therapeutically effective amount is selected to produce a blood concentration sufficiently high to kill cells of the tumor and less than the $IC_{50}$ of normal cells.

In some embodiments, the compound, product and/or pharmaceutical composition is administered orally in a dosage form, for example, a tablet, pill, capsule (hard or soft), caplet, powder, granule, suspension, solution, gel, cachet, troche, lozenge, syrup, elixir, emulsion, oil-in-water emulsion, water-in-oil emulsion, and/or a draught.

In some embodiments according to the present invention, a composition for reducing or inhibiting the replication or spread of neoplastic cells includes a set of particles selected by the following method. A compound according to Formula I or a salt or solvate thereof can be provided.

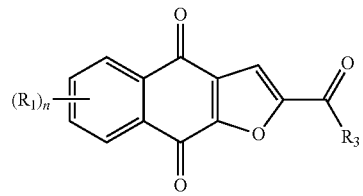

Formula I

In some embodiments, Compound 1 or a salt or solvate thereof can be provided. In some embodiments, a polymorph of Compound 1 can be provided. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. In some embodiments, the polymorph is a polymorph of 2-acetyl-4H, 9H-naphtho[2,3-b]furan-4,9-dione characterized by an X-ray diffraction pattern substantially similar to that set forth in FIG. 2. In some embodiments, the polymorph is a polymorph of 2-acetyl-4H, 9H-naphtho[2,3-b]furan-4,9-dione characterized by an X-ray diffraction pattern substantially similar to that set forth in FIG. 3.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

At least one set of particles including the compound can be prepared. The particle size distribution of each at least one set of particles can be determined. At least one set of particles can be administered to neoplastic cells and to normal cells at a predetermined concentration and for a predetermined period of time. The effect of the particles on the metabolism and/or division of the neoplastic cells and the normal cells can be observed. An effectivity rating can be assigned to each set of particles based on the effect of the particles on the neoplastic cells. A toxicity rating can be assigned to each set of particles based on the effect of the particles on the normal cells. The effectivity rating and/or the toxicity rating of the at least one set of particles having a first particle size distribution can be compared with the effectivity rating and/or the toxicity rating of at least one other set of particles having a particle size distribution different than the first particle size distribution. The set of particles having an effectivity rating greater than, a toxicity rating less than, and/or a weighted effectivity rating and toxicity rating sum greater than the at least one other set of particles can be selected as an optimum set. For example, the particle size distribution of the optimum set of particles can be identified as an optimum particle size distribution. For example, the optimum set of particles can be included in the composition. For example, the effectivity rating can be proportional to antitumor activity. For example, the effectivity rating can be based on inhibition of metabolism and/or division of the neoplastic cells. For example, the toxicity rating can be inversely proportional to tolerability. For example, the toxicity rating can be based on inhibition of metabolism and/or division of normal cells. For example, the at least one set of particles can be administered to the neoplastic cells and to the normal cells in vitro. For example, the effectivity rating can be the IC$_{50}$ of the neoplastic cells. For example, the toxicity rating can be the IC$_{50}$ of the normal cells. For example, the at least one set of particles can be administered to the neoplastic cells and to the normal cells in vivo in a test animal. The test animal can be, for example, a mammal, primate, mouse, rat, guinea pig, rabbit, or dog. The effectivity rating can be the decrease in volume of the neoplastic cells, and the toxicity rating can be the decrease in mass of the test animal.

In some embodiments, preparing the one set of particles including the compound can include isolating particles of a predetermined particle size distribution by dissolving and dispersing the compound, dissolving and dispersing the compound with a microfluidic technique, dissolving and dispersing the compound with cavitation or nebulization, milling the compound, ball milling the compound, roll milling the compound, jet milling the compound, wet milling the compound, ultrasonically milling the compound, grinding the compound, and/or sieving the compound. The particles can be suspended in a pharmaceutically acceptable excipient. Determining the particle size distribution can include using a technique selected from the group consisting of sieve analysis, optical microscopic counting, electron micrograph counting, electroresistance counting, sedimentation time, laser diffraction, acoustic spectroscopy, and combinations.

A method of treating a neoplasm or other cell proliferation disorder can include administering to a human, mammal, or animal afflicted with a neoplasm a therapeutically effective amount of a composition including an optimum set of particles of the composition having an optimum particle size and distribution.

The present invention also provides a process of preparing a compound of Formula II,

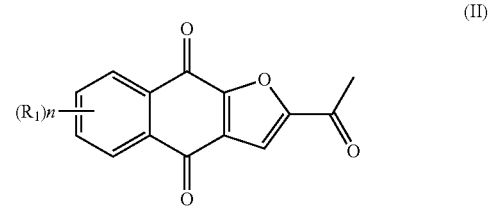

(II)

wherein R₁ is H, Cl, or F, the process including, reacting a compound of Formula III,

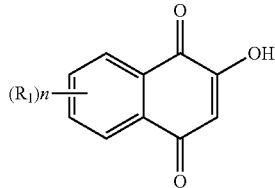

(III)

with a ketone in a first solvent while in the presence of a base, crystallizing crude product from the aged reaction mixture, and, reacting the crude product with an oxidizing agent in a second solvent.

In some embodiments, the reaction is carried out in an open air container.

In some embodiments, the ketone is a compound of Formula IV.

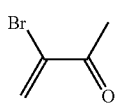

(4-3)

In some embodiments, the first solvent is selected from the group consisting of tetrahydrofuran (THF), dioxane, and toluene, and the base is selected from the group consisting of 1,8-diazabicyclo[5.4.0]undec-7-ene (DBU), triethyl amine, and diisopropylethyl amine. In some embodiments, the oxidizing agent is manganese dioxide. In some embodiments, the second solvent is toluene. In some embodiments, the process further includes treating the product of oxidation with charcoal.

The present invention provides a process of preparing a compound of Formula II,

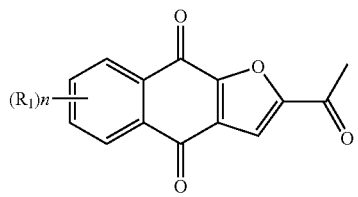

(II)

wherein R₁ is H, Cl, or F, the process including, reacting a compound of Formula III,

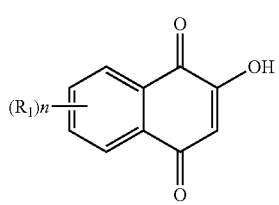

(III)

with a ketone in a first solvent while in the presence of a base, crystallizing crude product from the aged reaction mixture, dissolving the crude product in a second solvent, and, treating the crude product with charcoal.

The present invention provides a process of preparing a naphthofuran compound. The process includes reacting a naphthodihydrofurane compound or a mixture including the naphthodihydrofurane compound with an oxidizing agent in a first solvent. In some embodiments, the mixture further includes a naphthofuran compound. In some embodiments, the naphthofuran compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the oxidizing agent is manganese dioxide. In some embodiments, the first solvent is toluene. In some embodiments, the process further includes filtering the oxidization product through a pad of activated carbon. In some embodiments, the process further includes crystallizing the naphthofuran compound by evaporating the first solvent. In some embodiments, the process further includes re-crystallizing the naphthofuran compound with a second solvent. In some embodiments, the second solvent is ethyl acetate. In some embodiments, the process further includes slurrying the naphthofuran compound with a second solvent, heating the slurry, and cooling the slurry.

The present invention provides a process of preparing a substantially pure naphthofuran compound. The process includes crystallizing a naphthofuran compound with a first solvent, and re-crystallizing the naphthofuran compound with a second solvent. The present invention provides another process of preparing a substantially pure naphthofuran compound. The process includes crystallizing a naphthofuran compound with a first solvent, slurrying the crystalline naphthofuran compound with a second solvent, heating the slurry, and cooling the slurry. In some embodiments, the naphthofuran compound selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the first solvent is toluene. In some embodiments, the second solvent is ethyl acetate.

The present invention provides a naphthofuran compound prepared by any one of the above processes. In some embodiments, the naphthofuran compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the naphthofuran compound has a purity of at least about 80%, about 85% or about 90%, about 95%, or about 99%. In some embodiments, the naphthofuran compound has impurities of at most about 10%, about 5%, about 2%, or about 1%, about 0.5%, about 0.2%, about 0.15%, or about 0.1%.

The invention provides methods for preparing particles of Compound 1, including particles of a polymorph of Compound 1, particles of highly pure forms of Compound 1 and particles of highly pure forms of a polymorph of Compound 1. In some embodiments, particles having a desired median particle size, for example, about 20 microns, are produced by milling crystals of Compound 1, including crystals of a purified form of Compound 1, crystals of a polymorph of Compound 1 and/or crystals of a purified form of a polymorph of Compound 1. For example, the crystals are milled using a jet milling method where the venturi pressure is about 40, the mill pressure is about 100, and the feed rate is approximately 1304 g/hour.

BRIEF DESCRIPTION OF THE DRAWINGS

FIGS. 6A-6D are a series of illustrations depicting the synthetic process for Crystal Form 3.

DETAILED DESCRIPTION OF THE INVENTION

Figure 1:
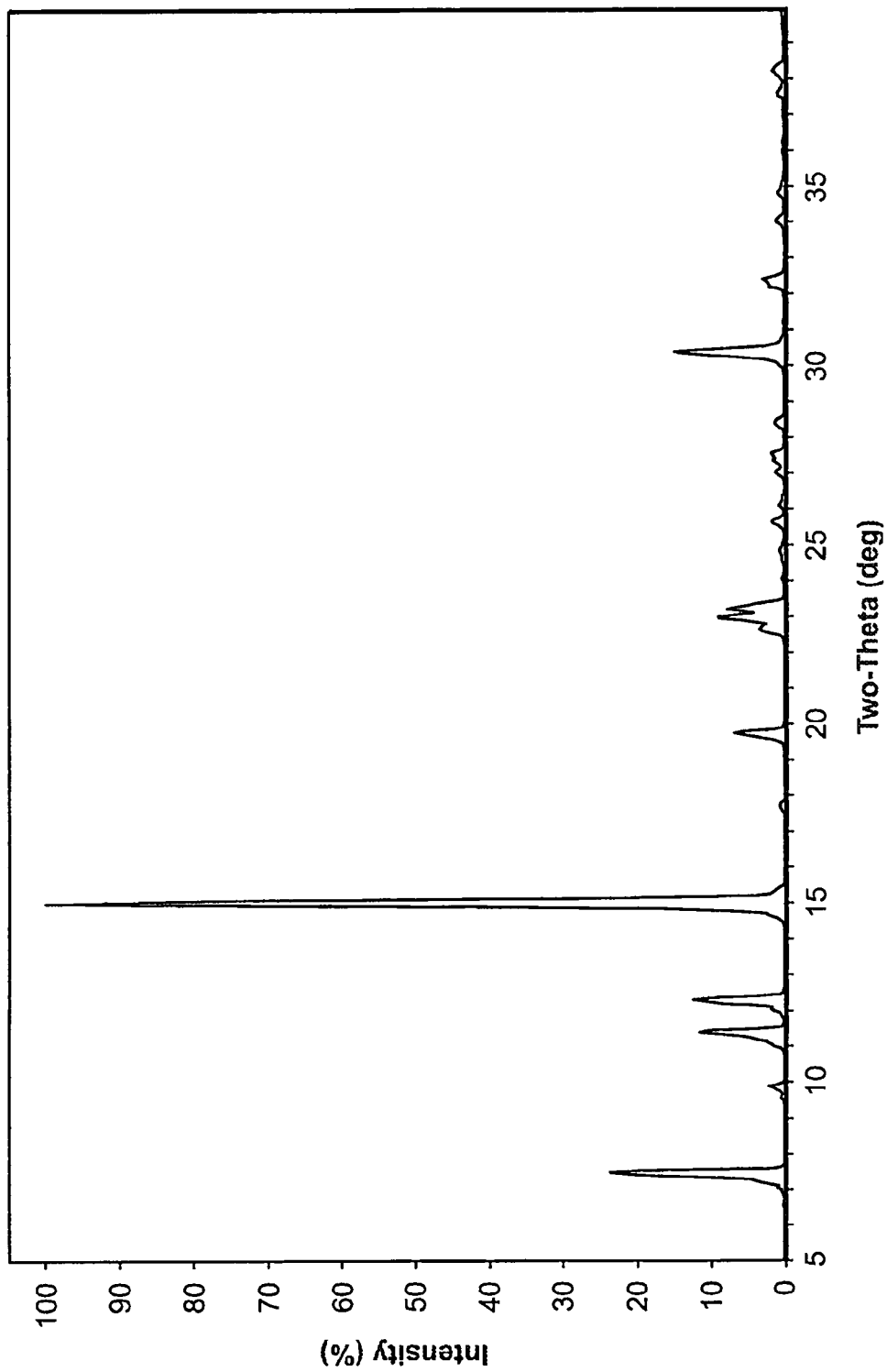
FIG. 1 is an illustration depicting XRPD Data of Crystal Form 1.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without parting from the spirit and scope of the invention. All references cited herein are incorporated by reference as if each had been individually incorporated.

In this text, a "substantial fraction" of a set of particles can be at least about 99%, at least about 95%, at least about 90%, at least about 85%, at least about 80%, at least about 75%, at least about 70%, at least about 60%, or at least about 50% of the total number of particles in the set.

The anti-cancer stem cell activity of a composition can be determined in vitro or in vivo. For example, antitumor activity of a composition can be determined in vitro by administering the compound and measuring the self-renewal and survival of cancer stem cells, For example, the antitumor activity of a compound can be assessed in vitro by comparing the behavior of tumor cells to which the compound has been administered with the behavior of tumor cells to which the compound has not been administered (a control). For example, antitumor activity of a composition can be determined in vivo by measuring, in an animal to which the compound has been administered, the change in volume of a tumor, by applying a metastatic model, and/or by applying an orthotopic model. For example, the antitumor activity of a compound can be assessed in vivo by comparing an animal to which the compound has been administered to an animal to which the compound has not been administered (a control).

The tolerability of a composition can be determined in vitro or in vivo. For example, tolerability of a composition can be determined in vitro by administering the compound and measuring the division rate of normal cells, by measuring the nutrient uptake of normal cells, by measuring indicators of metabolic rate of normal cells other than nutrient uptake, by measuring the growth of normal cells, and/or by measuring another indicator of the vitality of normal cells. For example, the tolerability of a compound can be assessed in vitro by comparing the behavior of normal cells to which the compound has been administered with the behavior of normal cells to which the compound has not been administered (a control). For example, tolerability of a composition can be determined in vivo by measuring, in an animal to which the compound has been administered, body weight or food intake or making clinical observations, such as hair retention or loss, activity, and/or responsiveness to stimuli. For example, the tolerability of a compound can be assessed in vivo by comparing an animal to which the compound has been administered to an animal to which the compound has not been administered (a control).

A compound, product and/or pharmaceutical composition can be assigned an effectivity rating and/or a toxicity rating. For example, the effectivity rating can be proportional to antitumor activity or can be a monotonically increasing function with respect to antitumor activity. For example, the toxicity rating can be inversely proportional to tolerability or can be a monotonically decreasing function with respect to tolerability. A naphthofuran compound has been reported to lack in vivo antitumor activity. See, M. M. Rao and D. G. I. Kingston, J. Natural Products, 45(5) (1982) 600-604. Furthermore, the compound has been reported to be equally toxic to cancer cells and normal cells. That is, the compound was reported as killing both cancer cells and normal cells equally, concluding the compound has no potential for cancer treatment. See, K. Hirai K. et al., Cancer Detection and Prevention, 23(6) (1999) 539-550; Takano A. et al., Anticancer Research 29:455-464, 2009.

However, experimental studies reported herein indicate that when the compound is administered as particles having an appropriate particle size distribution to achieve a certain pharmacokinetic exposure as described in this publication, the compound does have selective antitumor activity.

For the purposes of the present invention, "bioavailability" of a drug is defined as the relative amount of drug from an administered dosage form which enters the systemic circulation and the rate at which the drug appears in the blood stream. Bioavailability is governed by at least three factors: (i) absorption which controls bioavailability, followed by (ii) its tissue re-distribution and (iii) elimination (metabolic degradation plus renal and other mechanisms).

"Absolute bioavailability" is estimated by taking into consideration tissue re-distribution and biotransformation (i.e., elimination) which can be estimated in turn via intravenous administration of the drug. Unless otherwise indicated, "HPLC" refers to high performance liquid chromatography; "pharmaceutically acceptable" refers to physiologically tolerable materials, which do not typically produce an allergic or other untoward reaction, such as gastric upset, dizziness and the like, when administered to a mammal; "mammal" refers to a class of higher vertebrates including man and all other animals that nourish their young with milk secreted by mammary glands and have the skin usually more or less covered with hair; and "treating" is intended to encompass relieving, alleviating, or eliminating at least one symptom of a disease(s) in a mammal.

The term "treatment", as used herein, is intended to encompass administration of compounds according to the invention prophylactically to prevent or suppress an undesired condition, and therapeutically to eliminate or reduce the extent or symptoms of the condition. Treatment also includes preventing the relapse of an undesired condition, delaying the progression of an undesired condition, and preventing or delaying the onset of an undesired condition. Treatment according to the invention is given to a human or other mammal having a disease or condition creating a need of such treatment. Treatment also includes application of the compound to cells or organs in vitro. Treatment may be by systemic or local administration.

An effective amount is the amount of active ingredient administered in a single dose or multiple doses necessary to achieve the desired pharmacological effect. A skilled practitioner can determine and optimize an effective dose for an individual patient or to treat an individual condition by routine experimentation and titration well known to the skilled clinician. The actual dose and schedule may vary depending on whether the compositions are administered in combination with other drugs, or depending on inter-individual differences in pharmacokinetics, drug disposition, and metabolism. Similarly, amounts may vary for in vitro applications. It is within the skill in the art to adjust the dose in accordance with the necessities of a particular situation without undue experimentation. Where disclosed herein, dose ranges do not preclude use of a higher or lower dose of a component, as might be warranted in a particular application.

The descriptions of pharmaceutical compositions provided herein include pharmaceutical compositions which are suitable for administration to humans. It will be understood by the skilled artisan, based on this disclosure, that such compositions are generally suitable for administration to any mammal or other animal. Preparation of compositions suitable for administration to various animals is well understood, and the ordinarily skilled veterinary pharmacologist can design and perform such modifications with routine experimentation based on pharmaceutical compositions for administration to humans.

Compound Structure and Properties

A naphthofuran compound of Formula I, such as 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, was practically insoluble in water and a broad panel of solvents tested, including DMSO (dimethyl sulfoxide), N-methylpyrrolidine, DMA (dimethylacetamide), ethanol, PEG400 (polyethylene glycol 400), propylene glycol, Cremophor EL (polyethoxylated castor oil), Labrasol (Caprylocaproyl Macrogolglycerides (Polyoxylglycerides)), Labrafil M (vegetable oil PEG-6 (polyethylene glycol) ester), and Capryol (propylene glycol caprylate). The naphthofuran compound may be soluble in a range of polar organic solvents, such as certain halocarbons, e.g., chlorocarbons, like methylene chloride, esters, ethyl acetate, carboxylic acids, like acetic acid, ketones, like acetone, and alcohols, like methanol. The naphthofuran compound was found to be soluble in methylene chloride and ethyl acetate.

The experimental studies described herein, which found that selective antitumor activity was achieved by administering the active compound of a pharmaceutical composition in the form of small particles to achieve a certain pharmacokinetic exposure for selective anticancer activity, focused on a naphthofuran compound. Given the presently discussed observations made with the compound, other naphthofurans, for example, naphthofurans, may similarly exhibit an advantageous modification of their pharmacokinetic profiles to the achievement of a certain pharmacokinetic exposure to achieve selective anti-cancer activity when administered in the form of particles of small diameter. The pharmacokinetic profile of other naphthofurans administered as one or more different particle size distributions can be experimentally determined.

Some other compounds that may exhibit an improvement in their pharmacokinetic profile and efficacy with a decrease in particle size of the form in which they are administered to an animal, a mammal, or a human, as observed for the compound tested in examples, include those presented as Formula I, and salts and solvates thereof.

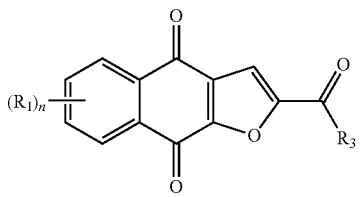

Formula I

In Formula I, the notation $(R_1)_n$ indicates that an $(R_1)$ substituent is independently substituted at each available position along the benzene ring. For example, with n equal to 4, the four $R_1$ substituents may all be the same, or they may each be different from any other. For example, each $(R_1)$ can be independently selected from the group consisting of hydrogen, halogen, fluorine, cyano, nitro, $CF_3$, $OCF_3$, alkyl, methyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NH_2$. Alkyl can include moieties having, for example, from 1 to 8 carbon atoms connected by single bonds, alkenyl can include moieties having, for example, from 2 to 8 carbon atoms connected by one or more double bonds, and alkynyl can include moieties having, for example, from 2 to 8 carbon atoms connected by one or more triple bonds. Substituents can include moieties such as hydrogen, halogen, cyano, nitro, aryl, $OR_a$, $SR_a$, and $NH_2$. For example, each $(R_1)$ can be independently selected from the group consisting of hydrogen, methyl, F (fluorine), Cl (chlorine), Br (bromine), I (iodine), OH (hydroxyl), and $NH_2$ (amine). For example, $R_3$ can be selected from the group consisting of hydrogen, halogen, fluorine, cyano, $CF_3$, $OCF_3$, alkyl, methyl, substituted alkyl, halogen-substituted alkyl, hydroxyl-substituted alkyl, amine-substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, substituted aryl, $OR_a$, $SR_a$, and $NR_bR_c$. For example, $R_3$ can be selected from the group consisting of methyl and $C(R_8)_3$. Each $(R_8)$ can be independently selected from the group consisting of hydrogen, methyl, F (fluorine), Cl, Br, I, OH, and $NH_2$. For example, at most two of the independently selected $(R_1)$ substituents and the $(R_8)$ substituents can be selected to be F (fluorine), with the remainder being selected to be hydrogen.

In some embodiments, the compound of Formula I is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, an enantiomer, diastereomer, tautomer, and a salt or solvate thereof. For example, each $(R_1)$ can be selected to be hydrogen and $R_3$ can be selected to be methyl, so that the compound of Formula I is 2-acetylnaphtho[2,3-b]furan-4,9-dione. For example, each $R_a$ can be independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, heterocycle, substituted heterocycle, aryl, and substituted aryl. For example, each $R_b$ and $R_c$ can be independently selected from the group consisting of, hydrogen, alkyl, substituted alkyl, cycloalkyl, substituted cycloalkyl, heterocycle, substituted heterocycle, aryl, and substituted aryl. Alternatively, an $R_b$ and $R_c$ together with the N to which they are bonded can form a heterocycle or substituted heterocycle.

Polymorphs

Naphthofuran compounds of the invention include polymorphs. In some embodiments, the polymorph is a polymorph of a compound according to Formula I. In some embodiments, the polymorph is a polymorph of Compound 1. For example, in some embodiments, the polymorph is a polymorph of 2-acetyl-4H, 9H-naphtho[2,3-b]furan-4,9-dione characterized by an X-ray diffraction pattern substantially similar to that set forth in FIG. 1. This polymorph is referred to herein as "Crystal Form 1," "Form 1," or "XRPD1" and these terms are used interchangeably. In some embodiments, the polymorph is a polymorph of 2-acetyl-4H, 9H-naphtho[2,3-b]furan-4,9-dione characterized by an X-ray diffraction pattern substantially similar to that set forth in FIG. 2. This polymorph is referred to herein as "Crystal Form 2," "Form 2," or "XRPD2" and these terms are used interchangeably. In some embodiments, the polymorph is a polymorph of 2-acetyl-4H, 9H-naphtho[2,3-b]furan-4,9-dione characterized by an X-ray diffraction pattern substantially similar to that set forth in FIG. 3. This polymorph is referred to herein as "Crystal Form 3," "Form 3," or "XRPD3" and these terms are used interchangeably.

For example, in some embodiments, the polymorph is a polymorph of 2-acetyl-4H, 9H-naphtho[2,3-b]furan-4,9-dione characterized by an X-ray diffraction pattern including one or more peaks at least at about 10.2, 11.4, 11.9, 14.1, 14.5, 17.3, 21.0, 22.2, 24.0, 26.0, and 28.1 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 10.2, 11.9, 14.1, 14.5, 17.3, 22.2, and/or 28.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 10.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 11.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.1 degrees 2θ. In some embodiments, the polymorph is a polymorph of 2-acetyl-4H, 9H-naphtho[2,3-b]furan-4,9-dione characterized by an X-ray diffraction pattern including a peak at least at about 14.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 17.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 22.2 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.1 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof.

For example, in some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 11.4, 12.3, 15.0, 23.0, 23.3, 24.1, 24.6, 25.0, 26.1, 27.0, and 28.4 degrees 2θ. In some embodiments, the polymorph is a polymorph of 2-acetyl-4H, 9H-naphtho[2,3-b]furan-4,9-dione characterized by an X-ray diffraction pattern including one or more peaks at least at about 7.5, 9.9, 12.3, 15, 23.0, 23.3, 24.6 and/or 28.4 degrees 2θ. In some embodiments, the polymorph is a polymorph of 2-acetyl-4H, 9H-naphtho[2,3-b]furan-4,9-dione characterized by an X-ray diffraction pattern including a peak at least at about 7.5 degrees 2θ. In some embodiments, the polymorph is a polymorph of 2-acetyl-4H, 9H-naphtho[2,3-b]furan-4,9-dione characterized by an X-ray diffraction pattern including a peak at least at about 9.9 degrees 2θ. In some embodiments, the polymorph is a polymorph of 2-acetyl-4H, 9H-naphtho[2,3-b]furan-4,9-dione characterized by an X-ray diffraction pattern including a peak at least at about 12.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 15 degrees 2θ. In some embodiments, the polymorph is a polymorph of 2-acetyl-4H, 9H-naphtho[2,3-b]furan-4,9-dione characterized by an X-ray diffraction pattern including a peak at least at about 23 degrees 2θ. In some embodiments, the polymorph is a polymorph of 2-acetyl-4H, 9H-naphtho[2,3-b]furan-4,9-dione characterized by an X-ray diffraction pattern including a peak at least at about 23.3 degrees 2θ. In some embodiments, the polymorph is a polymorph of 2-acetyl-4H, 9H-naphtho[2,3-b]furan-4,9-dione characterized by an X-ray diffraction pattern including a peak at least at about 24.6 degrees 2θ. In some embodiments, the polymorph is a polymorph of 2-acetyl-4H, 9H-naphtho[2,3-b]furan-4,9-dione characterized by an X-ray diffraction pattern including a peak at least at about 28.4 degrees 2θ. In some embodiments, the polymorph is a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 15 degrees 2θ, a peak at least at about 12.3 degrees 2θ, a peak at least at about 23.0 degrees 2θ, a peak at least at about 23.3 degrees 2θ, a peak at least at about 24.6 degrees 2θ and a peak at least at about 28.4 degrees 2θ and any combinations thereof.

Figure 8:
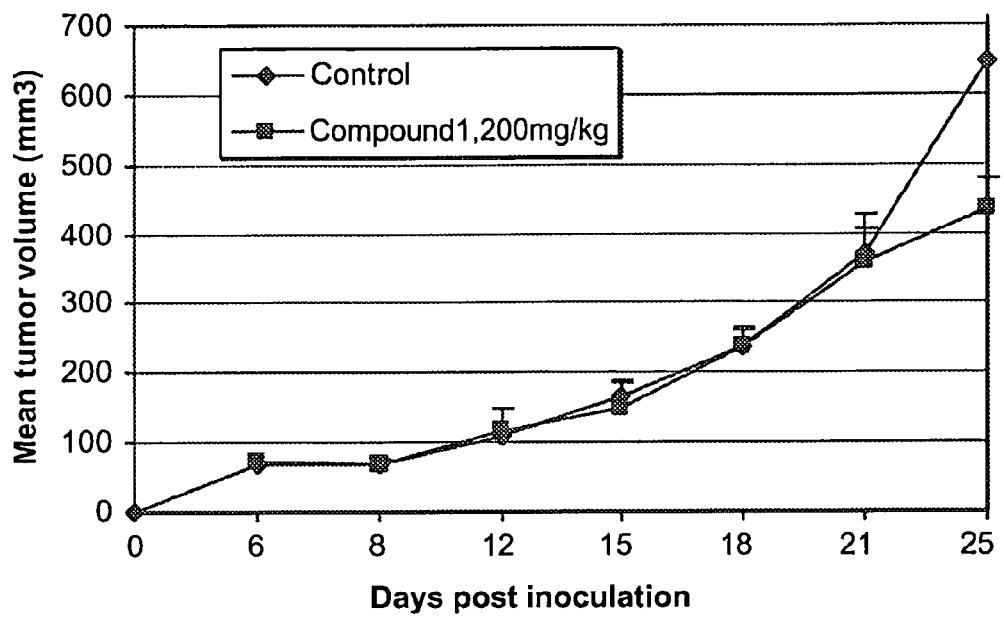
FIG. 8 is a graph depicting the limited anti-tumor activity of Crystal Form 1.

Crystal Form 1 has been detected in a variety of solvents and conditions, but has been shown to have low anti-tumor activity (FIG. 8). In the studies shown in FIG. 8, immunosuppressed mice with established subcutaneous FaDu human head and neck cancer were given indicated amount of hand grounded Compound 1 with Crystal Form 1, or vehicle control orally (po). Compound 1 was formulated in GELUCIRE™. All regimens were administered daily (qd). Tumor sizes were evaluated periodically during treatment.

Figure 9:
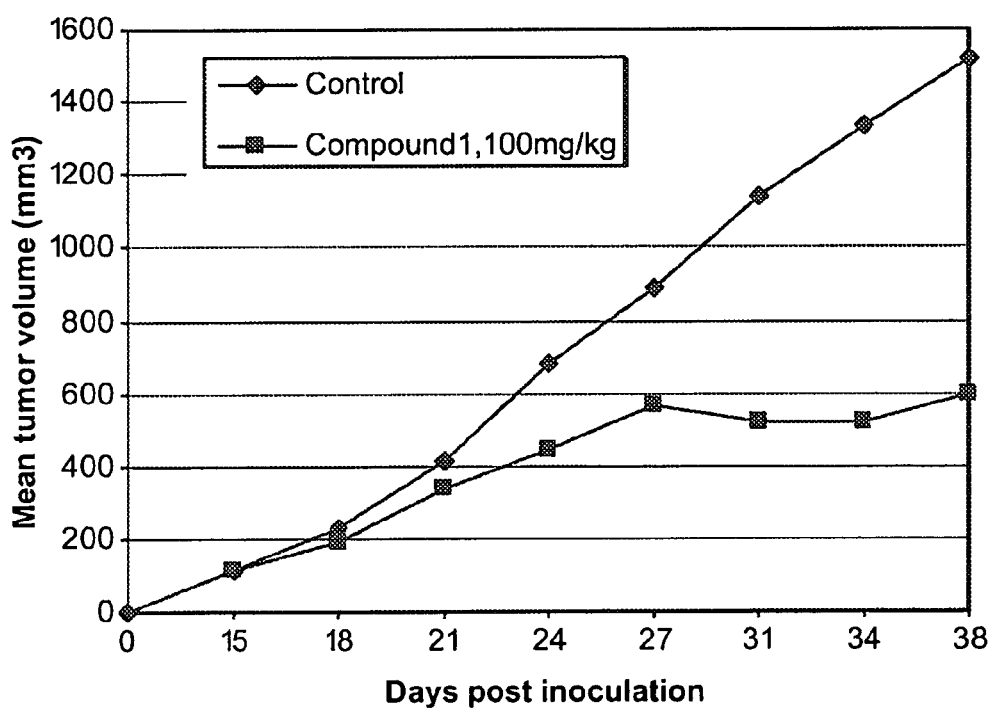
FIG. 9 is a graph depicting the antitumor activity of Crystal Form 2.
Figure 11:
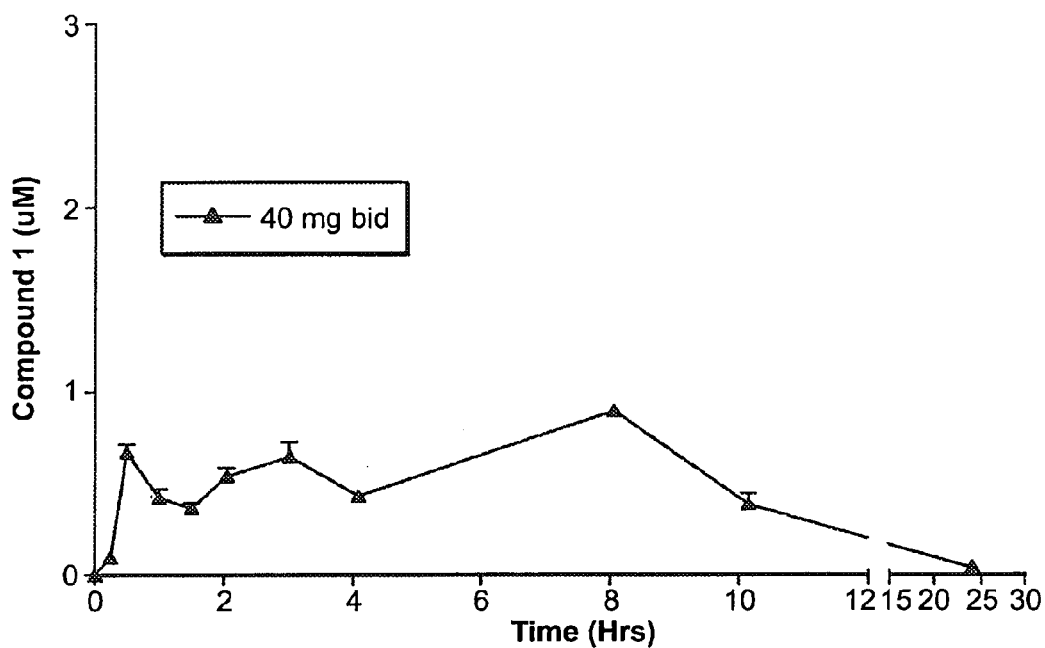
FIG. 11 is a graph depicting clinical pharmacokinetic (PK) data in cancer patients for Crystal Form 2.

Crystal Form 2 was obtained surprisingly in the presence of an impurity, and this polymorph has been shown to exhibit potent anti-tumor activity (FIG. 9). In the study shown in FIG. 9, immunosuppressed mice with established subcutaneous FaDu human head and neck cancer were given 100 mg/kg of micronized Compound 1 produced with the synthetic process described in FIGS. 5A and 5B (first crop), or vehicle control orally (po). Compound 1 was formulated in GELUCIRE™. All regimens were administered daily (qd). Tumor sizes were evaluated periodically during treatment. Form 2 has been successfully manufactured by a current good manufacturing practice (cGMP) process and received approval from the FDA and Health Canada to be used in clinical trials. Form 2 has shown desirable pharmacokinetics (FIG. 11), safety, and strong signs of anti-tumor activity in cancer patients.

Figure 7A:
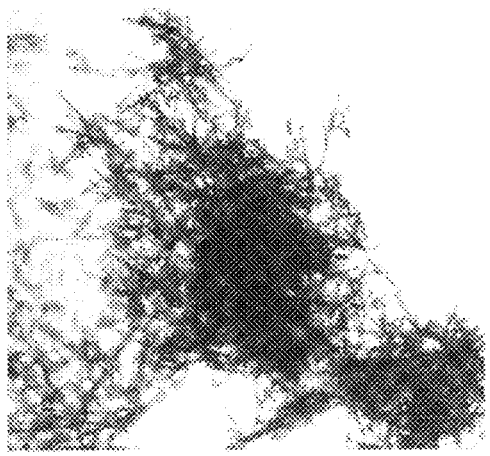
FIGS. 7A and 7B are photographs depicting the morphology of Crystal Forms 1 and 3.
Figure 7B:
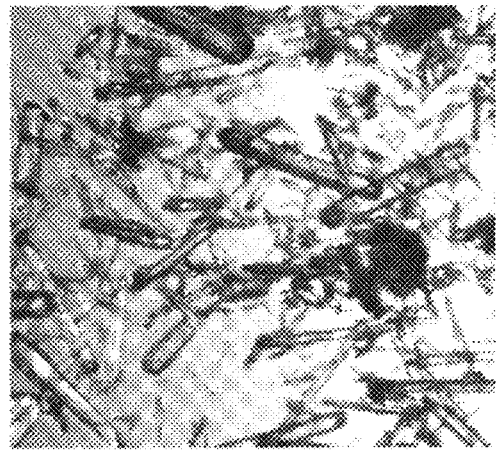
Figure 10:
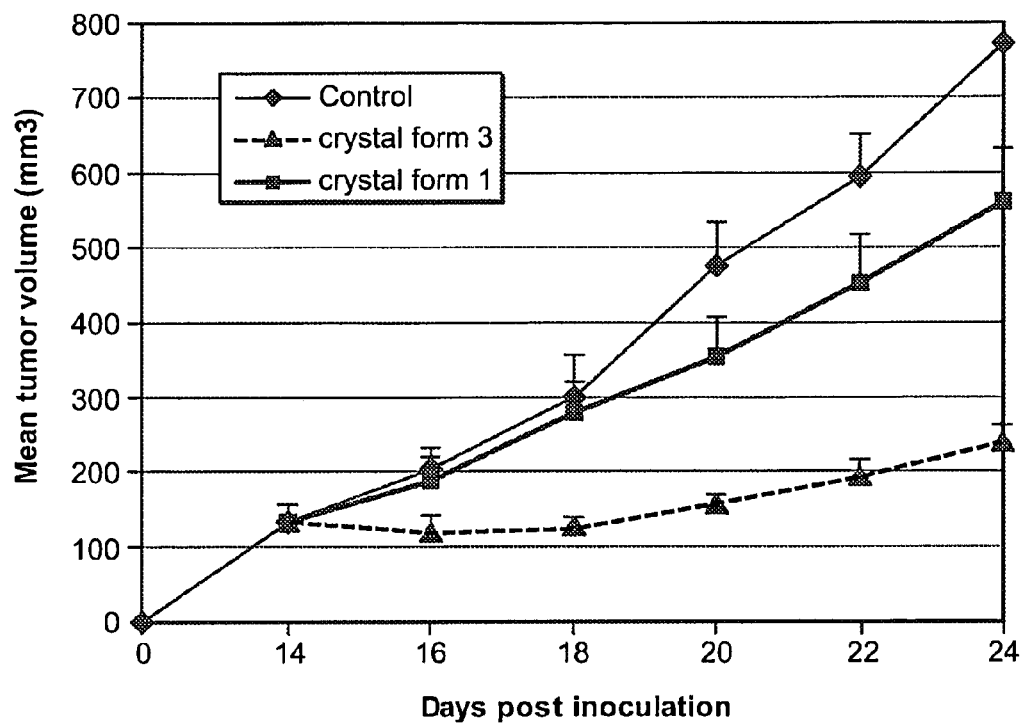
FIG. 10 is a graph depicting the comparison of antitumor activity of Crystal Form 1 and Crystal Form 3.

Crystal Form 3 has been shown to share a similar, but different, X-ray powder diffraction (XRPD) pattern as Form 1, and displayed very different crystalline habit than Form 1 (FIGS. 7A and B). Form 3 can only be generated from Form 1 using a specially designed slurry process described herein. Form 3 has been shown to exhibit potent antitumor activities (FIG. 10). In the study shown in FIG. 10, immunosuppressed mice with established subcutaneous FaDu human head and neck cancer were given 200 mg/kg of Compound 1 with hand grounded Crystal Form 1 or Form 3, or vehicle control orally (po). Compound 1 was formulated in gelucire. All regimens were administered daily (qd). Tumor sizes were evaluated periodically during treatment. This polymorph has been successfully manufactured by a cGMP process and received approval from FDA and Health Canada to be used in clinical trials. Form 3 has also shown desirable pharmacokinetics (FIG. 12), safety, and strong signs of anti-tumor activity in cancer patients.

Figure 5A:
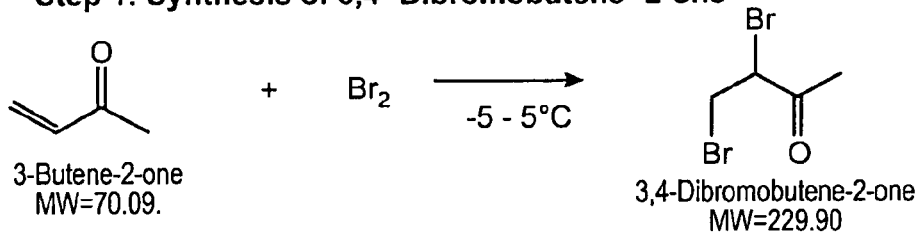
FIGS. 5A and 5B are a series of illustrations depicting the synthetic process for Crystal Form 2.
Figure 5A:
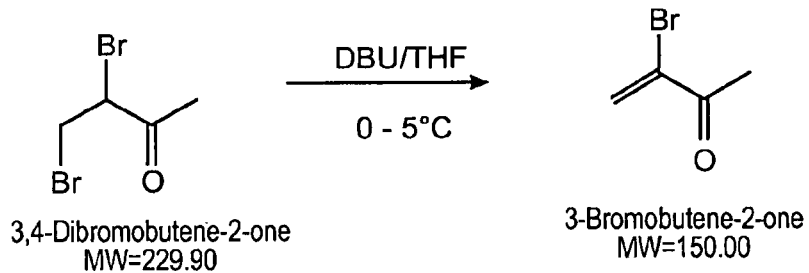
Figure 5A:
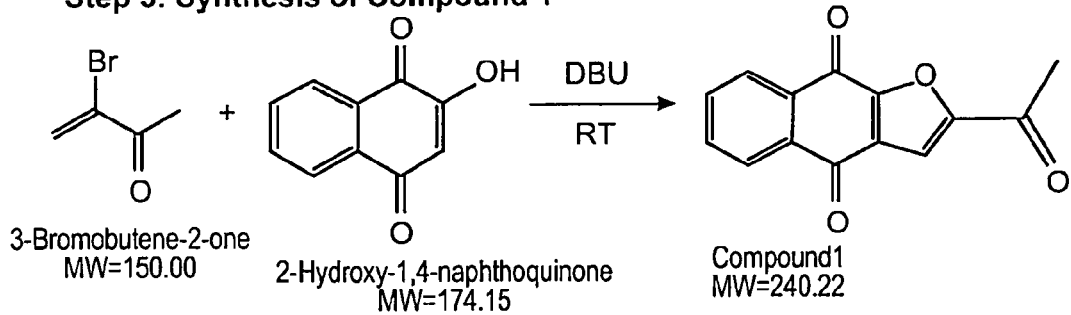
Figure 5B:
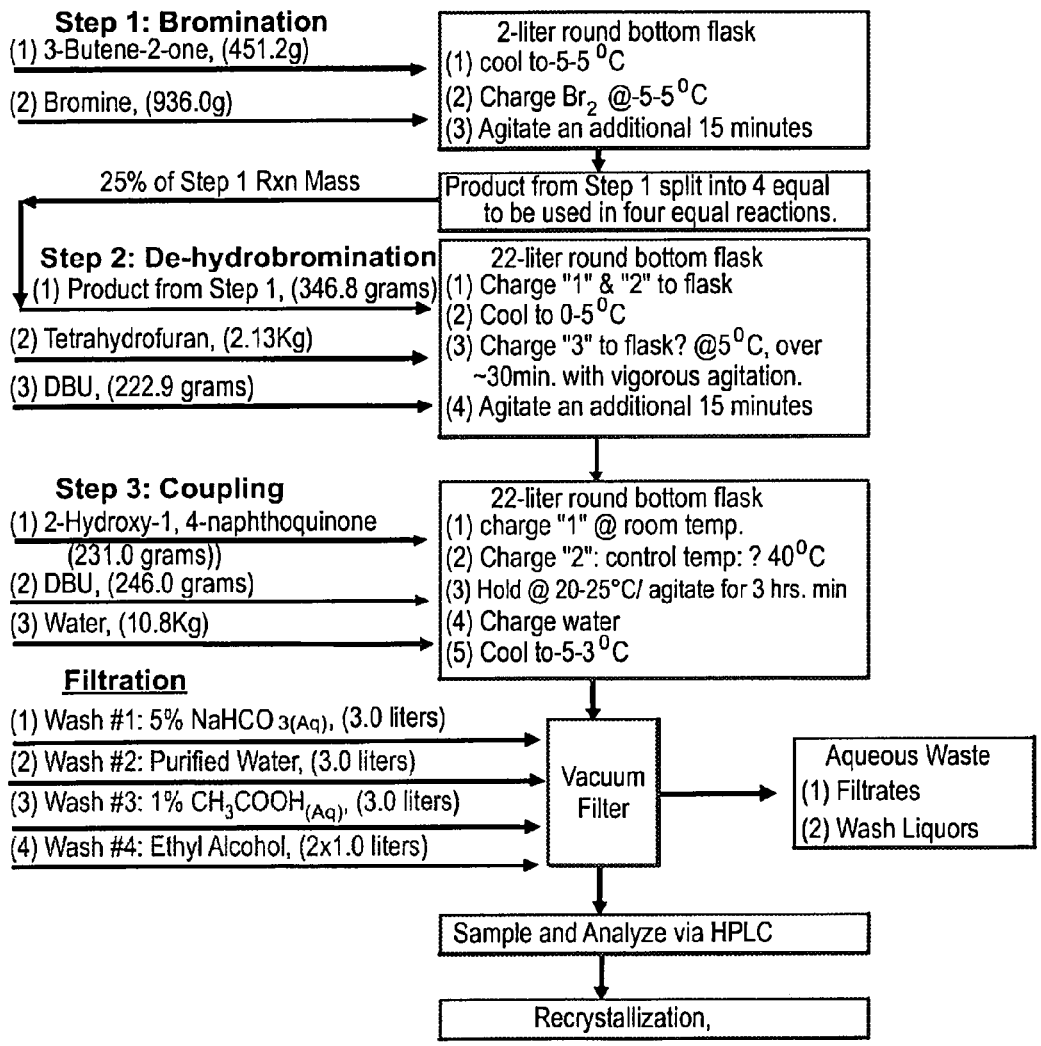
Figure 6C:
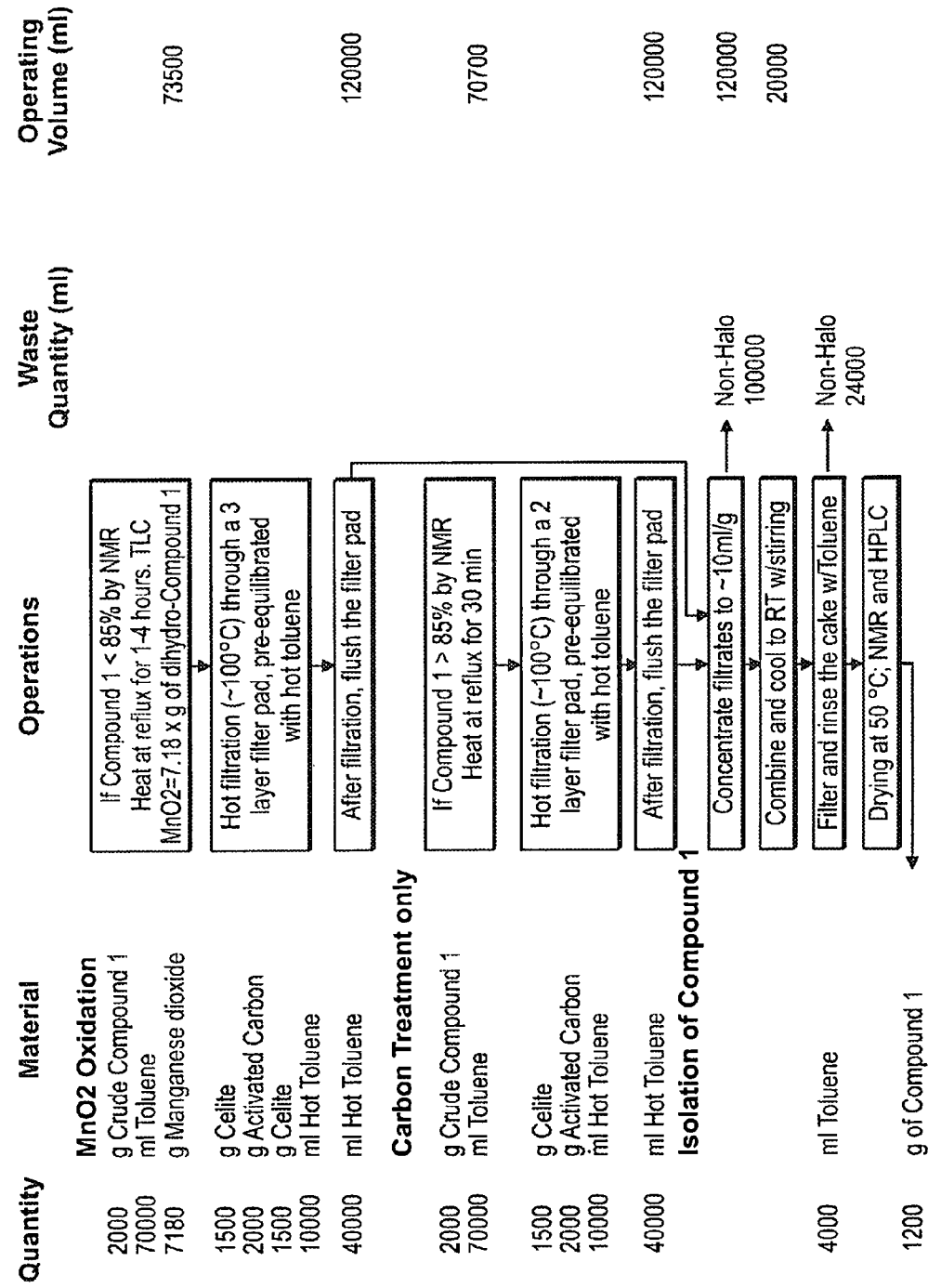
Figure 6D:
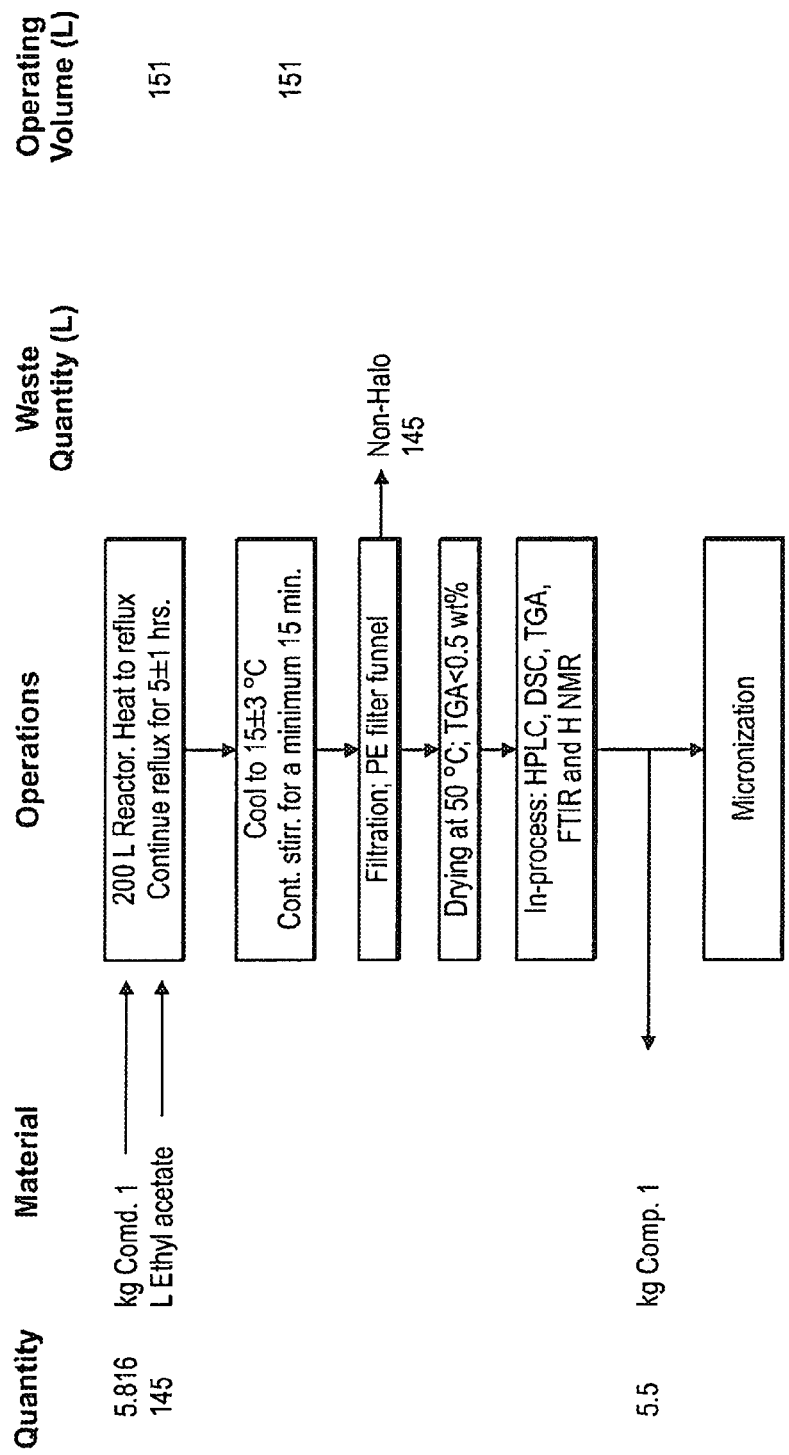

The synthetic process for preparing Crystal Form 2 is shown in FIGS. 5A-5B. Briefly, charged 3-butene-2-one (451.2 grams) is added to a 2 liter 3 neck round bottom flask equipped with a mechanical stirrer, thermometer, and addition funnel. To the addition funnel is added bromine (936.0 grams). After the contents in the flask have cooled to −5° C., the bromine is dropped into the flask with vigorous stirring and maintaining temperature at −5° C. over 30 minutes. The mixture is stirred for an additional 15 minutes at −5° C., and then is split into 4 equal portions. Each portion of the mixture along with tetrahydrofuran (2133.6 grams) is loaded into a 22 liter 4 neck round bottom flask equipped with a mechanical stirrer, thermometer, and addition funnel Charged DBU (1,3-Diazabicyclo[5.4.0]undec-7-ene, 222.9 grams) is added to the addition funnel. The DBU is dropped into the flask with vigorous stirring and maintaining temperature at 0° C.-5° C. over 30 minutes. The mixture is stirred for an additional 15 min at 0° C.-5° C. 2-hydroxy-1,4-naphthoquinone (231 grams) is then added into the flask. Additional DBU (246.0 grams) is charged into the addition funnel and then dropped into the mixture in the flask at such a rate that the temperature of the reaction mixture does not exceed 40° C. After the addition of DBU is complete, the resulting mixture is stirred overnight at room temperature, and a sample of the reaction mixture is taken for HPLC analysis. To the reaction mixture, water (10.8 liters) is charged, and the resulting mixture is cooled to 0° C.-3° C. for at least 30 minutes, and then filtered via vacuum filter. The filtered solid is rinsed with 5% aqueous sodium bicarbonate (3 liters), water (3 liters), 1% aqueous acetic acid (3 liters) and ethanol twice (2×1 liter) successively. The rinsed solid is stored and pooled together from other batches. The combined crude product (28.73 kg) is loaded along with ethyl acetate (811.7 kg) into a 500 gallon vessel equipped with a mechanical stirrer, thermometer, and a condenser. Under nitrogen atmosphere, the mixture is heated to reflux (72° C.) for 2 hours, and then filtered with a 10 micron cartridge filter containing an active carbon layer to remove insolubles. Fresh hot ethyl acetate (10 kg) is used to rinse the vessel, transfer line and filter. The combined filtrate is cooled to 0-5° C. and held at this temperature for 2 hours, and then is filtered with 20 inch Buchner filter. The filtered solid product is rinsed with 0-5° C. ethyl acetate (5.7 kg), and dried under vacuum at 40° C. to a constant weight. The remaining filtrate is reduced in volume by 63% by evaporation, and the crystallization process is repeated again to generate a second crop of product which was also dried under the same condition as the first crop of product. Both crops obtained are Crystal Form 2. The first crop produced (0.5 kg) had a 99.5% purity by HPLC (~95% by NMR). The second crop produced (1.09 kg) had a 98.9% purity by HPLC (~90% by NMR).

The synthetic process for preparing Crystal Form 3 is shown in FIGS. 6A-6D. The steps are outlined briefly herein. Step 1: 3-Butene-2-one (methyl vinyl ketone, MVK) is brominated using bromine. No additional solvent is used. The intermediate 3,4-dibromobutan-2-one is dissolved in tetrahydrofuran (THF) and reacted with 1,8-diazabicyclo [5.4.0]undec-7-ene (DBU) to form a second intermediate, 3-bromo-3-buten-2-one. Once this reaction is complete, 2-hydroxy-1,4-naphthoquinone (HNQ) is added. A second portion of DBU is added, and the mixture is exposed to air. The reaction is quenched with water and the solids are collected by filtration. These solids are washed with aqueous sodium bicarbonate, aqueous acetic acid, water, and ethanol. The product is isolated by slurrying in ethanol and collecting the solids. Step 2: Residual amounts of the 2-acetyl-2,3-dihydronaphtho[2,3-b]furan-4,9-dione that accompany the desired 2-acetyl-4H, 9H-naphtho[2,3-b]furan-4,9-dione (Compound 1) are oxidized to Compound 1 with activated manganese dioxide in toluene. The mixture is filtered through a cake of charcoal and Celite. The filtrate is concentrated to precipitate the product, which is filtered and dried. Step 3: The solids are slurried in ethyl acetate (25 mL/g purified Compound 1) at 75° C.-80° C. for about 5 hr, collected by filtration, and dried. Compound 1 produced with this method is Crystal Form 3. Compound 1 produced with this method without the slurry process yielded Crystal Form 1.

Effect of Compound Particle Size Distribution on Blood Plasma Drug Concentration and Selective Antitumor Activity Prior to the instant invention, no microparticles of Compound 1 had been created and/or evaluated. Previous studies had shown Compound 1 to be equally toxic to normal and cancer cells, and no antitumor activity was observed in animal model. The studies presented herein demonstrate that particle size reduction of Compound 1 not only improved bioavailability, but also led to increased selective anti-tumor activity without signs of toxicity. This is unexpected since improvement on bioavailability would increase exposure to Compound 1 equally by cancer cells and normal cells. The mechanism for the selective enhancement of anticancer activity without enhancement of toxicity to normal cells was not known. In these studies, the improvement in bioavailability of Compound 1 appeared to be maximized when the $D_{50}$ (i.e., the median point of the particle size distribution that divides the distribution in two equal parts) is about 20 μm. However, further studies were conducted where the $D_{50}$ value was about 2 μm. Microparticles of Compound 1 having a $D_{50}$ of 2 microns had surprisingly enhanced anti-tumor activity, even though there is no improvement in pharmacokinetic exposure as compared to particles with a $D_{50}$ of 20 microns. In additional studies, nanoparticles of Compound 1 having a $D_{50}$ of about 100 nanometers (D50=110.4 nanometers) were created, but surprisingly, a reduction of anti-tumor activity was observed with this particle size of Compound 1. Accordingly, in a preferred embodiment, compositions that contain particles of Compound 1, e.g., microparticles, have a $D_{50}$ equal to or below 20 microns and equal to or above 0.2 microns and possesses surprisingly potent anti-tumor activity without increase in cytotoxicity to normal cells.

Figure 15:
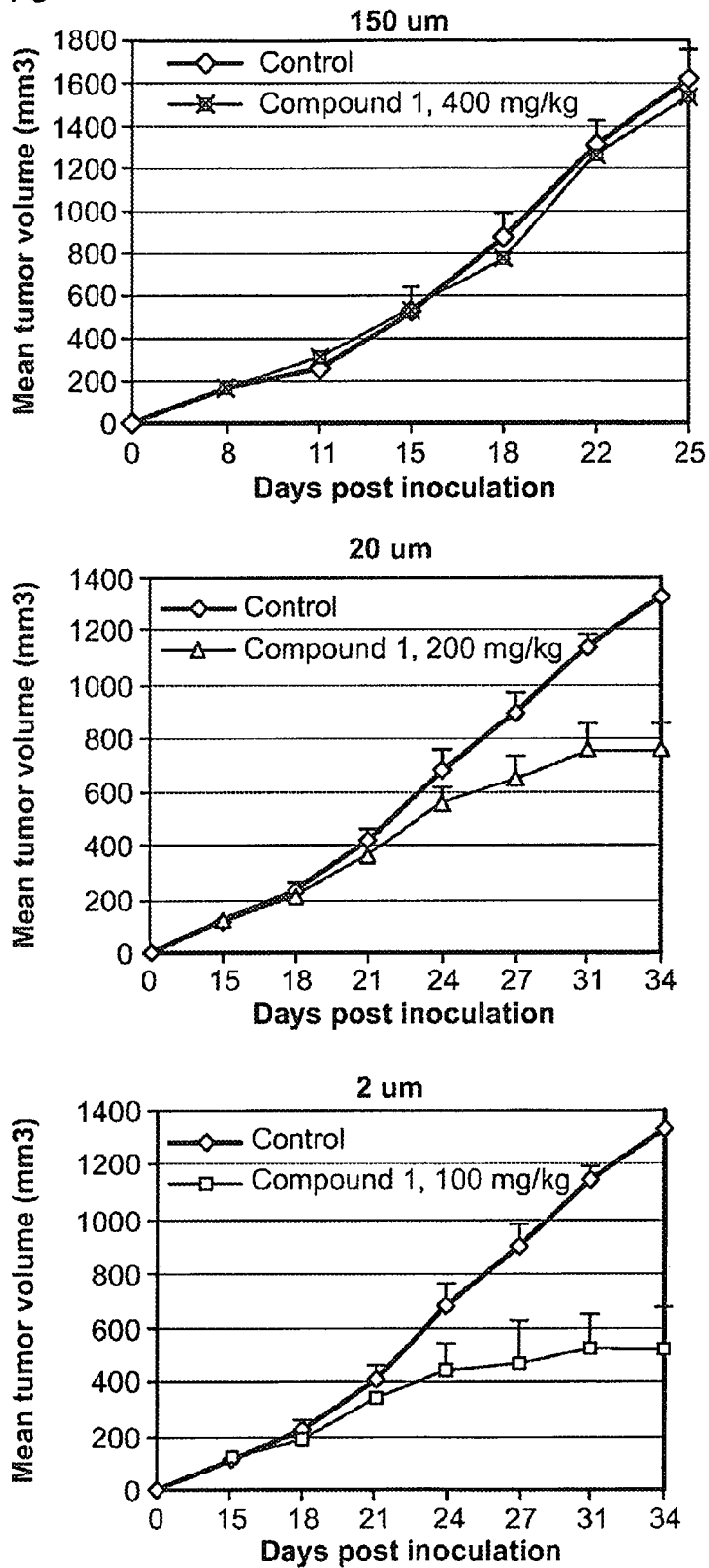
FIG. 15 is a graph depicting the anti-tumor activity of Compound 1 with different particle size ranges.
Figure 16:
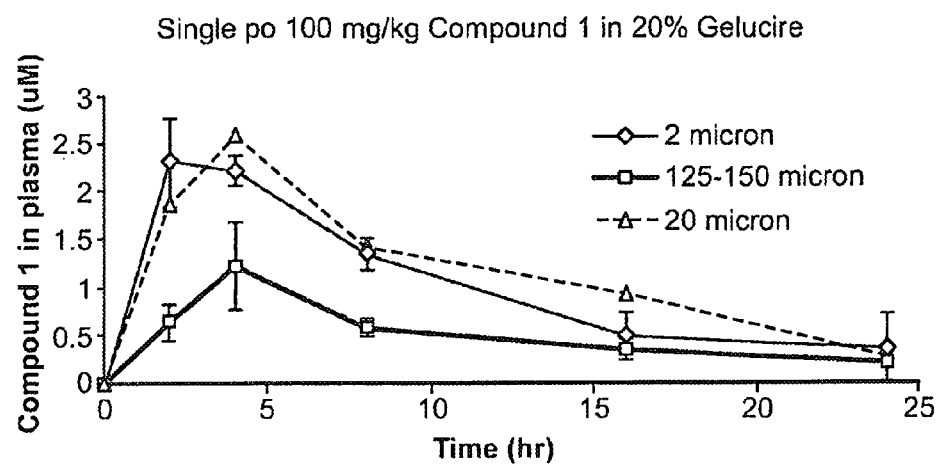
FIG. 16 is a graph depicting in vivo PK data of Compound 1 with different particle size ranges.
Figure 17:
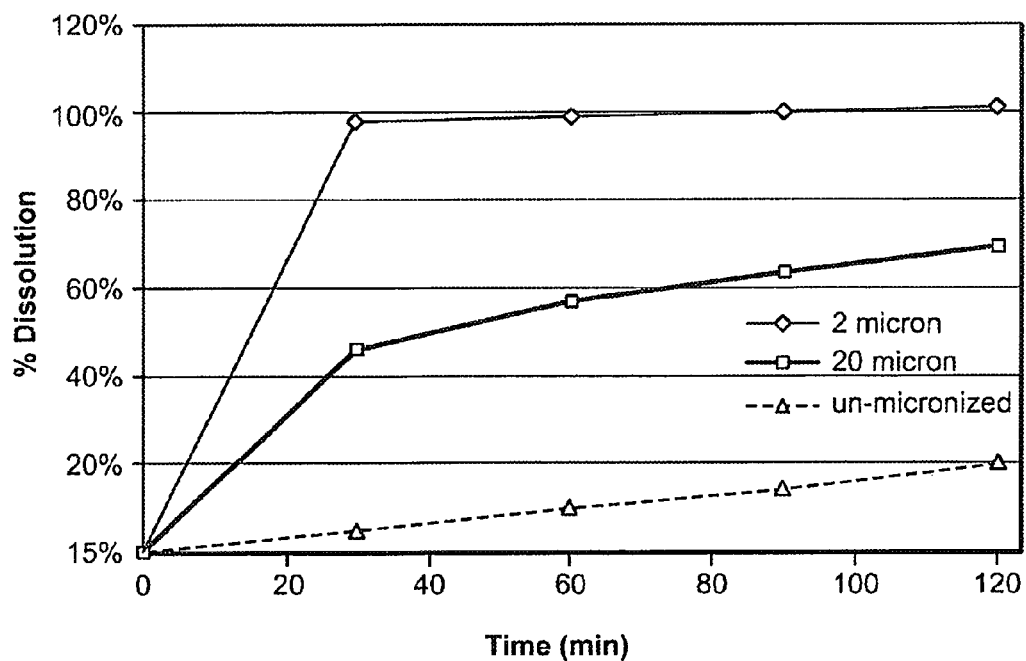
FIG. 17 is a graph depicting the relationship between dissolution and particle size of Compound 1.
Figure 18:
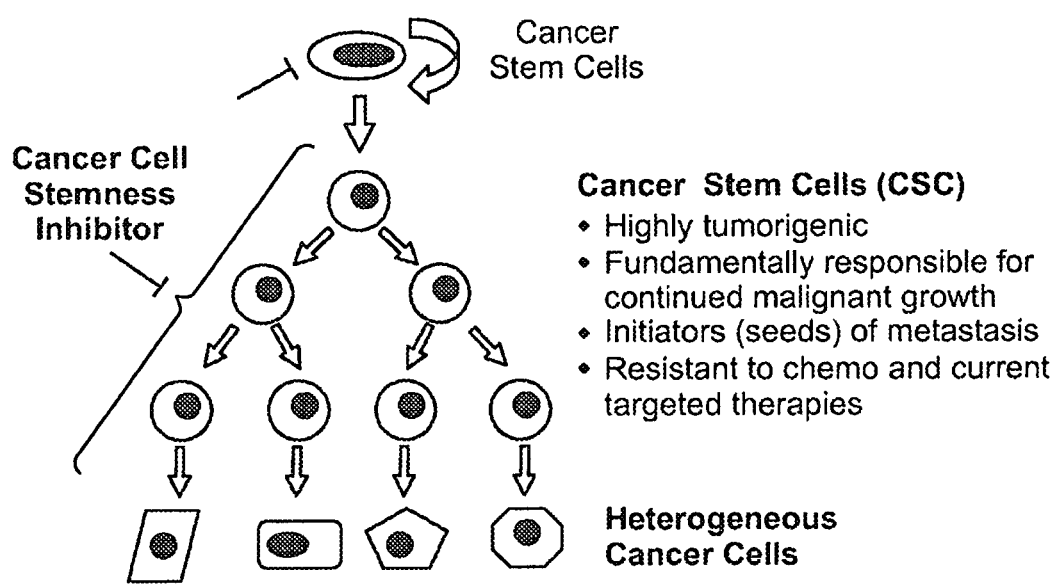
FIG. 18 is an illustration depicting the differences between cancer-stem-cell-specific and conventional cancer therapies.

The anti-tumor activity of particles of Compound 1 with different particle size ranges is illustrated in FIG. 15, and the pharmacokinetic data for particles of Compound 1 with different particle size ranges is illustrated in FIGS. 16-18. In the study shown in FIG. 15, immunosuppressed mice with established subcutaneous FaDu human head and neck cancer were given indicated amount of Compound 1 with indicated particle size, or vehicle control orally (po). All regimens were administered daily (qd). Tumor size was evaluated periodically.

Administering the naphthofuran compound in the form of particles having defined particle size, e.g., a reduced particle size, was found to enhance plasma drug concentration in vivo. Herein, unless otherwise noted, the terms "size" and "diameter" will be used interchangeably to describe particles. It is to be understood that the use of the term "diameter" does not necessarily imply that a particle has a perfectly or approximately spherical form. For example, "diameter" can be used as an approximation of the size of a particle, for example, the diameter of a sphere of equivalent volume to a non-spherical particle.

In a surprising result, the administration of the naphthofuran compound particles of a defined particle size distribution, e.g., as small particles, in a pharmaceutical composition was found to result in selective antitumor activity. For example, the compound administered as particles having a median particle size of 20 μm (i.e., microns, these terms are used interchangeable herein) showed efficacy (selective antitumor activity), although relative weak, in mouse xenograft models. In comparison, the particles of 150 μm (microns) showed no efficacy. The discovery that the administration of the naphthofuran compound in the form of smaller particles can result in selective antitumor activity is surprising, and cannot be explained on the basis of an improvement in solubility or bioavailability alone. That is, in general, improved solubility is associated with increased drug oral bioavailability, which can enhance toxicity to normal cells as well as antitumor activity. As discussed above, the naphthofuran compound can be equally toxic to tumor cells and normal cells if the exposure is not carried out under defined conditions as described in WO 2009/036099 and WO 2009/036101.

In a further surprising result, the administration of the naphthofuran compound particles of a further reduced size, in a pharmaceutical composition was found to result in a significantly improved antitumor activity but almost an unaltered pharmacokinetic profile, i.e., unaltered bioavailability. For example, the compound administered as particles having a median particle size of 2 μm (microns) showed dramatically enhanced efficacy in mouse xenograft models. In comparison with the particles of 20 μm, the particles of 2 μm showed significantly improved efficacy but very similar pharmacokinetic profile. In other words, such an improved efficacy is independent of pharmacokinetic profile, i.e., bioavailability. The result is very surprising, because for such a compound with poor solubility, improved efficacy is usually associated with increased drug oral bioavailability.

The observed improvement in the selective antitumor activity is therefore surprising and unexpected. The present invention provides a particle or particles of a naphthofuran compound, for example, a compound of Formula I, which are active, i.e., have an efficacy or a selective antitumor activity. The active particle or particles have a defined particle size, for example, has a diameter of less than or equal to about 200 µm, about 150 µm, about 100 µm, about 40 µm, or about 20 µm, about 10 µm, about 5 µm, about 4 µm, about 3 µm, about 2 µm, about 1 µm, about 0.5 µm, about 0.2 µm, or about 0.1 µm. The particle or particles that are larger than the defined particle size are either inactive or less active than the particles described herein.

Thus, the administration of the naphthofuran compound or another Compound according to Formula I in the form of smaller particles can result in an improvement in its selective antitumor activity. The use of particles of a compound according to Formula I having a defined particle size distribution in dosing can allow for the establishment of desired selective antitumor activity. For example, the use of the naphthofuran compound particles having a defined particle size distribution, for example, being smaller particles, can result in a higher blood concentration for a shorter period of time, and a selective antitumor activity, although relative weak. Further reduced particle size of the compound can lead to significantly improved efficacy with unaltered blood plasma concentration of the compound.

Herein, unless otherwise indicated, the term "blood plasma concentration", "blood molar concentration", and "blood concentration" are used interchangeably. The term "neoplasm" can be used to describe cells which exhibit an abnormal pattern of growth. Such a neoplasm can include tumors, both benign and malignant, e.g., solid tumors, as well as other cell growth disorders, such as leukemia, that have no defined shape and are not confined to a specific region of a human or animal body. Thus, "neoplasm" includes both cancerous and non-cancerous neoplastic cells and tissues. Herein, unless otherwise stated, made clear, or referring to a specific study or experiment, the terms "tumor" and "cancer" are to be understood as referring to the broader class of all neoplasms, including those that are not confined to a specific region of a human or animal body. However, the more limited term "solid tumor" is to be understood as not including cell growth disorders, such as leukemia, that have no defined shape and are not confined to a specific region of a human or animal body.

A neoplasm can exhibit none, one, or more than one of the following characteristics: solid form (a solid tumor), malignancy, metastasis, or Stat 3 pathway activity. A neoplasm can, for example, include a cancer stem cell. A neoplasm can be, for example, a carcinoma, sarcoma, adenocarcinoma, lymphoma, or a hematological malignancy.

Absorption has been defined as the process by which a drug is taken from the site of administration to the site of measurement within the body. See, M. Rowland, T. N. Tozer (1995) Clinical pharmacokinetics: Concepts and applications. Lippincott Williams & Wilkins. Oral drug absorption is often referred to as drug transfer across the apical membrane of the enterocyte, because the apical membrane is considered to be the rate limiting step for permeation of the membrane. See, U. Fagerholm & H. Lennernäs (1995) Experimental estimation of the effective unstirred water layer thickness in the human jejunum, and its importance in oral drug absorption, Eur J Pharm Sci 3: 247-253; M. B. Lande, J. M. Donovan & M. L. Zeidel (1995) The relationship between membrane fluidity and permeabilities to water, solutes, ammonia, and protons, J Gen Physiol 106: 67-84. Permeability is a general term describing how readily the drug is transferred through a membrane. The specific permeability characteristics of a drug are dependent on its physico-chemical properties, including lipophilicity, charge, size, and polar surface area. See, Rowland & Tozer 1995; C. A. Lipinski, F. Lombardo, B. W. Dominy & P. J. Feeney (2001) Experimental and computational approaches to estimate solubility and permeability in drug discovery and development settings, Adv Drug Deliv Rev 46: 3-26. The rate of absorption is dependent on the permeability of the drug, surface area of the membrane, and the concentration gradient over the membrane. The concentration gradient is the driving force for passive diffusion, the most common mechanism for drug membrane transport. For oral administration, the drug is mainly absorbed by intestine. Human intestine is about 5-8 meters long and has a total surface area of almost 200 square meters while mouse intestine is only about 10-20 cm long. Therefore, one can predict that a drug with a larger particle size may have a higher or same absorption rate in human as a drug with a smaller particle size does in mouse, despite the permeability of the drug with a larger particle size being lower than that of the drug with a smaller particle size.

For example, a distribution of particle sizes of a compound according to Formula I, having a median diameter of less than or equal to about 200 µm, 150 µm, 100 µm, 80 µm, 60 µm, 40 µm, 20 µm, 10 µm, 5 µm, 4 µm, 3 µm, 2 µm, 1 µm, 0.5 µm or 0.2 µm can be predicted to result in a selective antitumor activity when administered in a pharmaceutical formulation, e.g., for the treatment of a cancer or tumor. For example, the distribution of particle sizes can be such that the particles have a median diameter of from about 0.02 µm to about 5 µm, or from about 0.2 µm to about 4 µm. For example, the distribution of particle sizes can be such that the particles have a median diameter of less than or equal to about 5 µm, a ratio of mean diameter over median diameter of at most about 2, and a ratio of mode diameter over median diameter of at least about 0.25.

The term "particle" can refer to an aggregate of a compound of Formula I. The term "mean" can refer to the sum of the sizes of all particles divided by the total number of particles. The term "median" can refer to, e.g., a diameter of which one-half of the particles have a greater diameter and one-half of the particles have a lesser diameter. The term "mode" can indicate the most frequently-occurring particle size value. The term "cumulative total" can refer to all particles.

The selective antitumor activity achieved by administration of the naphthofuran compound particles may depend not only on the size distribution of the particles, e.g., the volumes of particles or diameters representative of those volumes, but also on the shape and distribution of shapes of the particles. For example, a set of particles having a needle-like shape may result in a different pharmacokinetic profile than a set of particles having a spherical shape. Thus, it may be desirable to measure the shape and shape distribution of the particles to be administered and/or use a process that produces particles with predetermined shape and shape distribution, for example, a nearly uniform shape, e.g., the particles being approximations of spheres. For example, the sphericity, $\Psi$, of a particle can be defined as $$\Psi = \frac{\pi^{1/3}(6V_P)^{2/3}}{A_P},$$

where $V_p$ is the volume of the particle and $A_p$ is the surface area of the particle. A sphere has a sphericity of $\Psi=1$, and the closer the sphericity of a particle is to unity, the more closely the shape of the particle approximates a sphere. By way of comparison, a tetrahedron has a sphericity of about 0.671, a cube has a sphericity of about 0.806, an octahedron has a sphericity of about 0.846, a dodecahedron has a sphericity of about 0.910, and an icosahedron has a sphericity of about 0.939. Because the form of a sphere minimizes surface area for a given volume, a particle that is nearly spherical may be expected to dissolve more slowly than a particle of the same volume that is less nearly spherical. The mean sphericity of a set of spheres can be defined as $$\Psi_m = \frac{\pi^{1/3}\left(6\sum V_P\right)^{2/3}}{\sum A_P},$$

where $\Sigma V_p$ is the total volume of all the particles and $\Sigma A_p$ is the total surface area of all the particles. For example, particles of a compound according to Formula I administered may have a mean sphericity of at least about 0.8, or a mean sphericity of at least about 0.9.

The size, size distribution, shape, shape distribution, and factors such as surface roughness or irregularity of the particles can affect the mean specific surface area of the set of Compound 1 particles administered in a pharmaceutical formulation. The mean specific surface area can be defined as $\Sigma A_p/\Sigma m_p$, where $\Sigma A_p$ is the total surface area of the particles and $\Sigma m_p$ is the total mass of the particles. The greater the mean specific surface area of the particles, the faster the expected dissolution of the particles.

The particles of a compound according to Formula I in a pharmaceutical formulation can include the naphthofuran compound in a crystalline state across different particles or within the same particle. The crystalline state may include one or more polymorphs, across different particles or within the same particle. As will be appreciated by one of skill in the art, it is expected that the dissolution rate of the particles can be effected by the state of matter in the compound particles, for example, whether crystalline, of a first polymorph, or a second polymorph.

One or more of a range of techniques can be applied to determine the size and/or size distribution of particles of a compound according to Formula I in a pharmaceutical formulation. For example, sieve analysis, optical microscopic counting, electron micrograph counting, electroresistance counting, sedimentation time, laser diffraction, and/or acoustic spectroscopy can be applied. Some or all of these techniques or variations thereof can be applied to determine the shape, shape distribution, and/or specific area of the naphthofuran compound particles in a pharmaceutical formulation. A BET isotherm and/or air permeability specific surface technique can be applied to determine the specific area of particles of a compound according to Formula I in a pharmaceutical formulation.

Processes for Generating Naphthofuran Compounds

WO 2009/036099 and WO 2009/036101 disclose a process for the preparation of a naphthofuran compound of Formula II as follows.

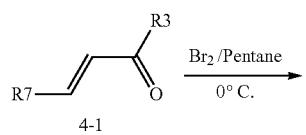

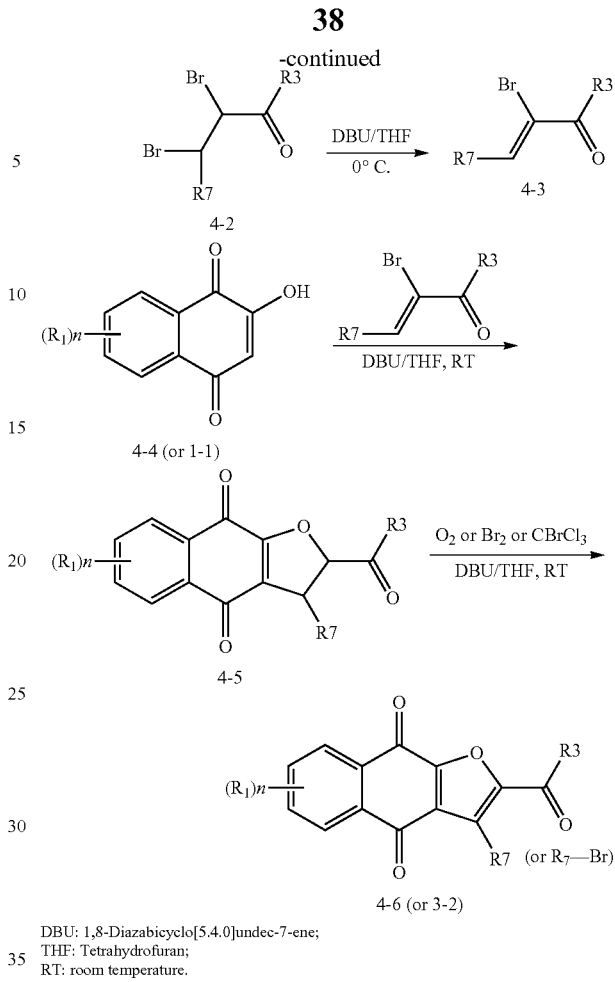

DBU: 1,8-Diazabicyclo[5.4.0]undec-7-ene;
THF: Tetrahydrofuran;
RT: room temperature.

In this process, 3-bromo-3-buten-2-one (4-3) is reacted with 2-hydroxy-1,4-naphthoquinone (4-4) in an open air container, resulting in 2,3-dihydronaphtho[2,3-b]furan-4,9-dione (4-5). 2,3-dihydronaphtho[2,3-b]furan-4,9-dione (4-5) is oxidized by oxygen from open air to become naphtho[2,3-b]furan-4,9-dione (4-6). With naphtho[2,3-b]furan-4,9-dione produced by this process. However, during further development of the compound, it was determined that this process still generated significant various impurities which hinders the potential clinical applications of these compounds. In some embodiments, one of the impurities is 2,3-dihydronaphtho[2,3-b]furan-4,9-dione (4-5).

In one aspect, the present invention provides an improved process for the preparation of naphthofuran. The improved process minimizes the impurities, and thereby produces substantially pure naphthofuran. As used herein the term "substantially pure" refers to a preparation including at least about 80% or more, measured as % area HPLC, of the compound of the present invention. In some embodiments, the naphthofuran is naphtho[2,3-b]furan-4,9-dione and its related compounds (4-6).

In some embodiments, the process of the present invention includes oxidizing the crude product of coupling of 3-bromo-3-buten-2-one (4-3) and 2-hydroxy-1,4-naphthoquinone (4-4) with an oxidizing agent in a first solvent. In a further embodiment, the oxidizing agent is manganese dioxide ($MnO_2$). In an even further embodiment, the crude product is isolated before it is oxidized. In some embodiments, the first solvent is toluene or chloroform.

In some embodiments, the process of the present invention further includes treating the aged oxidation mixture with charcoal to get rid of certain impurities. In a further embodiment, the aged oxidation mixture is filtered with a pad of activated carbon. In an even further embodiment, the mixture is filtered at around 100° C.

In some embodiments, the process of the present invention further includes crystallizing the product from the filtrate. In a further embodiment, the product is crystallized by concentrating the filtrate with evaporation, and cooling down.

In some embodiments, the process of the present invention further includes re-crystallizing the product with a second solvent. In a further embodiment, the second solvent is ethyl acetate.

In an alternative embodiment, the process of the present invention further includes slurrying in a second solvent the product crystallized from the first solvent, heating the slurry, and cooling the slurry. In a further embodiment, the second solvent is ethyl acetate. In some embodiments, the product is slurried and heated only to partial dissolution. In a further embodiment, the volume of the second solvent used to slurry the product is about 1/10, 1/5, 1/4, 1/3, 1/2, or 2/3 of the volume for the complete dissolution of the product in the heated condition.

The present invention also provides a naphthofuran compound prepared by the process of the present invention. In some embodiments, the naphthofuran compound is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In a further embodiment, the naphthofuran compound is prepared by the process including reacting the isolated crude product of the coupling of 2-hydroxy-1,4-naphthoquinone (4-4) and 3-Bromo-3-buten-2-one (4-3) with manganese dioxide in the presence of toluene. In an even further embodiment, the process further includes filtering the aged reaction mixture with a pad of activated carbon.

In another aspect, the present invention provides substantially pure naphthofuran compounds.

In some embodiments, the present invention provides a substantially pure compound selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof.

In some embodiments, the present invention provides a substantially pure compound of Formula II,

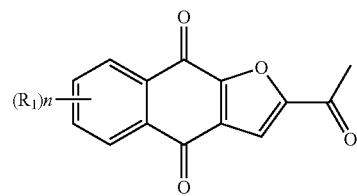

(II)

wherein each $R_1$ is independently H, Cl, or F; and n is 0, 1, 2, 3, or 4.

As used herein, "substantially pure" refers to a purity of at least about 80%. In some embodiments, the purity of a compound of the present invention has a purity of at least about 85%, about 90%, about 95%, or about 99%. In a further embodiment, the purity of a compound of the present invention has a purity of at least about 99.5%, or about 99.8%. In an even further embodiment, the purity of a compound of the present invention has a purity of at least about 99.85%, about 99.90%, about 99.94%, about 99.95%, or about 99.99%. In some embodiments, the compound of the present invention is selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof. In some embodiments, the compound of the present invention is a polymorph. In some embodiments, the compound of the present invention is a polymorph of a compound according to Formula I. In some embodiments, the compound of the present invention is a polymorph of Compound 1.

The typical impurities that may be present in a compound of the present invention include one or more selected from the group consisting of by-product, isomer, intermediate, and solvent. In some embodiments, the impurities that may be present in a compound of the present invention is at most about 10%, about 8%, about 5%, about 2%, or about 1% relative to the compound of Formula II. In a further embodiment, the impurities that may be present in a compound of the present invention is at most about 0.5%, about 0.2%, about 0.15%, or about 0.1% relative to the compound of Formula II. In an even further embodiment, the impurities that may be present in a compound of the present invention is at most about 0.05%, about 0.02%, or about 0.01% relative to the compound of Formula II. In some embodiments, the substantially pure compound of Formula II have at most about 500, 200, 100, 50, 20, 10, 5, 2, 1, 0.5, 0.2, 0.15, 0.1, or 0 parts per million (p.p.m.) of residual by-product or by-products relative to the compound of Formula II.

In some embodiments, the impurities include one or more by-products selected from the group consisting of 2-acetyl-2,3-dihydronaphtho[2,3-b]furan-4,9-dione, 2,6-Diacetyl-naphtho[2,3-b]furan-4,9-dione, 2,7-Diacetyl-naphtho[2,3-b]furan-4,9-dione, 3-Acetyl-naphtho[2,3-b]furan-4,9-dione, Naphtho[2,3-b]furan-4,9-dione, Naphtho[2,3-b]furan-4,9-dione, Naphtho[2,3-b]furan-4,9-diol, and 1-(4,9-Dihydroxy-naphtho[2,3-b]furan-2-yl)-ethanone.

In some embodiments, the impurities include manganese (Mn).

The purity of a compound of the present invention may be determined with various devices. In some embodiments, the purity is determined with HPLC (High Performance Liquid Chromatography). In some embodiments, the purity is determined with NMR (Nuclear Magnetic Resonance). In a further embodiment, the purity is determined with HPLC and NMR.

Figure 13:
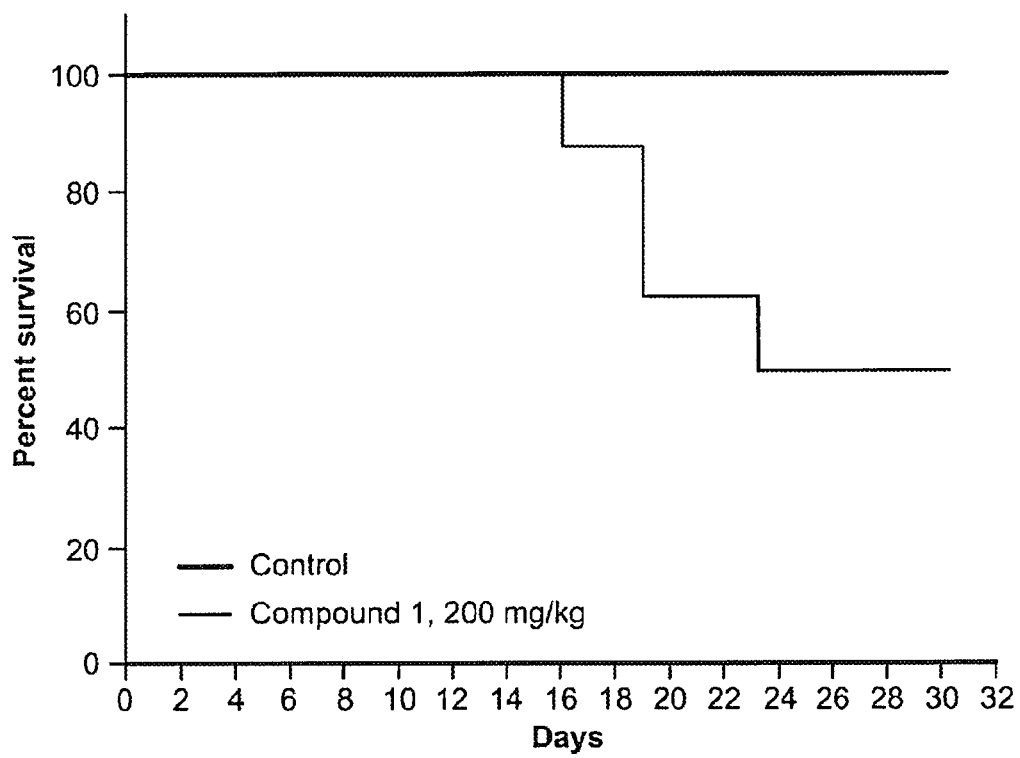
FIG. 13 is a graph depicting the toxicity observed with about 90% pure Crystal Form 2 produced using the synthetic process illustrated in FIGS. 5A-5B.
Figure 13:
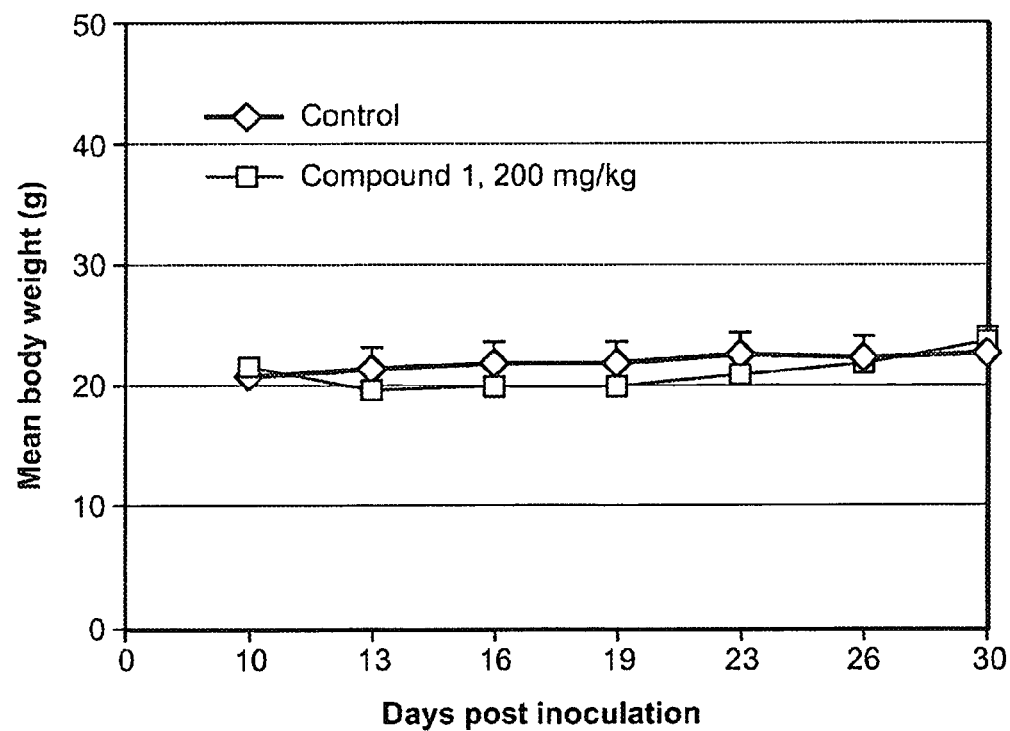
Figure 13:
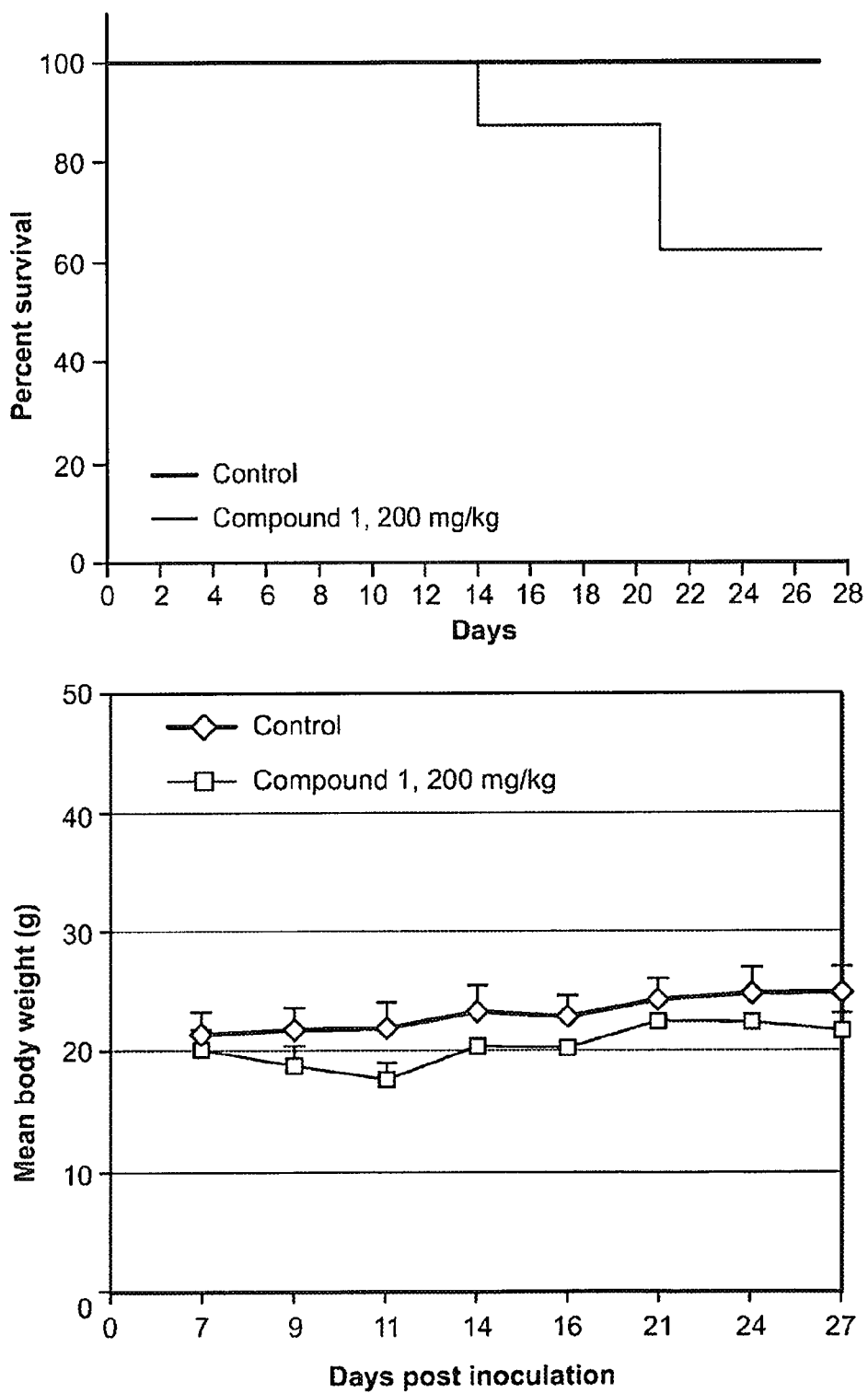
Figure 14:
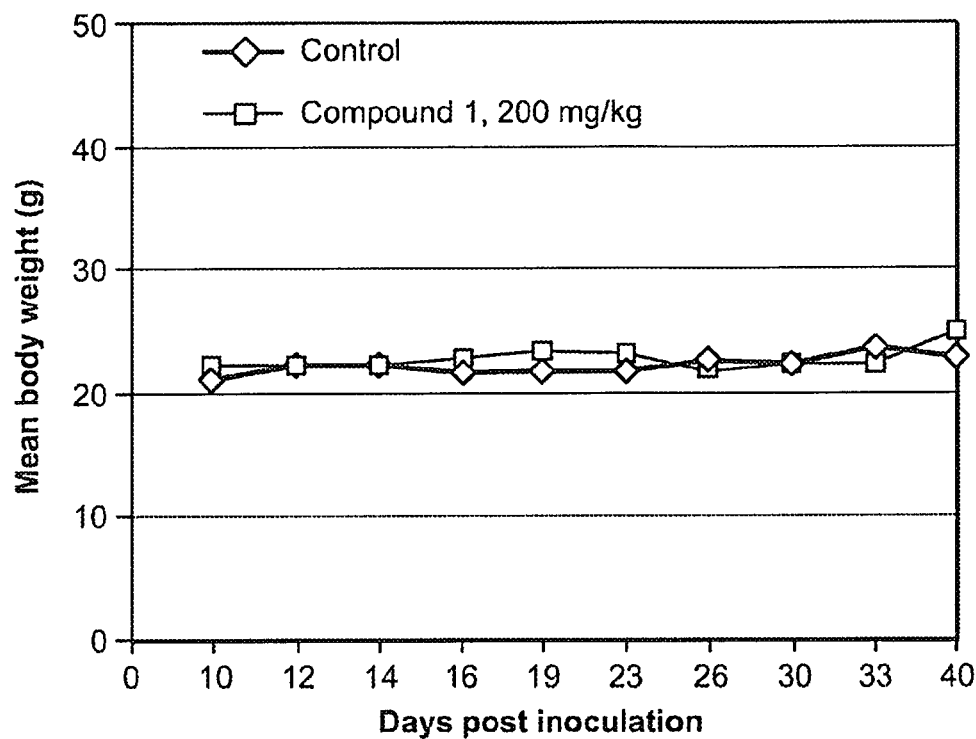
FIG. 14 is a graph depicting the safety of about 95% pure Crystal Form 2 produced using the synthetic process illustrated in FIGS. 5A-5B.
Figure 14:
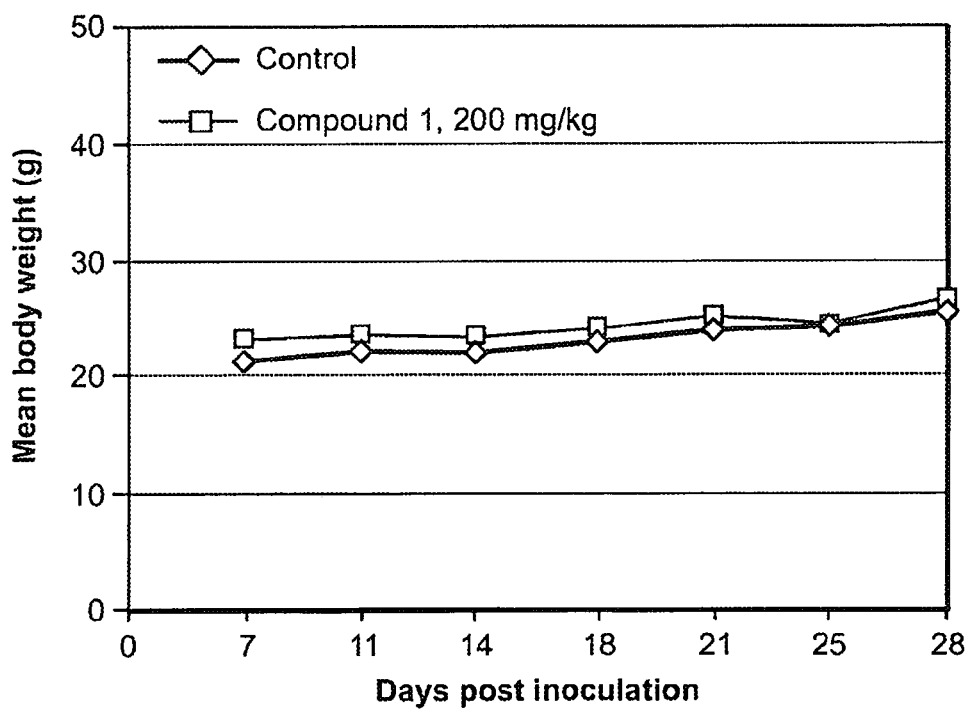

These highly pure compositions containing Compound 1 exhibit a significantly improved safety profile in animal experiments compared to less pure compositions that contain Compound 1. No signs of any adverse effects of highly pure Compound 1 have been observed in mice. In addition, these highly pure compositions containing Compound 1 have been tested in patients and have demonstrated exceptional safety. For example, FIG. 13 illustrates the toxicity observed with a composition with about 90% purity for Compound 1, while FIG. 14 illustrates that the highly pure compositions having about 95% or greater purity for Compound 1 are safe and effective. In the study shown in FIG. 13, immunosuppressed mice with established subcutaneous FaDu human head and neck cancer (upper panel) or MDA-231 human breast cancer (lower panel) were given indicated amount of Compound 1, or vehicle control orally (po). Compound 1 was formulated in GELUCIRE™. All regimens were administered daily (qd). Body weights were evaluated periodically during treatment. Each point represents the mean±SEM of eight tumors. Significant toxicity was observed with about 90% pure Compound 1. A total of 4 mice died during the treatment in the first experiment (upper panel) (one on day 16, 2 on day 19, and 1 on day 23), and their body weights were, therefore, not included in the plot after their death. A total of 3 mice died during the treatment in the second experiment (lower panel) (1 on day 14 and 2 on day 21), and their body weights were, therefore, not included in the plot after their death. In the study shown in FIG. 14, immunosuppressed mice with established subcutaneous FaDu human head and neck cancer (upper panel) or MDA-231 human breast cancer (lower panel) were given indicated amount of Compound 1, or vehicle control orally (po). Compound 1 was formulated in GELUCIRE™. All regimens were administered daily (qd). Body weights were evaluated periodically during treatment. Each point represents the mean±SEM of eight tumors. Compound 1 with higher purity was well-tolerated and showed no signs of toxicity. All mice remained healthy throughout the treatment in both experiments. In a Phase I study, the dose of Compound 1 was escalated from 20 mg to 2000 mg/day, and a maximum tolerated dose (MTD) not reached. No dose-limiting toxicity was observed. Patients tolerated Compound 1 very well without drug-induced adverse effects, which is in sharp contrast to cancer chemotherapeutics. The clinical safety profile of the substantially pure compositions of Compound 1 is among the best for oncology drugs in history.

Pharmaceutical Formulations

Certain excipients or enhancers were found to enhance the oral bioavailability of particles of a compound according to Formula I of a given particle size distribution in a pharmaceutical formulation. For example, the addition of the pharmaceutically compatible excipient GELUCIRE™ 44/14 (a polyethylene glycol glyceryl laurate produced by Gattefossé) can increase the bioavailability of Compound 1 having a median particle size of less than or equal to about 20 microns. Examples of other excipients than can be used to enhance or control oral bioavailability include surfactants, such as TWEEN 80™ or TWEEN20™ (a polysorbate, i.e., a polyoxyethylene sorbitan monolaurate) or certain lipids, such as phosphatidylcholines, e.g., dimyristoylphosphatidylcholine (DMPC). Surfactants include compounds that are amphiphilic and contain both hydrophobic and hydrophilic groups. Other excipients can include, for example, a glycerol ester of a fatty acid, a glycerol ester of a saturated fatty acid, a glycerol ester of a saturated fatty acid having from 8 to 18 carbons, glyceryl laurate, polyethylene glycol, a polyoxyethylene sorbitan alkylate, cellulose or cellulose derivatives, such as microcrystalline cellulose and carboxymethyl cellulose (CMC), as well as lipids, such as sterols, e.g., cholesterol. Other excipients can include antioxidants, such as Vitamin E. Other excipients and additional components can be included in a pharmaceutical formulation according to the present invention, as will be appreciated by one of skill in the art. For example, other active agents, standard vehicles, carriers, liquid carriers, saline, aqueous solutions, diluents, surface active agents, dispersing agents, inert diluents, granulating and disintegrating agents, binding agents, lubricating agents, glidants, discharging agents, sweetening agents, flavoring agents, coloring agents, preservatives, physiologically degradable compositions such as gelatin, aqueous vehicles and solvents, oily vehicles and solvents, suspending agents, dispersing or wetting agents, suspending agents, emulsifying agents, demulcents, buffers, salts, thickening agents, gelatins, fillers, emulsifying agents, antioxidants, antibiotics, antifungal agents, stabilizing agents, water, glycols, oils, alcohols, crystallization retarding agents (e.g., to retard crystallization of a sugar), starches, sugars, sucrose, surface active agents, agents to increase the solubility of any other ingredient, such as a polyhydroxy alcohol, for example glycerol or sorbitol, pharmaceutically acceptable polymeric or hydrophobic materials, and other components can be included. The appropriate additional agent or agents to add will depend on the dosage form (e.g., injectable solution, capsule, or pill), as will be appreciated by one skilled in the art.

The compound according to Formula I of the present invention may be formulated into "pharmaceutical compositions". Embodiments according to the present invention include various dosage forms including a compound, which can be useful, for example, for treating a patient. For example, oral dosage forms can include a tablet, pill, capsule (hard or soft), caplet, powder, granule, suspension (e.g., in an aqueous or oily vehicle), solution (e.g., in an aqueous or oily vehicle), gel, cachet, troche, lozenge, syrup, elixir, emulsion, draught, oil-in-water emulsion, or a water-in-oil emulsion. Because of their ease in administration, tablets and capsules may represent a preferred oral dosage. Solid oral dosage forms may be sugar coated or enteric coated by standard techniques. For example, nasal and other mucosal spray formulations (e.g. inhalable forms) can include purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier, of an inhalant, or of an aerosol. Such formulations may be delivered by any suitable means or method, e.g., by nebulizer, atomizer, metered dose inhaler, or the like. For example, a pharmaceutical composition according to the present invention may be administered topically, for example, in the form of an ointment, cream, or suppository. For example, a pharmaceutical composition according to the present invention may be administered by injecting an injectant. Thus, a dosage form according to the present invention can have, for example, a solid, semi-solid, liquid, or gaseous form. Suitable dosage forms include but are not limited to oral, rectal, sub-lingual, mucosal, nasal, ophthalmic, subcutaneous, intramuscular, intravenous, parenteral, transdermal, spinal, intrathecal, intra-articular, sub-arterial, sub-arachnoid, bronchial, lymphatic, and intra-uterile administration, and other dosage forms for systemic delivery of active ingredients. An active ingredient, for example, a compound according to Formula I may be contained in a formulation that provides quick release, sustained release, delayed release, or any other release profile known to one skilled in the art after administration to a subject (patient). The mode of administration and dosage form selected for a given treatment is closely related to the therapeutic amounts of the compounds or compositions which are desirable and efficacious for the given treatment application as well as factors such as the mental state and physical condition of the subject (patient).

A pharmaceutical composition of the invention may be prepared, packaged, or sold in bulk, as a single unit dose, as a plurality of single unit doses, or in a multi-dose form. As used herein, a "unit dose" is a discrete amount of the pharmaceutical composition including a predetermined amount of the active ingredient. The amount of the active ingredient in each unit dose is generally equal to the total amount of the active ingredient that would be administered or a convenient fraction of a total dosage amount such as, for example, one-half or one-third of such a dosage. A formulation of a pharmaceutical composition of the invention suitable for oral administration may be in the form of a discrete solid dosage unit. Each solid dosage unit contains a predetermined amount of the active ingredient, for example a unit dose or fraction thereof. As used herein, an "oily" liquid is one which includes a carbon or silicon based liquid that is less polar than water. In such pharmaceutical dosage forms, the active agent preferably is utilized together with one or more pharmaceutically acceptable carrier(s) therefore and optionally any other therapeutic ingredients. The carriers) must be pharmaceutically acceptable in the sense of being compatible with the other ingredients of the formulation and not unduly deleterious to the recipient thereof. The compositions of the present invention can be provided in unit dosage form, wherein each dosage unit, e.g., a teaspoon, tablet, capsule, solution, or suppository, contains a predetermined amount of the active drug or prodrug, alone or in appropriate combination with other pharmaceutically-active agents. The term "unit dosage form" refers to physically discrete units suitable as unitary dosages for human and animal subjects, each unit containing a predetermined quantity of the composition of the present invention, alone or in combination with other active agents, calculated in an amount sufficient to produce the desired effect.

Dosage forms of the present pharmaceutical composition can be prepared by techniques known in the art and contain a therapeutically effective amount of an active compound or ingredient. Any technique known or hereafter developed may be used for the preparation of pharmaceutical compositions or formulations according to the invention. In general, preparation includes bringing the active ingredient into association with a carrier or one or more other additional components, and then, if necessary or desirable, shaping or packaging the product into a desired single- or multi-dose unit. Powdered and granular formulations according to the invention may be prepared using known methods or methods to be developed. Such formulations may be administered directly to a subject, or used, for example, to form tablets, fill capsules, or prepare an aqueous or oily suspension or solution by addition of an aqueous or oily vehicle thereto. A tablet may be made by compression or molding, or by wet granulation, optionally with one or more accessory ingredients. Compressed tablets may be prepared by compressing, in a suitable device, the active ingredient in a free-flowing form such as a powder or granular preparation. Molded tablets may be made by molding, in a suitable device, a mixture of the active ingredient, a pharmaceutically acceptable carrier, and at least sufficient liquid to moisten the mixture. Tablets may be non-coated, or they may be coated using methods known in the art or methods to be developed. Coated tablets may be formulated for delayed disintegration in the gastrointestinal tract of a subject, for example, by use of an enteric coating, thereby providing sustained release and absorption of the active ingredient. Tablets may further include ingredients to provide a pharmaceutically elegant and palatable preparation. Hard capsules including the active ingredient may be made using a physiologically degradable composition, such as gelatin. Such hard capsules include the active ingredient. Soft gelatin capsules including the active ingredient may be made using a physiologically degradable composition, such as gelatin. Such soft capsules include the active ingredient, which may be mixed with water or an oil medium. Liquid formulations of a pharmaceutical composition of the invention that are suitable for administration may be prepared, packaged, and sold either in liquid form or in the form of a dry product intended for reconstitution with water or another suitable vehicle prior to use. Liquid suspensions, in which the active ingredient is dispersed in an aqueous or oily vehicle, and liquid solutions, in which the active ingredient is dissolved in an aqueous or oily vehicle, may be prepared using conventional methods or methods to be developed. Liquid suspension of the active ingredient may be in an aqueous or oily vehicle. Liquid solutions of the active ingredient may be in an aqueous or oily vehicle. To prepare such pharmaceutical dosage forms, an active ingredient, e.g., a naphthofuran, can be intimately admixed with a pharmaceutical carrier according to conventional pharmaceutical compounding techniques. The carrier may take a wide variety of forms depending on the form of preparation desired for administration. In preparing the compositions in oral dosage form, any of the usual pharmaceutical media may be employed.

In some embodiments according to the present invention, an item of manufacture includes a container containing a therapeutically effective amount of a pharmaceutical composition including a compound according to Formula I. The container can include a pharmaceutically acceptable excipient. The container can include printed labeling instructions. For example, the printed labeling can indicate the dosage and frequency with which the pharmaceutical composition should be administered, and whether the composition should be administered with food or within a defined period of time before or after ingestion of food. The composition can be contained in any suitable container capable of holding and dispensing the dosage form that will not significantly interact with the composition. The labeling instructions can be consistent with the methods of treatment described herein. The labeling can be associated with the container by a means that maintains a physical proximity of the two. By way of non-limiting example, the container and the labeling may both be contained in a packaging material such as a box or plastic shrink wrap or may be associated with the instructions being bonded to the container such as with glue that does not obscure the labeling instructions or other bonding or holding means.

Processes for Making Pharmaceutical Formulations Having Selected Particle Size Distribution and Identifying an Optimum Particle Size Distribution Milling Processes In a method according to the present invention, a milling or grinding process can be used to reduce the size of particles of an active ingredient or compound according to Formula I. For example, a milling or grinding process can be suitable for producing particles having a median size of 200 µm, 150 µm, 100 µm, 40 µm, 20 µm, 5 µm, 2 µm or greater or lesser size. Such a milling or grinding process can include, for example, ball milling, roll milling, jet milling, wet milling, ultrasonic milling, grinding, and combinations. For example, the process can reduce particle size by impacting particles with a hard surface, or by subjecting the particles to high pressure, e.g., squeezing a particle between two surfaces. For example, in jet milling, a stream of gas entrains particles and accelerates them to high velocities. The particles then impact other particles and walls and fracture into smaller particles. For example, in wet milling, particles are combined with a liquid, and the resultant slurry is passed through a high shear mixer to fracture the particles. For example, in ultrasonic milling, particles, for example, in a slurry, are exposed to ultrasonic radiation. Cavitation induced by the ultrasound can fracture the particles into particles of smaller size.

It can be advantageous to lower the temperature of the particles prior to subjecting them to the milling or grinding operation. For example, the temperature can be lowered to a cryogenic temperature, e.g., by exposing the particles to or immersing the particles in a cryogenic fluid, such as liquid nitrogen. Such lowering of the temperature can render the particles more brittle and more susceptible to having their size reduced in the milling or grinding operation. Subsequent to the milling or grinding process, a selection process, such as sieving, can be used to narrow the range of particle sizes.

Crystallizing Process

Crystallization is the main separation and purification step for the manufacturing of drug substances. Crystallization can also be utilized to control particle size. The particle size distribution (PSD) obtained during crystallization is influenced by a combination of various mechanisms that occur during crystallization, such as nucleation, growth, aggregation, attrition, breakage, etc. Control of PSD during crystallization is critical to achieving the desired product properties. When the particle size cannot be consistently controlled during crystallization to meet the desired specifications, an extra processing step such as dry milling can be included. (Braat, et al *Crystallization: Particle Size Control, Encyclopedia of Pharmaceutical Technology: Third Edition*, Published on 2 Oct. 2006)

Methods for Treatment of Cancer

A method according to the present invention for treating, delaying the progression of, preventing a relapse of, alleviating a symptom of, or otherwise ameliorating a human, mammal, or animal subject afflicted with a neoplasm includes administering a therapeutically effective amount of a pharmaceutical composition including particles of a predetermined size distribution, for example, a compound according to Formula I such as Compound 1, a pure compound, a pure product and/or a pure pharmaceutical composition, so that the volume growth of the neoplasm is slowed, the volume growth of the neoplasm is stopped, the neoplasm decreases in volume, and/or a cancerous neoplasm is killed. A few examples of types of neoplasms that may be amenable to treatment by this method include solid tumors, malignant tumors, cancers, metastatic tumors, neoplasms including cancer stem cells, neoplasms in which the STAT3 pathway is implicated, carcinomas, and sarcomas. A non-exhaustive list of cancers that may be amenable to treatment by administration of particles of a compound according to Formula I include the following: breast cancer, head and neck cancer, lung cancer, ovarian cancer, pancreatic cancer, colorectal carcinoma, prostate cancer, melanoma, sarcoma, liver cancer, brain tumor, leukemia, multiple myeloma, gastric cancer, and lymphoma. The STAT3 pathway may be implicated in these cancers. A non-exhaustive list of cancers that may be amenable to treatment by administration of particles of, for example, a compound according to Formula I include the following: colorectal cancer, breast cancer, ovarian cancer, lung cancer, melanoma and medulloblastoma. The CSC pathway may be implicated in these cancers. A non-exhaustive list of other cancers that may be amenable to treatment by administration of particles of, for example, a compound according to Formula I include the following: lung cancer, cervical cancer, renal cell carcinoma, hepatocellular carcinoma, esophageal cancer, glioma, bladder cancer, colorectal cancer, breast cancer, prostate cancer, pancreatic cancer, endometrial cancer, thyroid cancer, bile duct cancer, bone cancer, eye cancer (retinoblastoma), gallbladder cancer, pituitary cancer, rectal cancer, salivary gland cancer, and nasal pharyngeal cancer.

Cancer Stem Cells

In recent years, a new model of tumorigenesis has gained wide acceptance, where it is hypothesized that only a small fraction of the entire tumor mass are responsible for the tumorigenic activities within the tumor, whereas the old or clonal genetic model posits that all the mutated tumor cells contribute equally to such tumorigenic activities. This small fraction of tumorigenic cells, according to the new model, are transformed cells with stem-cell-like qualities and are called "cancer stem cells" (CSCs). Bonnet and Dick first demonstrated, in vivo, the presence of CSCs in acute myeloid leukemia (AML) during the 1990s. Their data showed that only a small subpopulation of human AML cells had the ability to transfer AML when transplanted into immunodeficient mice while other AML cells were incapable of inducing leukemia. Later, these CSCs were shown to have the same cellular markers, $CD34^+/CD38^-$, as primitive hematopoietic stem cells. (Bonnet, D., *Normal and leukemic stem cells*. Br J Haematol, 2005. 130(4): p. 469-79). Since then, researchers have found CSCs conclusively in various types of tumors including those of the brain, breast, skin, prostate, colorectal cancer, and so on.

The CSC model of tumorigenesis would explain why tens or hundreds of thousands of tumor cells need to be injected into an experimental animal in order to establish a tumor transplant. In human AML, the frequency of these cells is less than 1 in 10,000. (Bonnet, D. and J. E. Dick, *Human acute myeloid leukemia is organized as a hierarchy that originates from a primitive hematopoietic cell*. Nat Med, 1997. 3(7): p. 730-7). Even though rare within a given tumor cell population, there is mounting evidence that such cells exist in almost all tumor types. However, as cancer cell lines are selected from a sub-population of cancer cells that are specifically adapted to grow in tissue culture, the biological and functional properties of cancer cell lines can undergo dramatic changes. Therefore, not all cancer cell lines contain CSCs.

Cancer stem cells share many similar traits with normal stem cells. For example, CSCs have self-renewal capacity, namely, the ability to give rise to additional tumorigenic cancer stem cells, typically at a slower rate than other dividing tumor cells, as opposed to a limited number of divisions. CSCs also have the ability to differentiate into multiple cell types, which would explain histological evidence that not only many tumors contain multiple cell types native to the host organ, but also that heterogeneity is commonly retained in tumor metastases. CSCs have been demonstrated to be fundamentally responsible for tumorigenesis, cancer metastasis, and cancer reoccurrence. CSCs are also called tumor initiating cells, cancer stem-like cells, stem-like cancer cells, highly tumorigenic cells, tumor stem cells, solid tumor stem cells, or super malignant cells.

The existence of cancer stem cells has fundamental implications for future cancer treatments and therapies. These implications are manifested in disease identification, selective drug targeting, prevention of cancer metastasis and recurrence, and development of new strategies in fighting cancer.

The efficacy of current cancer treatments are, in the initial stages of testing, often measured by the size of the tumor shrinkage, i.e., the amount of tumor mass that is killed off. As CSCs would form a very small proportion of the tumor and have markedly different biologic characteristics than their more differentiated progenies, the measurement of tumor mass may not necessarily select for drugs that act specifically on the stem cells. In fact, cancer stem cells appear to be resistant to radiotherapy (XRT) and also refractory to chemotherapeutic and targeted drugs. (Hambardzumyan, D., M. Squatrito, and E. C. Holland, Radiation resistance and stem-like cells in brain tumors. Cancer Cell, 2006. 10(6): p. 454-6; Baumann, M., M. Krause, and R. Hill, Exploring the role of cancer stem cells in radioresistance. Nat Rev Cancer, 2008. 8(7): p. 545-54; Ailles, L. E. and I. L. Weissman, Cancer stem cells in solid tumors. Curr Opin Biotechnol, 2007. 18(5): p. 460-6). Normal somatic stem cells are naturally resistant to chemotherapeutic agents— they have various pumps (such as MDR) that pump out drugs, and DNA repair proteins. Further, they also have a slow rate of cell turnover while chemotherapeutic agents target rapidly replicating cells. Cancer stem cells, being the mutated counterparts of normal stem cells, may also have similar mechanisms that allow them to survive drug therapies and radiation treatment. In other words, conventional chemotherapies and radiotherapies kill differentiated or differentiating cells, which form the bulk of the tumor that are unable to generate new highly tumorigenic cancer stem cells. The population of cancer stem cells that gave rise to the differentiated and differentiating cells, on the other hand, could remain untouched and cause a relapse of the disease. A further danger for conventional anti-cancer therapy is the possibility that chemotherapeutic treatment leaves only chemotherapy-resistant cancer stem cells, and the ensuing recurrent tumor will likely also be resistant to chemotherapy.

Since the surviving cancer stem cells can repopulate the tumor and cause relapse, it is imperative that anti-cancer therapies include strategies against CSCs (see FIG. 18). This is akin to eliminating the roots in order to prevent dandelions from regrowth even if the weed's ground level mass has been cut. (Jones, R. J., W. H. Matsui, and B. D. Smith, *Cancer stem cells: are we missing the target?* J Natl Cancer Inst, 2004. 96(8): p. 583-5). By selectively targeting cancer stem cells, it becomes possible to treat patients with aggressive, non-resectable tumors and refractory or recurrent cancers, as well as preventing the tumor metastasis and recurrence. Development of specific therapies targeting cancer stem cells may improve survival and the quality of life of cancer patients, especially for sufferers of metastatic cancers. The key to unlocking this untapped potential is the identification and validation of pathways that are selectively important for cancer stem cell self-renewal and survival. Unfortunately, though multiple pathways underlying tumorigenesis in cancer or self-renewal in embryonic and adult stem cells have been elucidated in the past, very few pathways have been identified and validated for cancer stem cell self-renewal and survival.

There has also been a lot of research into the identification and isolation of cancer stem cells. Methods used mainly exploit the ability of CSCs to efflux drugs, or are based on the expression of surface markers associated with cancer stem cells.

For example, since CSCs are resistant to many chemotherapeutic agents, it is not surprising that CSCs almost ubiquitously overexpress drug efflux pumps such as ABCG2 (BCRP-1) (Ho, M. M., et al., Side population in human lung cancer cell lines and tumors is enriched with stem-like cancer cells. Cancer Res, 2007. 67(10): p. 4827-33; Wang, J., et al., Identification of cancer stem cell-like side population cells in human nasopharyngeal carcinoma cell line. Cancer Res, 2007. 67(8): p. 3716-24; Haraguchi, N., et al., Characterization of a side population of cancer cells from human gastrointestinal system. Stem Cells, 2006. 24(3): p. 506-13; Doyle, L. A. and D. D. Ross, Multidrug resistance mediated by the breast cancer resistance protein BCRP (ABCG2). Oncogene, 2003. 22(47): p. 7340-58; Alvi, A. J., et al., Functional and molecular characterisation of mammary side population cells. Breast Cancer Res, 2003. 5(1): p. R1-8), and other ATP binding cassette (ABC) superfamily members (Frank, N.Y., et al., ABCB5-mediated doxorubicin transport and chemoresistance in human malignant melanoma. Cancer Res, 2005. 65(10): p. 4320-33; Schatton, T., et al., Identification of cells initiating human melanomas. Nature, 2008. 451(7176): p. 345-9). Accordingly, the side population (SP) technique, originally used to enrich hematopoietic and leukemic stem cells, was also employed to identify and isolate CSCs. (Kondo, T., T. Setoguchi, and T. Taga, *Persistence of a small subpopulation of cancer stem-like cells in the C6 glioma cell line*. Proc Natl Acad Sci USA, 2004. 101(3): p. 781-6). This technique, first described by Goodell et al., takes advantage of differential ABC transporter-dependent efflux of fluorescent dyes such as Hoechst 33342 to define and isolate a cell population enriched in CSCs (Doyle, L. A. and D. D. Ross, *Multidrug resistance mediated by the breast cancer resistance protein BCRP (ABCG2)*. Oncogene, 2003. 22(47): p. 7340-58; Goodell, M. A., et al., *Isolation and functional properties of murine hematopoietic stem cells that are replicating in vivo*. J Exp Med, 1996. 183(4): p. 1797-806). Specifically, the SP is revealed by blocking drug efflux with verapamil, at which point the dyes can no longer be pumped out of the SP.

Researchers have also focused on finding specific markers that distinguish cancer stem cells from the bulk of the tumor. Most commonly expressed surface markers by the cancer stem cells include CD44, CD133, and CD166. (Collins, A. T., et al., Prospective identification of tumorigenic prostate cancer stem cells. Cancer Res, 2005. 65(23): p. 10946-51; Li, C., et al., Identification of pancreatic cancer stem cells. Cancer Res, 2007. 67(3): p. 1030-7; Ma, S., et al., Identification and characterization of tumorigenic liver cancer stem/progenitor cells. Gastroenterology, 2007. 132(7): p. 2542-56; Prince, M. E., et al., Identification of a subpopulation of cells with cancer stem cell properties in head and neck squamous cell carcinoma. Proc Natl Acad Sci USA, 2007. 104(3): p. 973-8; Ricci-Vitiani, L., et al., Identification and expansion of human colon-cancer-initiating cells. Nature, 2007. 445(7123): p. 111-5; Singh, S. K., et al., Identification of a cancer stem cell in human brain tumors. Cancer Res, 2003. 63(18): p. 5821-8; Dalerba, P., et al., Phenotypic characterization of human colorectal cancer stem cells. Proc Natl Acad Sci USA, 2007. 104(24): p. 10158-63). Sorting tumor cells based primarily upon the differential expression of these surface marker(s) have accounted for the majority of the highly tumorigenic CSCs described to date. Therefore, these surface markers are well validated for identification and isolation of cancer stem cells from the cancer cell lines and from the bulk of tumor tissues.

Recent studies have uncovered the presence of cancer stem cells (CSCs) with an exclusive ability to regenerate tumors. These CSCs exist in almost all tumor types and are functionally linked with continued malignant growth, cancer metastasis, recurrence, and cancer drug resistance. CSCs and their more differentiated progenies appear to have markedly different biologic characteristics. Conventional cancer drug screenings depend on measurement of the amount of tumor mass, therefore, they may not necessarily select for drugs that act specifically on the CSCs. In fact, CSCs have been demonstrated to resistant to standard chemotherapies and radiotherapy, and to becoming enriched after standard anti-cancer treatments, which result in cancer refractory and recurrence. Methods of isolating these cells include but not limited to identification by their ability of efflux Hoechst 33342, identification by the surface markers these cells express, such as CD133, CD44, CD166, and others, and enrichment by their tumorigenic property. The mounting evidence linking cancer stem cells to tumorigenesis unravel enormous therapeutic opportunity of targeting cancer stem cells.

The data provided herein, combined with recent breakthroughs in CSC research, allows the present invention to provide an array of methods directed at inhibiting CSCs, methods directed at inhibiting both CSCs and heterogeneous cancer cells, and methods of treating cancers that have CSCs in specific or cancers in general. The present invention also provides related methods (e.g., manufacturing and drug candidate screening), materials, compositions and kits. The method can prevent the CSCs from self-renewal, such that it is no longer able to replenish its numbers by dividing into tumorigenic CSC cells. Or, the method can induce cell death in CSCs, or in both CSCs and heterogeneous cancer cells. This method can be used to treat a subject's cancer. Cancers that are good candidates for such treatment include but are not limited to: breast cancer, head and neck cancer, lung cancer, ovarian cancer, pancreatic cancer, colorectal carcinoma, prostate cancer, renal cell carcinoma, melanoma, hepatocellular carcinomas, cervical cancer, sarcomas, brain tumors, gastric cancers, multiple myeloma, leukemia, and lymphomas. In some embodiments, the method is used to treat liver cancers, head and neck cancers, pancreatic cancers, and/or gastric cancers. In some embodiments, the method is used to treat multiple myeloma, brain tumors, and sarcomas.

Further, as CSCs have been demonstrated to be fundamentally responsible for tumorigenesis, cancer metastasis and cancer reoccurrence, any methods of the invention directed to inhibiting CSCs, or both CSCs and heterogeneous cancer cells, can be practiced to treat cancer that is metastatic, refractory to a chemotherapy or radiotherapy, or has relapsed in the subject after an initial treatment.

Figure 2:
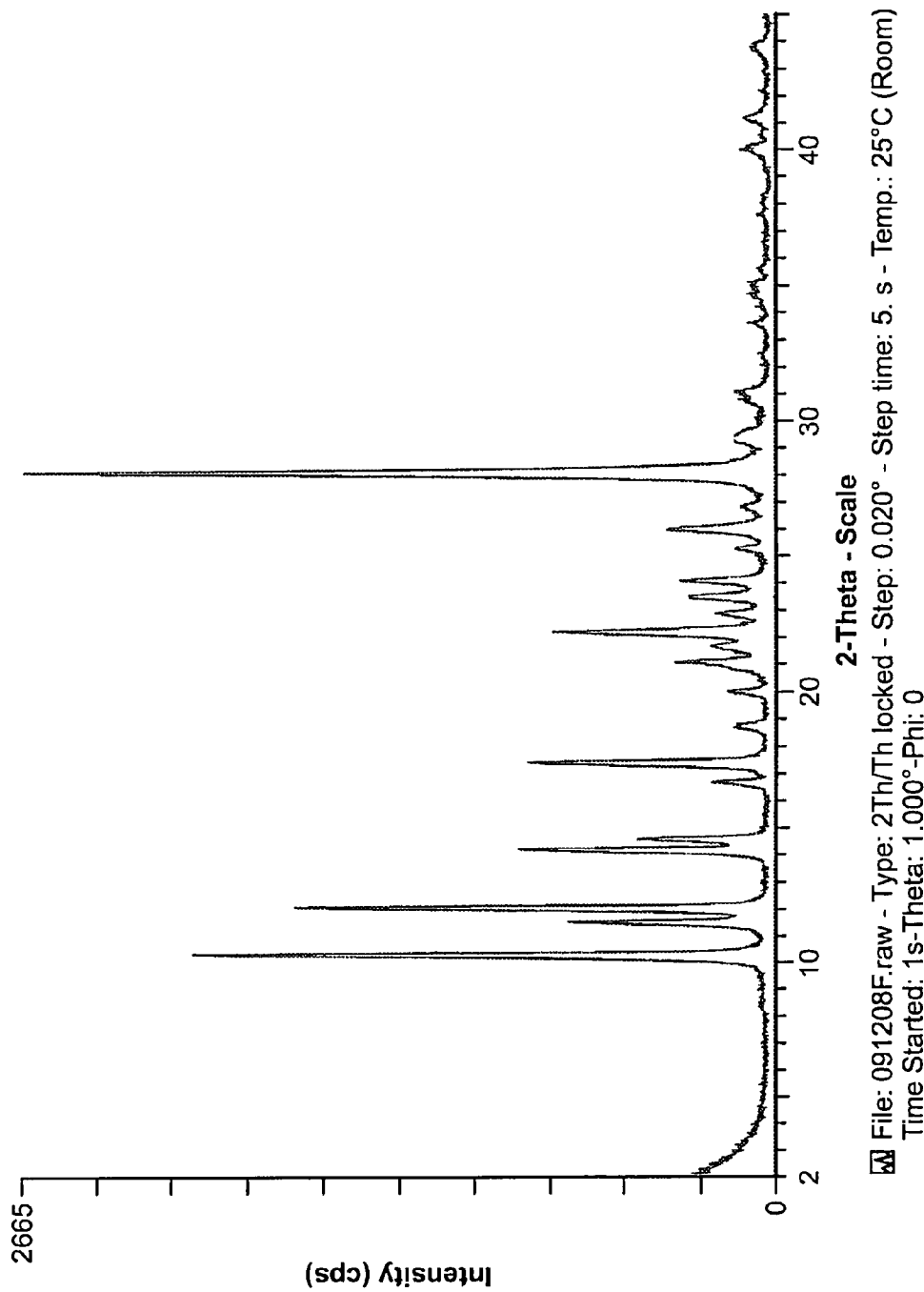
FIG. 2 is an illustration depicting XRPD Data of Crystal Form 2.
Figure 3:
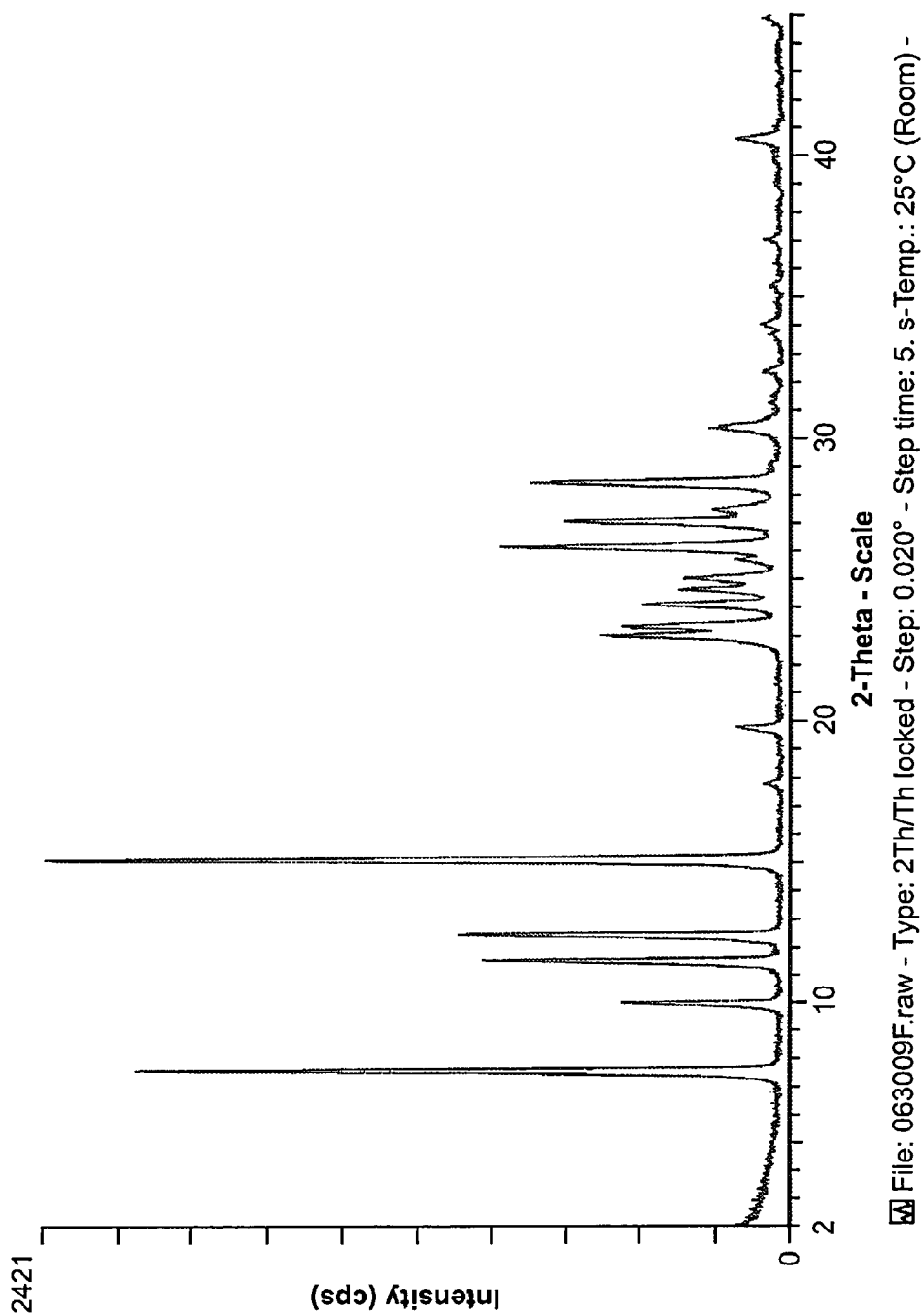
FIG. 3 is an illustration depicting XRPD Data of Crystal Form 3.
Figure 4:
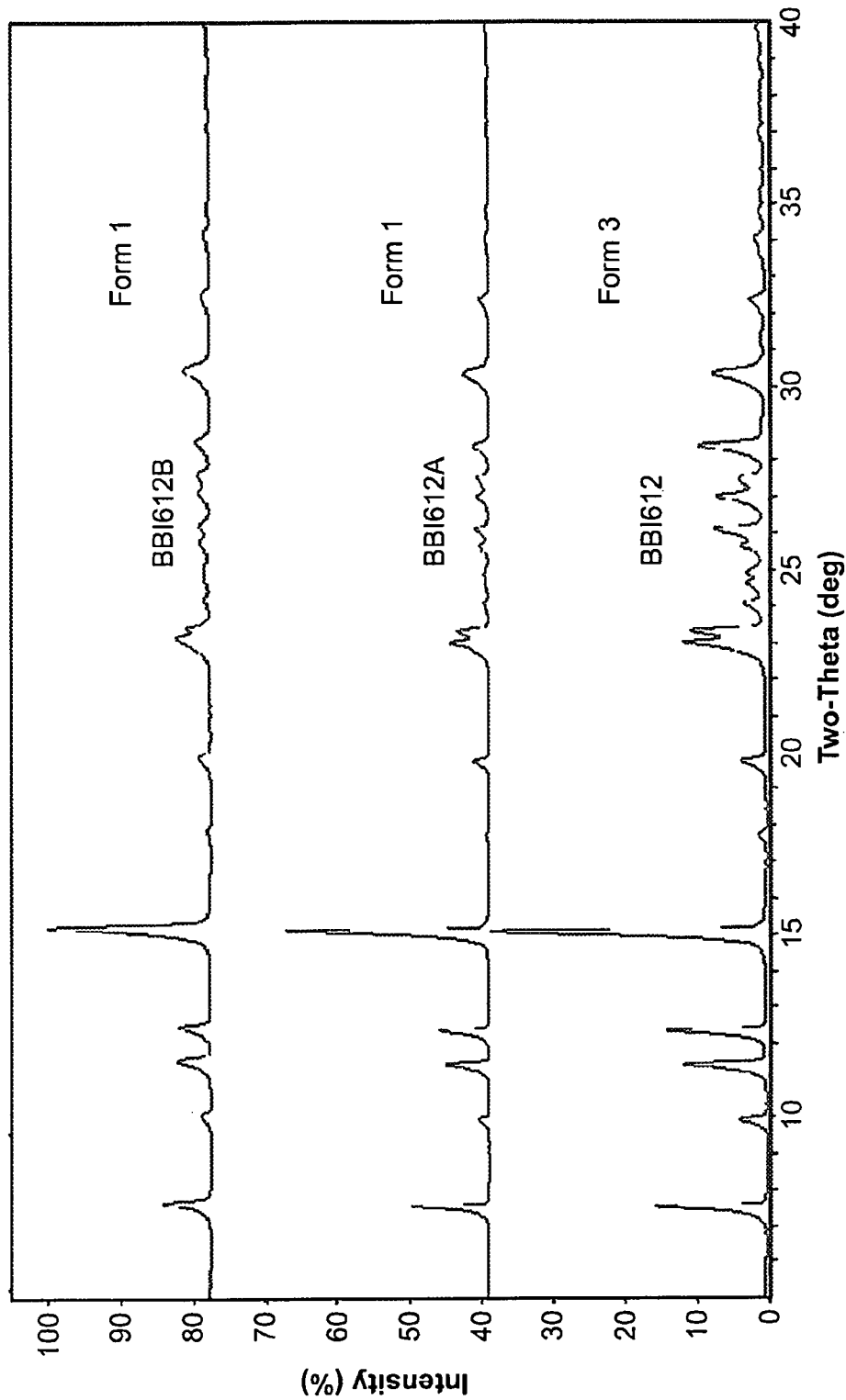
FIG. 4 is an illustration depicting the comparison of XRPD Data of Crystal Form 1 and Crystal Form 3.

In some embodiments, the cancer stem cell inhibitor according to the present invention is: a compound of Formula I, Compound 1, a polymorph of Compound 1, a polymorph of 2-acetyl-4H, 9H-naphtho[2,3-b]furan-4,9-dione characterized by an X-ray diffraction pattern substantially similar to that set forth in FIG. 1, a polymorph of 2-acetyl-4H, 9H-naphtho[2,3-b]furan-4,9-dione characterized by an X-ray diffraction pattern substantially similar to that set forth in FIG. 2, a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof, a polymorph of 2-acetyl-4H, 9H-naphtho[2,3-b]furan-4,9-dione characterized by an X-ray diffraction pattern substantially similar to that set forth in FIG. 3, a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 12.3 degrees 2θ, a peak at least at about 15 degrees 2θ, a peak at least at about 23 degrees 2θ, a peak at least at about 23.3 degrees 2θ, a peak at least at about 24.6 degrees 2θ, and a peak at least at about 28.4 degrees 2θ and any combinations thereof, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof; a polymorph of a compound of Formula I, Compound 1, a polymorph of Compound 1, a polymorph of 2-acetyl-4H, 9H-naphtho[2,3-b]furan-4,9-dione characterized by an X-ray diffraction pattern substantially similar to that set forth in FIG. 1, a polymorph of 2-acetyl-4H, 9H-naphtho[2,3-b]furan-4,9-dione characterized by an X-ray diffraction pattern substantially similar to that set forth in FIG. 2, a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof, a polymorph of 2-acetyl-4H, 9H-naphtho[2,3-b]furan-4,9-dione characterized by an X-ray diffraction pattern substantially similar to that set forth in FIG. 3, a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 12.3 degrees 2θ, a peak at least at about 15 degrees 2θ, a peak at least at about 23 degrees 2θ, a peak at least at about 23.3 degrees 2θ, a peak at least at about 24.6 degrees 2θ, and a peak at least at about 28.4 degrees 2θ and any combinations thereof, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof; or a substantially pure form of a compound of Formula I, Compound 1, a polymorph of Compound 1, a polymorph of 2-acetyl-4H, 9H-naphtho[2,3-b]furan-4,9-dione characterized by an X-ray diffraction pattern substantially similar to that set forth in FIG. 1, a polymorph of 2-acetyl-4H, 9H-naphtho[2,3-b]furan-4,9-dione characterized by an X-ray diffraction pattern substantially similar to that set forth in FIG. 2, a polymorph of 2-acetyl-4H, 9H-naphtho[2,3-b]furan-4,9-dione characterized by an X-ray diffraction pattern including two or more peaks from a peak at least at about 10.2 degrees 2θ, a peak at least at about 11.9 degrees 2θ, a peak at least at about 14.1 degrees 2θ, a peak at least at about 14.5 degrees 2θ, a peak at least at about 17.3 degrees 2θ, a peak at least at about 22.2 degrees 2θ, and a peak at least at about 28.1 degrees 2θ and any combinations thereof, a polymorph of 2-acetyl-4H, 9H-naphtho[2,3-b]furan-4,9-dione characterized by an X-ray diffraction pattern substantially similar to that set forth in FIG. 3, a polymorph of 2-acetyl-4H, 9H-naphtho[2,3-b]furan-4,9-dione characterized by an X-ray diffraction pattern including two or more peaks from a peak at least at about 7.5 degrees 2θ, a peak at least at about 9.9 degrees 2θ, a peak at least at about 12.3 degrees 2θ, a peak at least at about 15 degrees 2θ, a peak at least at about 23 degrees 2θ, a peak at least at about 23.3 degrees 2θ, a peak at least at about 24.6 degrees 2θ, and a peak at least at about 28.4 degrees 2θ and any combinations thereof, 2-(1-hydroxyethyl)-naphtho[2,3-b]furan-4,9-dione, 2-acetyl-7-chloronaphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof; a particle form of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof (also referred to herein as the "Compound of the Invention").

The present invention provides a method of identifying a drug candidate capable of inhibiting a cancer stem cell. In some embodiments, the drug candidate is capable of inducing cell death in CSC or at least inhibiting its self-renewal. In a further embodiment, the drug candidate is capable of inducing cell death in CSC or at least inhibiting its self-renewal, and inducing cell death in heterogeneous cancer cells. Various phases in the pathway can be targeted for screening the drug candidate.

Accordingly, in another aspect, the Compound of the Invention can be used to formulate a pharmaceutical composition to treat or prevent disorders or conditions. Some of the disorders include but are not limited to: autoimmune diseases, inflammatory diseases, inflammatory bowel diseases, arthritis, autoimmune demyelination disorder, Alzheimer's disease, stroke, ischemia reperfusion injury and multiple sclerosis. Some of the disorders are cancers and include but are not limited to: various types of breast cancers, head and neck cancers, lung cancers, ovarian cancers, pancreatic cancers, colorectal carcinoma, prostate cancers, renal cell carcinoma, melanoma, hepatocellular carcinomas, cervical cancers, sarcomas, brain tumors, gastric cancers, multiple myeloma, leukemia, and lymphomas.

Accordingly, in an aspect, the present invention provides a method of inhibiting cancer stem cells where an effective amount of the Compound of the Invention is administered to the cells. Cancers known to have CSCs are good candidates for such treatments, and include but are not limited to: various types of breast cancers, head and neck cancers, lung cancers, ovarian cancers, pancreatic cancers, colorectal adenocarcinoma, prostate cancers, liver cancers, melanoma, multiple myeloma, brain tumors, sarcomas, medulloblastoma, and leukemia.

Further, as CSCs have been demonstrated to be fundamentally responsible for tumorigenesis, cancer metastasis and cancer reoccurrence, any methods of the invention directed to inhibiting CSCs can be practiced to treat cancer that is metastatic, refractory to a chemotherapy or radiotherapy, or has relapsed in the subject after an initial treatment.

In some embodiments of the method, the cancer being treated is selected from the following group: liver cancer, colon cancer, head and neck cancer, pancreatic cancer, gastric cancer, renal cancer, sarcoma, multiple myeloma, metastatic breast cancer, metastatic prostate cancer, leukemia, lymphoma, pancreatic esophageal cancer, brain tumor, glioma, bladder cancer, endometrial cancer, thyroid cancer, bile duct cancer, bone cancer, eye cancer (retinoblastoma), gallbladder cancer, pituitary cancer, rectal cancer, salivary gland cancer, and nasal pharyngeal cancer.

In an aspect, the present invention provides a method of treating cancer in a subject, where a therapeutically effective amount of a pharmaceutical composition including the Compound of the Invention is administered to the subject. The cancer may be metastatic. The subject may be a mammal, e.g., a human being.

Treatment by administration of particles of, for example, a compound according to Formula I to a subject (patient) suffering from a neoplasm may be indicated for the following conditions. The neoplasm may be refractory to treatment by chemotherapy, radiotherapy, or hormone therapy. The neoplasm may not be amenable to surgical resection. The neoplasm may have relapsed in the subject (patient). Cancer stem cells have been implicated in the relapse of neoplasms; killing the cancer stem cells or inhibiting their self-renewal by a method according to the present invention may prevent the neoplasm from regenerating itself. Treatment by administration of particles of naphthofuran may slow or stop the volume growth of a neoplasm or decrease the volume of a neoplasm by, for example, inducing the death of, inhibiting the growth and/or division of, and/or selectively killing neoplastic cells. For example, a treatment according to the present invention may induce cell death of a cell of the neoplasm. For example, the treatment may act to inhibit the STAT3 pathway of a neoplastic cell.

Treatment by administration of particles of, for example, a Compound of the Invention to a subject (patient) suffering from a neoplasm may be used to prevent relapse of a neoplasm and/or as an adjuvant therapy to surgical resection.

A pharmaceutical composition including particles of, for example, a Compound of the Invention may be administered orally, as this is a convenient form of treatment. For example, the pharmaceutical composition may be administered orally no more than four times per day. Alternatively, the pharmaceutical composition can be administered intravenously or intraperitoneally.

In a method according to the present invention, the therapeutically effective amount of the pharmaceutical composition including particles, polymorphs and/or purified forms of a Compound of the Invention can be a total daily dose in the range of from about 20 mg to about 2000 mg, about 100 mg to about 1500 mg, about 160 mg to about 1400 mg, or from about 180 mg to 1200 mg. In some embodiments, the therapeutically effective amount of the pharmaceutical composition including particles, polymorphs and/or purified forms of a Compound of the Invention is a total daily dose in the range of from about 200 mg to about 1500 mg, or from about 360 mg to 1200 mg. In some embodiments, the therapeutically effective amount of the pharmaceutical composition including particles, polymorphs and/or purified forms of a Compound of the Invention is a total daily dose in the range of from about 400 mg to about 1000 mg. In some embodiments, the therapeutically effective amount of the pharmaceutical composition including particles, polymorphs and/or purified forms of a Compound of the Invention is a total daily dose of about 1000 mg.

In some embodiments, the therapeutically effective amount of the pharmaceutical composition including particles, polymorphs and/or purified forms of a Compound of the Invention is administered in a single daily dose. For example, in some embodiments, the therapeutically effective amount of the pharmaceutical composition including particles, polymorphs and/or purified forms of a Compound of the Invention is administered in a single daily dose in a range of from about 20 mg QD to about 2000 mg QD. In some embodiments, the therapeutically effective amount of the pharmaceutical composition including particles, polymorphs and/or purified forms of a Compound of the Invention is administered in a single daily dose in a range of about 20 mg QD to about 1000 mg QD.

In some embodiments, the therapeutically effective amount of the pharmaceutical composition including particles, polymorphs and/or purified forms of a Compound of the Invention is administered in more than one daily dose. For example, in some embodiments, the therapeutically effective amount of the pharmaceutical composition including particles, polymorphs and/or purified forms of a Compound of the Invention is administered in two daily doses, where the total daily dose is in a range of from about 160 mg to 1400 mg. In some embodiments, the therapeutically effective amount of the pharmaceutical composition including particles, polymorphs and/or purified forms of a Compound of the Invention is administered in two daily doses, where the total daily dose is in a range of from about 320 mg to 1200 mg. In some embodiments, the therapeutically effective amount of the pharmaceutical composition including particles, polymorphs and/or purified forms of a Compound of the Invention is administered in two daily doses, where the total daily dose is in a range of from about 400 mg to 1000 mg. In some embodiments, the therapeutically effective amount of the pharmaceutical composition including particles, polymorphs and/or purified forms of a Compound of the Invention is administered in two daily doses, where the total daily dose is about 1000 mg.

In some embodiments, the therapeutically effective amount of the pharmaceutical composition including particles, polymorphs and/or purified forms of a Compound of the Invention is administered in two daily doses, where each dose is in a range of from about 80 mg to 1000 mg. In some embodiments, the therapeutically effective amount of the pharmaceutical composition including particles, polymorphs and/or purified forms of a Compound of the Invention is administered in two daily doses, where each dose is in a range of from about 160 mg to 600 mg. In some embodiments, the therapeutically effective amount of the pharmaceutical composition including particles, polymorphs and/or purified forms of a Compound of the Invention is administered in two daily doses, where each dose is in a range of from about 200 mg to about 500 mg. In some embodiments, the therapeutically effective amount of the pharmaceutical composition including particles, polymorphs and/or purified forms of a Compound of the Invention is administered in two daily doses, where each dose is about 500 mg.

In some embodiments, the therapeutically effective amount of the pharmaceutical composition including particles, polymorphs and/or purified forms of a Compound of the Invention is administered in three daily doses, where the total daily dose is in a range of from about 240 mg to about 1500 mg. In some embodiments, the therapeutically effective amount of the pharmaceutical composition including particles, polymorphs and/or purified forms of a Compound of the Invention is administered in three daily doses, where the total daily dose is in a range of from about 480 mg to about 1500 mg.

In some embodiments, the therapeutically effective amount of the pharmaceutical composition including particles, polymorphs and/or purified forms of a Compound of the Invention is administered in three daily doses, where each dose is in a range of from about 80 mg to 500 mg. In some embodiments, the therapeutically effective amount of the pharmaceutical composition including particles, polymorphs and/or purified forms of a Compound of the Invention is administered in three daily doses, where each dose is in a range of from 160 mg to 500 mg.

A Compound of the Invention or a pharmaceutical composition thereof can be administered through any one of or through a combination of routes, for example, orally, intravenously, or intraperitoneally. For example, in some embodiments, a Compound of the Invention can be administered orally. In some embodiments, a Compound of the Invention can be administered orally in a formulation that includes Gelucire and Tween 80.

A Compound of the Invention can be administered in a dose to achieve a blood concentration in a subject, e.g., a patient, of compound in the range of from at least about 0.002 µM to about 30 µM for a time of at least 2 hours to no more than 24 hours. In some embodiments, a Compound of the Invention can be administered in a dose to achieve a blood concentration in a subject of compound in the range of from at least about 0.2 µM to about 1 µM for a time of at least 2 hours to no more than 24 hours. equals to or above about 0.2 µM, 0.5 µM, 1.0 µM, 1.5 µM, 2.0 µM, 2.5 µM, 3.0 µM 4.0 µM, 5.0 µM, 6.0 µM, 7.0 µM, 8.0 µM, 9.0 µM, 10.0 µM, 15.0 µM for at least 2 hours and less than 24 hours. In some embodiments, a Compound of the Invention can be administered in a dose to achieve a blood concentration in a subject of compound equals to or above about 1.0 µM, 1.5 µM, 2.0 µM, 3.0 µM, 5.0 µM, 10.0 µM, 15.0 µM for at least 2 hours and less than 24 hours. In some embodiments, a Compound of the Invention can be administered in a dose to achieve a blood concentration in a subject of compound equals to or above about 2.0 µM, 3.0 µM, 5.0 µM, 10.0 µM for at least 2 hours and less than 24 hours. In some embodiments, a Compound of the Invention can be administered in a dose to achieve a blood concentration in a subject of compound equals to or above about 3.0 µM, or 5.0 µM for at least 2 hours and less than 24 hours.

A Compound of the Invention can be administered in a dose to achieve a blood concentration in a subject, e.g., a patient, of compound in the range of from at least about 0.002 µM·h to about 300 µM·h in 24 hours. In some embodiments, a Compound of the Invention can be administered in a dose to achieve area under the curve in 24 hours (AUC24) in a subject equals to or above about 0.2 µM, 0.5 µM, 1.0 µM, 1.5 µM, 2.0 µM, 2.5 µM, 3.0 µM 4.0 µM, 5.0 µM, 6.0 µM, 7.0 µM, 8.0 µM, 9.0 µM, 10.0 µM, 15.0 µM for at least 2 hours and less than 24 hours. In some embodiments, a Compound of the Invention can be administered in a dose to achieve a blood concentration in a subject of compound equals to or above about 1.0 µM, 1.5 µM, 2.0 µM, 3.0 µM, 5.0 µM, 10.0 µM, 15.0 µM for at least 2 hours and less than 24 hours. In some embodiments, a Compound of the Invention can be administered in a dose to achieve a blood concentration in a subject of compound equals to or above about 2.0 µM, 3.0 µM, 5.0 µM, 10.0 µM for at least 2 hours and less than 24 hours. In some embodiments, a Compound of the Invention can be administered in a dose to achieve a blood concentration in a subject of compound equals to or above about 3.0 µM, or 5.0 µM for at least 2 hours and less than 24 hours. In some embodiments, a Compound of the Invention can be administered in a dose to achieve area under the curve in 24 hours ($AUC_{0-24\ hr}$) in a subject equals to or above about 2 µM*hr, 10 µM*hr, 20 µM*hr, 30 µM*hr, 40 µM*hr, 50 µM*hr, 60 µM*hr, 70 µM*hr, 80 µM*hr, 90 µM*hr, 100 µM*hr, 125 µM*hr, 150 µM*hr, 200 µM*hr, 250 µM*hr, 300 µM*hr, 400 µM*hr, and 500 µM*hr.

If the condition of the subject (patient) so requires, doses of the pharmaceutical composition may be administered as a continuous or pulsatile infusion. The duration of a treatment may be decades, years, months, weeks, or days, as long as the benefits persist. The foregoing ranges are provided only as guidelines and are subject to optimization.

In a method according to the invention, cells of the neoplasm are selectively killed by administering the pharmaceutical composition, so that the blood molar concentration of the compound is at least an effective concentration and less than a harmful concentration for a first continuous time period that is at least as long as an effective time period and shorter than a harmful time period. The blood molar concentration can be less than the effective concentration after the first continuous time period. The effective concentration can be a concentration sufficiently high, so that neoplastic cells, e.g., cancer cells, are killed. The effective time period can be sufficiently long, so that neoplastic cells, e.g., cancer cells, are killed. The harmful concentration can be a concentration at which normal cells are damaged or killed. The harmful time period can be a time period sufficiently long for normal cells to be damaged or killed. For example, the effective concentration can be equal to or above about 0.02 µM, about 0.05 µM, about 0.1 µM, about 0.2 µM, about 0.5 µM, about 1 µM, about 3 µM, about 10 µM or about 20 µM. For example, the non-harmful concentration can be equal to or below about 3 µM, about 10 µM, about 14 µM, about 30 µM, or about 100 µM. For example, the effective time period can be equal to or above about 2 hour, about 4 hours, about 6 hours, about 12 hours, about 24 hours, or about 48 hours. For example, to achieve non-harmful exposure for normal cells, drug concentration of Compound 1 has to be substantially cleared from blood within about 12 hours, about 24 hours. "Substantially clearance from blood" means blood drug concentration decrease by at least about 50%, at least about 60%, at least about 80%, at least about 90%. For example, an effective concentration can be a concentration that exceeds the $IC_{50}$ of cancer cells when the compound is administered for some time period. For example, an effective time period can be a time period over which cancer cells are selectively inhibited or killed when the compound is administered at least at the effective concentration. For example, a harmful concentration can be a concentration that exceeds the $IC_{50}$ of normal cells when the compound is administered for any time period. For example, a harmful time period can be a time period over which normal as well as cancer cells are inhibited or killed when the compound is administered at the effective concentration.

One of skill in the art can administer the pharmaceutical composition by selecting dosage amount and frequency so as to achieve a herein described "selective pharmacokinetic profile" (SPP) deemed necessary for selective killing neoplastic cells, such as cancer cells, and sparing normal cells. Such consideration of the SPP can also guide the design of the pharmaceutical composition, for example, the particle size distribution and distribution of shapes of the particles.

In a method according to the invention, the pharmaceutical composition is administered orally in a dosage form such as a tablet, pill, capsule (hard or soft), caplet, powder, granule, suspension, solution, gel, cachet, troche, lozenge, syrup, elixir, emulsion, oil-in-water emulsion, water-in-oil emulsion, or draught.

Identifying an Optimum Particle Size Distribution

In a method according to the invention, an optimum particle size distribution of a compound according to Formula I, Compound 1, a polymorph of Compound 1, and/or a substantially pure form of Compound 1 for treating a human, mammal, or animal afflicted with a neoplasm can be determined as follows. At least one set of particles including the compound can be prepared. In preparing the set of particles, for example, the particle size of a sample of solid compound can be reduced by, for example, dissolving the compound and nebulizing the solution, dissolving the compound and sonicating the solution, ball milling the solid compound, roll milling the solid compound, grinding the solid compound, and/or sieving the solid compound. The particle size distribution of the at least one set of particles can be determined by a method or combination of methods known to one of skill in the art. For example, the particle size distribution can be determined using a technique such as sieve analysis, optical microscopic counting, electron micrograph counting, electroresistance counting, sedimentation time, laser diffraction, acoustic spectroscopy, another technique, or a combination of techniques. The at least one set of particles can be administered to neoplastic cells and to normal cells at a predetermined concentration and for a predetermined period of time. The effect of the particles on the metabolism, division, and/or other indicator of the vitality of the neoplastic cells and the normal cells can be observed. The observed effect of the particles on the neoplastic cells can be used to assign an effectivity rating to each set of particles. For example, a set of particles that inhibits the metabolism and/or division of the neoplastic cells, damages or kills the neoplastic cells, or otherwise exhibits high antitumor activity can be assigned a high effectivity rating. The observed effect of the particles on the normal cells can be used to assign a toxicity rating to each set of particles. For example, a set of particles that inhibits the metabolism and/or division of the normal cells or damages or kills the normal cells or where the normal cells otherwise exhibit a low tolerability of the set of particles can be assigned a high toxicity rating.

For example, the set of particles can be administered to neoplastic cells and normal cells in vitro. For example, the effectivity rating can be equal to, proportional to, or a monotonically increasing function of the $IC_{50}$ of the neoplastic cells. For example, the toxicity rating can be equal to, proportional to, or a monotonically increasing function of the $IC_{50}$ of the normal cells.

For example, the set of particles can be administered to neoplastic cells and normal cells in vivo in a test animal. For example, the test animal can be a mammal, primate, mouse, rat, guinea pig, rabbit, or dog. For example, the effectivity rating can be equal to, proportional to, or a monotonically increasing function of the decrease in volume of the neoplastic cells following administration of the set of particles. For example, the toxicity rating can be equal to, proportional to, or a monotonically increasing function of the decrease in mass of the test animal following administration of the set of particles. For example, the set of particles can be administered to a human in a clinical study. A method of treating a neoplasm can include administering a therapeutically effective amount of a set of particles of the compound according to Formula I, Compound 1, a polymorph of Compound 1, and/or a substantially pure form of Compound 1 to a human, mammal, or animal afflicted with the neoplasm. Prior to administration of the particles of the compound, the compound according to Formula I, Compound 1, a polymorph of Compound 1, and/or a substantially pure form of Compound 1 to an animal or a human or to cells in vitro, the particles can be suspended in a pharmaceutically acceptable excipient.

The effectivity rating and/or the toxicity rating of each set of particles having a first particle size distribution can be compared with the effectivity rating and/or the toxicity rating of another set or sets of particles having a particle size distribution different than the first particle size distribution. A set of particles of a compound that has a high effectivity rating and a low toxicity rating can be effective in inhibiting or killing neoplastic, e.g., cancer, cells, but spare normal cells. One of skill in the art can select as an optimum set the set of particles having an effectivity rating greater than, a toxicity rating less than, and/or a weighted effectivity rating and toxicity rating sum greater than the at least one other set of particles (for example, the effectivity rating can be weighted with a positive coefficient and the toxicity rating can be weighted with a negative coefficient). One of skill the art can also use another criteria to select the optimum set of particles, for example, particles having a sum of the weighted effectivity rating and the weighted ratio of the effectivity rating over the toxicity rating. The particle size distribution of the optimum set of particles can be considered an optimum particle size distribution for the compound tested. The optimum particle size distribution may be different for one compound, e.g., Compound 1, than for another compound, e.g., a compound according to Formula I that is not Compound 1. The optimum particle size distribution for a given compound may differ when determined by administration to cells in vitro, to a small test animal, and to a large test animal. However, the optimum particle size distribution determined by administration of a given compound to an organism in vitro or in vivo may represent a rational starting point for optimizing the particle size distribution for another compound or for administration to another organism.

An optimum set of particles of the compound according to Formula I, Compound 1, a polymorph of Compound 1, and/or a substantially pure form of Compound 1 can be included in the composition for reducing or inhibiting the replication or spread of neoplastic cells.

EXAMPLES

Examples are provided below to further illustrate different features of the present invention. The examples also illustrate useful methodology for practicing the invention. These examples do not limit the claimed invention.

Example 1: Preparation of a Naphthofuran Compound

The procedure for preparation of a naphthofuran compound (2-acetylnaphtho[2,3-b]furan-4,9-dione) is summarized as follows:
Step 1: Bromination To a 2 liter 3 neck round bottom flask equipped with a mechanical stirrer, thermometer, and addition funnel is charged 3-butene-2-one (451.2 grams). To the addition funnel is added bromine (936.0 grams). After the content in the flask is cooled to −5° C., the bromine is dropped into the flask with vigorous stirring and maintaining temperature at −5° C. over 30 minutes. The mixture is stirred for an additional 15 minutes at −5° C., and then is split into 4 equal portions.
Step 2 Debromination Each portion of the mixture along with tetrahydrofuran (2133.6 grams) is loaded into a 22 liter 4 neck round bottom flask equipped with a mechanical stirrer, thermometer, and addition funnel. To the addition funnel is charged DBU (1,3-Diazabicyclo[5.4.0]undec-7-ene, 222.9 grams). The DBU is dropped into the flask with vigorous stirring and maintaining temperature at 0° C.-5° C. over 30 minutes. The mixture is stirred for an additional 15 min at 0° C.-5° C.
Step 3: Coupling Reaction 2-hydroxy-1,4-naphthofuran (231 grams) is then added into the flask. Additional DBU (246.0 grams) is charged into the addition funnel and then dropped into the mixture in the flask at such a rate that the temperature of the reaction mixture does not exceed 40° C. After the addition of DBU is complete, the resulting mixture is stirred overnight at room temperature, and a sample of the reaction mixture is taken for HPLC analysis.
Step 4: Crystallization To the reaction mixture, water (10.8 liters) is charged, and the resulting mixture is cooled to 0° C.-3° C. for at least 30 minutes, then filtered via vacuum filter. The filtered solid is rinsed with 5% aqueous sodium bicarbonate (3 liters), water (3 liters), 1% aqueous acetic acid (3 liters) and ethanol twice (2×1 liter) successively.

The rinsed solid is stored and pooled together from other batches. The combined crude product (28.73 kg) is loaded along with ethyl acetate (811.7 kg) into a 500 gallon vessel equipped with a mechanical stirrer, thermometer, and a condenser. Under nitrogen atmosphere, the mixture is heated to reflux (72° C.) for 2 hours, and then filtered with a 10 micron cartridge filter containing an active carbon layer to remove insolubles.

Fresh hot ethyl acetate (10 kg) is used to rinse the vessel, transfer line and filter. The combined filtrate is cooled to 0-5° C. and held at this temperature for 2 hours, and then is filtered with 20 inch Buchner filter. The filtered solid product is rinsed with 0-5° C. ethyl acetate (5.7 kg), and dried under vacuum at 40° C. to a constant weight. The remaining filtrate is reduced in volume by 63% by evaporation, and the crystallization process was repeated again to generate a second crop of product which was also dried under the same condition as the first crop of product.

A lot of the naphthofuran compound obtained following the procedure. The purity for the lot of the compound is 95.44 area % (HPLC).

Example 2: Preparation of a Naphthofuran Compound

Another procedure for the preparation of a naphthofuran compound (2-acetylnaphtho[2,3-b]furan-4,9-dione) is summarized as follows:

Step 1: Bromination

A 12 L RBF (Round Bottom Flask)(protected from light with UV filters) was charged with MVK (2,160 ml, 26.4 mol) and cooled to −9.6° C. in a dry-ice/acetone bath. Bromine (1,300 ml, 25.3 mol) was added slowly, over 2 hrs and 20 min, maintaining T=<−2.6° C. ($T_{max}$). The resulting yellow mixture was stirred for additional 28 min.

Step 2: De-Hydrobromination

A 72 L RBF with pre-cooled THF (Tetrahydrofuran) (20 L, 5 ml/g HNQ (2-Hydroxy-1,4-naphtoquinone)) was charged with brominated product from the above and the resulting solution was cooled to −4.8° C. DBU (4,200 ml, 28.1 mol) dissolved in THF (4,200 ml) was added slowly, over 2 hrs and 20 min, maintaining T<0.3° C. ($T_{max}$). The resulting suspension was stirred for 42 min.

Step 3: Coupling

2-Hydroxy-1,4-naphthofuran (4,003 g, 23.0 mol) was charged, in one portion, into the reaction mixture from the above, at −1.8° C. A cooling bath was added while a second portion of DBU (3,780 ml, 25.3 mol) was added over 48 minutes to bring the reaction temperature to 40° C. The cooling bath was removed and the reaction mixture was stirred over the weekend, open to the air.

Step 4: Isolation of Crude Material

A 200 L reactor with pre-cooled water (100 L, 25 ml/g HNQ) was charged with the reaction mixture from the above. The resulting suspension was cooled to 6.0° C., and then stirred at T=3±3° C. for ~1 hour. The resulting suspension was then filtered, and the collected solids were transferred back to the 200 L reactor.

After stirring in 5% NaHCO$_3$ aqueous (26 L, 6.5 ml/g HNQ) for 1 hour, the suspension was filtered. The collected solids were transferred back to the 200 L reactor, stirred in water (26 L) for 1 hour, and then filtered.

The wet solids were transferred back to the 200 L reactor, stirred in 1% aqueous acetic acid (26 L) for ~1 hour, filtered and then washed on the filter funnel with water (10 L). The collected solids were transferred back to the 200 L reactor and heated in ethanol (17.5 L; 4.3 ml/g HNQ) to a gentle reflux (77.4° C.). The resulting suspension was cooled to 4.2° C. and filtered.

The wet solids were transferred to a 100 L reactor and heated in ethanol (17.5 L; 4.3 ml/g HNQ) to a reflux (77.6° C.). The resulting suspension was cooled to 4.5° C. and filtered. The wet cake was de-liquored overnight. $^1$H NMR and HPLC samples were taken. $^1$H NMR: Compound 1/NDHF (2-acetyl-2,3-dihydronaphtho[2,3-b]furan-4,9-dione) 42:58%; HPLC: Compound 1/NDHF 74:11 area %.

The solids were dried in a vacuum oven at 50° C., over 4 days, affording 2,268 g of crude Compound 1. $^1$H NMR: Compound 1/NDHF 41:59%; HPLC: Compound 1/NDHF 67:11 area %.

Step 5: Oxidation of the Naphthodihydrofurane

The crude Compound 1 (2.268 kg) was slurried in toluene (77 L). MnO$_2$ (9536 g) was added and the mixture was heated to a gentle reflux. TLC (1:1 EA:hexane) showed complete reaction after 1 hour.

The reaction mixture was then filtered hot through a preheated pad of Celite (1530 g, bottom layer), activated charcoal (2230 g, middle layer), and Celite (932 g, top layer). The yellow-orange filtrate was collected.

The filtrate was concentrated on the rotovap to approximately 1/10 volume. The slurry was filtered and washed with toluene. The crystals were then dried at 50° C. to give 952 g (42%) of dark yellow solid. HPLC: 99.94%. $^1$H NMR showed no naphthodihydrofuran.

The crystals were dried at 50° C. under vacuum for an additional 46-65 hours to reduce the amount of residual toluene in the material.

Step 6: Ethyl Acetate Treatment

The Compound 1 (5816 g) was charged to a 200 L reaction vessel. Ethyl acetate (145 L, 25 mL/g) was added, and the solution was heated to reflux over 2 hours 26 minutes. Reflux was maintained for 5 hours 30 minutes, and the mixture was then cooled and maintained overnight to 17° C.

The slurry was filtered on a polyethylene frit. The yellow crystals were air dried, then placed in trays in a vacuum oven for 75 hours, giving 5532 g (95.1% yield) of yellow solids. HPLC: 99.86%. $^1$H NMR matches the structure of Compound 1.

Step 7: Ethyl Acetate Re-Crystallization

A 2 L RBF was charged with crude material (10 g) and ethyl acetate (900 ml). The mixture was refluxed at ~77° C. and then more ethyl acetate (100 ml) was added to achieve complete dissolution. The resulting clear-yellowish solution was stirred at reflux for ~30 minutes, and then the heating was removed. The mixture was stirred overnight at room temperature.

The resulting suspension was filtered and the collected yellow solids were rinsed on the funnel with ethyl acetate (30 ml). The wet solid was dried in vacuum oven at 40-50° C., over 4 hours, to obtain 8.53 g of yellow crystalline product (total yield ~17%).

$^1$H NMR: consistent with structure; HPLC: 99.94 area %; DSC: 228.68° C., 151 J/g.

Unless specifically indicated otherwise, Compound 1 used in the following examples was prepared as in Example 1.

Example 3: Micronization of Naphthofuran Compound

For example, Compound 1 crystals were milled and passed through a 160 micron (μm) sieve (Sieve #100, 150 μm opening) to generate the crystals of approximately 160 microns or less.

For example, Compound 1 crystals were milled (The Retsch Ultra centrifugal Mill ZM 200; Single pass, at 18,000 rpm using 0.25 mm screen) to a median particle size of about 20 micron. Table 3 presents the resultant distribution of particle sizes (Malvern 2000 with the Hydro 2000S wet accessory). The columns present the maximum size of particles in the cumulative percent total presented in the subscript at the header of the column. For example, the column $D_{90}$ presents the size for which 90% of the particles have an equal or lesser size. The column $D_{50}$ represents the median size—half of the particles have a greater size, and half of the particles have an equal or lesser size.

TABLE 3

Particle Size Distribution of Milled Compound 1.

| | Particle Size (microns) | | |
|---|---|---|---|
| | $D_{90}$ | $D_{50}$ | $D_{10}$ |
| Sample B | 48.9 | 20.2 | 2.3 |

For example, Compound 1 crystals were micronized using a jet milling method (4" Jet Mill, Venturi pressure=40, Mill pressure=100, Feed rate=1304 g/hour) to a median particle size of about 2 micron, as presented in Table 4. Particle size analysis was performed using a dry particle method (Sympatec Helos/KF Particle Size Analyzer).

TABLE 4

Particle Size Distribution of Micronized Compound 1

| | Particle Size (microns) | | |
|---|---|---|---|
| | $D_{90}$ | $D_{50}$ | $D_{10}$ |
| Sample A | 4.63 | 2.07 | 0.53 |

A cumulative distribution function derived from a log-normal model of particle size distribution provided a good fit to the data presented in Table 4. The cumulative distribution function was represented as $$CDF(d) = \frac{1}{2}\left(1 + \text{erf}\left(\frac{\ln(d) - \ln(d_{median})}{\sigma\sqrt{2}}\right)\right),$$

where erf is the error function, d is the particle diameter variable, $d_{median}$ is the median particle size, and $\sigma$ is a parameter related to the breadth of the cumulative distribution function. CDF(d) represents the fraction of particles having a size less than or equal to d. Setting $d_{median}$ to the observed median of 2.07 micron, fitting of the model yielded a value of $\sigma$=1.06. The model indicated a mean diameter of 3.6 micron and a mode diameter of 0.67 micron. The model also suggests a specific area of the particles of 2200 m²/kg, although this does not account for factors such as surface roughness.

Example 4: Pharmacokinetics in Mice of 2 Micron, 20 Micron, 150 Micron Median Particle Size Formulations In an experiment, micronized Compound 1 prepared in step 6 of Example 2 with a mean particle size of 2 micron, 20 microns, 150 microns were formulated as suspensions in 20% Gelucire 44/14 and 1% Tween 80 and administered orally to mice at 100 mg/kg. Each time point represents the average of 3 mice (FIG. 16).

As shown in FIG. 16, while the Compound 1 with a particle size of between 125-150 micron shows a lower level of exposure compared to the 2 micron and 20 micron particles when all are dosed at 100 mg/kg, it shows the same pattern. Compound 1 particle sizes of 20 micron (d50) show similar plasma exposure in mice as dose Compound 1 with particle sized of 2 micron (d50). Furthermore, if you double the exposure of the 125-150 micron Compound 1, it would be very similar to the 2 and 20 micron PK graph.

Example 5: Formulations Having Reduced Particle Size Exhibit Greater Inhibition of Tumor Growth In the present studies, Compound 1 shows no or weak efficacy if it administered to mice in a composition with particle size greater than 20 micron. However, Compound 1 was found to have potent anti-tumor activity with no observed toxicity if the compound is administered in a composition of a particle size less than 5 micron.

In an experiment, a formulation of Compound 1 particles sieved to 160 micron was tested in the model of immunosuppressed mice with established subcutaneous xenograft FaDu human head and neck cancer. The pharmaceutical composition was formulated as 80 mg/ml in 9% Gelucire, 20% Vitamin E TPGS (Table 3). No efficacy was observed at the dose of 400 mg/kg daily oral dosing (a vehicle control was also administered), as shown in FIG. 15. This dose level is 4 fold higher that that used in the PK experiment shown in FIG. 16. Therefore these mice receive 4× higher exposure than that see by dosing 100 mg/kg 2 micron Compound 1 which shows good efficacy. All regimens were administered daily (qd).

In an experiment, Compound 1 crystals were milled to a median particle size of about 20 micron. Only weak or moderate efficacy was observed when the Compound 1 milled to a median particle size of about 20 microns was dosed orally daily at 200 mg/kg in mice with xenografted FaDu human head and neck tumors (FIG. 15) (a vehicle control was also administered). All regimens were administered daily (qd).

Compound 1 crystals prepared in Example 1 were also tested. The Compound 1 crystals were micronized using a jet milling method (4" Jet Mill, Venturi pressure=40, Mill pressure=100, Feed rate=1304 g/hour) to a median particle size of about 2 micron, as presented in Table 4.

FaDu human head and neck cancer cells were inoculated subcutaneously into female athymic nude mice (6×10⁶ cells/mouse) and allowed to form palpable tumors. When the tumors reached approximately 100 mm³, the animals were treated orally (po) with Compound 1 at 100 mg/kg or vehicle control daily. Compound 1 was formulated at 10 mg/ml in 20% gelucire. Tumors and bodyweights were measured throughout treatment (FIG. 15).

Compound 1 was also micronized using a jet milling method (8" Pancake Mill, Ventury pressure=40, Mill pressure=40, Feed rate=1920 g/hour) to a median particle size of about 2 micron, as presented in Table 5. Particle size analysis was performed using a dry particle method (Sympatec Helos/KF Particle Size Analyzer). Similar anti-tumor activity was observed as the 2 micron material in Table 4.

TABLE 5

Particle Size Distribution of Micronized Compound 1

| | Particle Size (microns) | | |
|---|---|---|---|
| | $D_{90}$ | $D_{50}$ | $D_{10}$ |
| Sample A | 5.5 | 2.21 | 0.51 |

Therefore, while Compound 1 of either 150 micron or 20 microns shows a similar plasma exposure pattern as Compound 1 of 2 microns (FIG. 16). They show different efficacy: Compound 1 of 150 microns shows no efficacy (FIG. 15); Compound 1 of 20 microns shows weak or moderate efficacy; and Compound 1 of 2 microns shows strong efficacy.

As shown in FIG. 16, Compound 1 particle sizes of 20 micron (d50) shows similar plasma exposure in mice as dose Compound 1 with particle sized of 2 micron (d50). Surprisingly, however, Compound 1 with 20 micron particle size shows only weak or moderate efficacy in mouse xenograft models, while Compound 1 with 2 micron particle size shows potent efficacy. This is an unexpected result as the common understanding is that the efficacy of a drug is based on its pharmacokinetics. Therefore since both particle sizes show the same pharmacokinetics, they should both be equally efficacious.

Furthermore, if the exposure of the 125-150 micron Compound 1 is doubled, it would be very similar to the 2 and 20 micron PK graph. Interestingly, when 150 micron Compound 1 is dosed to mice at a level as high as 400 mg/kg, it also shows no efficacy in xenograft models (FIG. 15).

These results go against the conventional view of the reduction of particle size leading to increased plasma exposure and therefore better efficacy.

Example 6: HPLC Assay

This HPLC method is to assess purity of naphthofuran, e.g., 2-acetylnaphtho[2,3-b]furan-4,9-dione (Compound 1), and its reaction completion by HPLC. All components will be expressed in area percent of the total peaks within the chromatogram.

1. Apparatus And Materials (Table 6A)

| Apparatus | HPLC system with UV detector and integration system |
|---|---|
| Column | Phenomenex Luna C18(2) 5-μm, 4.6-mm × 250-mm (P/N 00G-4252-E0) or equivalent |
| pH meter | calibrated the day of use |
| Acetonitrile | HPLC Grade |
| Dimethylsulfoxide (DMSO) | ACS Grade or better |
| Phosphoric acid | ACS reagent |
| Potassium phosphate, dibasic | ACS reagent |
| Compound 1 | Reference Material |

2. Solution Preparations 10 mM Phosphate Buffer

Weigh 1.74 g of Potassium Phosphate, dibasic and dilute with 1 L of Purified Water (adjust weights and volumes for amount needed). Adjust the pH with Phosphoric Acid to pH 6.8.

Mobile Phase A

Prepare Mobile Phase A by mixing the 10 mM phosphate buffer and acetonitrile to a 80:20 buffer:acetonitrile ratio. Degas.

Mobile Phase B

Prepare Mobile Phase B by mixing the 10 mM phosphate buffer and acetonitrile to a 20:80 buffer:acetonitrile ratio. Degas.

Diluent

Mobile Phase A will be used as the diluent for all sample and standard preparations.

3. Standards Preparations

Compound 1 Stock Standard (Concentration≈1.0 mg/mL)

It will be prepared weighing 10 mg of Compound 1 Reference material into a 20 mL scintillation vial; record weight±0.01 mg. Add 10 mL of DMSO and sonicate until the solids dissolve.

$$\text{Concentration} = \frac{\text{(Wt. Reference Standard, mg)} \times \text{Standard Decimal Purity}}{\text{(Volume of Stock Solution, mL)}}$$

Stock Test Samples (Concentration≈1.0 mg/mL)

Test Solutions will be prepared by weighing 10 mg of sample in a 20 mL scintillation vial and diluting with 10 mL of DMSO.

$$\text{Concentration} = \frac{\text{(Wt. Sample, mg)}}{\text{(Volume of Stock Solution, mL)}}$$

Working Test Samples (Concentration≈0.01 mg/mL)

This solution is prepared by transferring 1 mL into a 100 mL volumetric flask and diluting with diluent solution.

$$\text{Concentration} = \frac{\text{Stock Test Sample Concentration} \times \text{(volume transferred, mL)}}{\text{(Volume of Working Solution, mL)}}$$

4. Instrument Operating Conditions (Table 6B)

| Flow Rate | 0.8 mL/min. |
|---|---|
| Column temp | 30° C. |
| Detector Wavelength | 270 nm |
| Injection Volume | 40 μL |
| Gradient Profile | 0-5 min - 0% B to 0% B |
| | 5-19 min - 0% B to 90% B |
| | 19-24 min - 90% B to 90% B |
| | 24-29 min - 90% B to 0% B |
| | Note: 5 min equilibration time between injections at 100% A |
| Run Time | 29 min |

5. Operating Procedure

Inject solutions in the following sequence:
1. Diluent blank (1×)
2. Compound 1 Working Standard (5×)
3. Test Solutions (2× each)
4. Working Standards (1× each)

6. System Suitability

The system is suitable for use if the following criteria are met.
1. Diluent blank injection at the beginning of the sequence contains no interfering peaks with any identified impurities
2. The initial, 5 replicate injections of the Compound 1 working standard have (1) % $\text{RSD}_{peak\ area}$<3.0%; (2) % $\text{RSD}_{retention\ time}$<3.0%; and (3) mean tailing factor <2.0.
3. In the chromatogram for the bracketed standard, (1) retention time is 97.0-103.0% of the mean retention time from the initial suitability injections and (2) its area % is 97.0-103.0% of the initial value.

7. Calculations

All peaks will be reported as area % of the total peaks in the chromatogram, this will be calculated by the integration software by way of the following formula:

$$\text{Area \%} = \frac{\text{Area counts of peak}}{\text{Total area of all peaks}} \times 100$$

NMR and TLC
NMR (Table 6C)

| Apparatus | Varian Inova 500 NMR Spectrometer |
|---|---|
| Pulse Sequence | S2pul |
| Solvent | CDC13 |
| Temp. | 25.0° C./298.1 K |
| Relax delay | 1.000 sec |
| Pulse | 45.0 degrees |

-continued

| | |
|---|---|
| Acq. time | 2.732 sec |
| Width | 11992.2 Hz |
| | 32 repetitions |
| OBSERVE H1 | 499.7029706 MHz |
| FT size | 65536 |
| Total time | 1 min, 50 sec |

TLC on Silica Gel (Table 6D)

| | |
|---|---|
| eluent | ethyl acetate:hexane, 1:1 |
| visualization | UV |
| $Rf_{401}$ | ~0.7 |
| $Rf_{NDHF}$ | ~0.6 |

Example 7: Preparation of 2-acetylnaphtho[2,3-b]furan-4,9-dione

A procedure for the preparation of Compound 1 is provided below.
Step 1: Bromination
To a 2 liter 3 neck round bottom flask equipped with a mechanical stirrer, thermometer, and addition funnel is charged 3-butene-2-one (451.2 grams). To the addition funnel is added bromine (936.0 grams). After the content in the flask is cooled to −5° C., the bromine is dropped into the flask with vigorous stirring and maintaining temperature at −5° C. over 30 minutes. The mixture is stirred for an additional 15 minutes at −5° C., and then is split into 4 equal portions.
Step 2: Debromination
Each portion of the mixture along with tetrahydrofuran (2133.6 grams) is loaded into a 22 liter 4 neck round bottom flask equipped with a mechanical stirrer, thermometer, and addition funnel. To the addition funnel is charged DBU (1,3-Diazabicyclo[5.4.0]undec-7-ene, 222.9 grams). The DBU is dropped into the flask with vigorous stirring and maintaining temperature at 0° C.-5° C. over 30 minutes. The mixture is stirred for an additional 15 min at 0° C.-5° C.
Step 3: Coupling Reaction
2-hydroxy-1,4-naphthoquinone (231 grams) is then added into the flask. Additional DBU (246.0 grams) is charged into the addition funnel and then dropped into the mixture in the flask at such a rate that the temperature of the reaction mixture does not exceed 40° C. After the addition of DBU is complete, the resulting mixture is stirred overnight at room temperature, and a sample of the reaction mixture is taken for HPLC analysis.
To the reaction mixture, water (10.8 liters) is charged, and the resulting mixture is cooled to 0° C.-3° C. for at least 30 minutes, then filtered via vacuum filter. The filtered solid is rinsed with 5% aqueous sodium bicarbonate (3 liters), water (3 liters), 1% aqueous acetic acid (3 liters) and ethanol twice (2×1 liter) successively.
Step 4: Crystallization
The rinsed solid is stored and pooled together from other batches. The combined crude product (28.73 kg) is loaded along with ethyl acetate (811.7 kg) into a 500 gallon vessel equipped with a mechanical stirrer, thermometer, and a condenser. Under nitrogen atmosphere, the mixture is heated to reflux (72° C.) for 2 hours, and then filtered with a 10 micron cartridge filter containing an active carbon layer to remove insolubles.
Fresh hot ethyl acetate (10 kg) is used to rinse the vessel, transfer line and filter. The combined filtrate is cooled to 0-5° C. and held at this temperature for 2 hours, and then is filtered with 20 inch Buchner filter. The filtered solid product is rinsed with 0-5° C. ethyl acetate (5.7 kg), and dried under vacuum at 40° C. to a constant weight.
The remaining filtrate is reduced in volume by 63% by evaporation, and the crystallization process was repeated again to generate a second crop of product which was also dried under the same condition as the first crop of product.
Two lots of Compound 1 were obtained following the procedure. One lot has a purity of 91.64 area % and the other lot has a purity of 95.44 area %, measured by HPLC.

Example 8: Preparation of crude 2-acetylnaphtho[2,3-b]furan-4,9-dione

Another procedure for the preparation of Compound 1 is summarized as follows.
Step 1: Bromination
A 12 L RBF (Round Bottom Flask) (protected from light with UV filters) was charged with MVK (2,160 ml, 26.4 mol) and cooled to −9.6° C. in a dry-ice/acetone bath. Bromine (1,300 ml, 25.3 mol) was added slowly, over 2 hrs and 20 min, maintaining T=<−2.6° C. ($T_{max}$). The resulting yellow mixture was stirred for additional 28 min.
Step 2: De-Hydrobromination
A 72 L RBF with pre-cooled THF (Tetrahydrofuran) (20 L, 5 ml/g HNQ (2-Hydroxy-1,4-naphtoquinone)) was charged with brominated product from the above and the resulting solution was cooled to −4.8° C. DBU (4,200 ml, 28.1 mol) dissolved in THF (4,200 ml) was added slowly, over 2 hrs and 20 min, maintaining T<0.3° C. ($T_{max}$). The resulting suspension was stirred for 42 min.
Step 3: Coupling
2-Hydroxy-1,4-naphthoquinone (4,003 g, 23.0 mol) was charged, in one portion, into the reaction mixture from the above, at −1.8° C. A cooling bath was added while a second portion of DBU (3,780 ml, 25.3 mol) was added over 48 minutes to bring the reaction temperature to 40° C. The cooling bath was removed and the reaction mixture was stirred over the weekend, open to the air.
Step 4: Isolation of Crude Material
A 200 L reactor with pre-cooled water (100 L, 25 ml/g HNQ) was charged with the reaction mixture from the above. The resulting suspension was cooled to 6.0° C., and then stirred at T=3±3° C. for ~1 hour. The resulting suspension was then filtered, and the collected solids were transferred back to the 200 L reactor.
After stirring in 5% NaHCO₃ aqueous (26 L, 6.5 ml/g HNQ) for 1 hour, the suspension was filtered. The collected solids were transferred back to the 200 L reactor, stirred in water (26 L) for 1 hour, and then filtered.
The wet solids were transferred back to the 200 L reactor, stirred in 1% aqueous acetic acid (26 L) for ~1 hour, filtered and then washed on the filter funnel with water (10 L). The collected solids were transferred back to the 200 L reactor and heated in ethanol (17.5 L; 4.3 ml/g HNQ) to a gentle reflux (77.4° C.). The resulting suspension was cooled to 4.2° C. and filtered.
The wet solids were transferred to a 100 L reactor and heated in ethanol (17.5 L; 4.3 ml/g HNQ) to a reflux (77.6° C.). The resulting suspension was cooled to 4.5° C. and filtered. The wet cake was de-liquored overnight. ¹H NMR and HPLC samples were taken. ¹H NMR: Compound 1/NDHF (2-acetyl-2,3-dihydronaphtho[2,3-b]furan-4,9-dione) 42:58%; HPLC: Compound 1/NDHF 74:11 area %.
The solids were dried in a vacuum oven at 50° C., over 4 days, affording 2,268 g of crude Compound 1. ¹H NMR: Compound 1/NDHF 41:59%; HPLC: Compound 1/NDHF 67:11 area %.

Example 9: Oxidation of the Naphthodihydrofurane

The crude Compound 1 (2.268 kg) was slurried in toluene (77 L). MnO₂ (9536 g) was added and the mixture was heated to a gentle reflux. TLC (1:1 EA:hexane) showed complete reaction after 1 hour.

The reaction mixture was then filtered hot through a preheated pad of Celite (1530 g, bottom layer), activated charcoal (2230 g, middle layer), and Celite (932 g, top layer). The yellow-orange filtrate was collected.

The filtrate was concentrated on the rotovap to approximately 1/10 volume. The slurry was filtered and washed with toluene. The crystals were then dried at 50° C. to give 952 g (42%) of dark yellow solid. HPLC: 99.94%. $^1$H NMR showed no naphthodihydrofuran.

The crystals were dried at 50° C. under vacuum for an additional 46-65 hours to reduce the amount of residual toluene in the material.

Example 10: Ethyl Acetate Treatment

The Compound 1 (5816 g) was charged to a 200 L reaction vessel. Ethyl acetate (145 L, 25 mL/g) was added, and the solution was heated to reflux over 2 hours 26 minutes. Reflux was maintained for 5 hours 30 minutes, and the mixture was then cooled and maintained overnight to 17° C.

The slurry was filtered on a polyethylene frit. The yellow crystals were air dried, then placed in trays in a vacuum oven for 75 hours, giving 5532 g (95.1% yield) of yellow solids. HPLC: 99.86%. $^1$H NMR matches the structure of Compound 1.

Example 11: Ethyl Acetate Re-Crystallization

A 2 L RBF was charged with crude material (10 g) and ethyl acetate (900 ml). The mixture was refluxed at ~77° C. and then more ethyl acetate (100 ml) was added to achieve complete dissolution. The resulting clear-yellowish solution was stirred at reflux for ~30 minutes, and then the heating was removed. The mixture was stirred overnight at room temperature.

The resulting suspension was filtered and the collected yellow solids were rinsed on the funnel with ethyl acetate (30 ml). The wet solid was dried in vacuum oven at 40-50° C., over 4 hours, to obtain 8.53 g of yellow crystalline product (total yield ~17%).

$^1$H NMR: consistent with structure; HPLC: 99.94 area %; DSC: 228.68° C., 151 J/g.

Example 12: Identification of Naphthofuran Compounds that Target Cancer and Cancer Stem Cells Methods
In Life Evaluations:
Daily examinations into the health status of each animal were also conducted. Body weights were checked every three days. Food and water was supplied daily according to the animal husbandry procedures of the facility. Treatment producing >20% lethality and or >20% net body weight loss were considered toxic. Results are expressed as mean tumor volume (mm$^3$)±SE. P Values <0.05 are considered to be statistically relevant.

Animal Husbandry:
Male or female athymic nude mice 4-5 weeks (Charles River Laboratories, Wilmington, Mass.), were acclimated to the animal housing facility for at least 1 week before study initiation. All of the experimental procedures utilized were consistent with the guidelines outlined by the American Physiology Society and the Guide for the Care and Use of Laboratory Animals and were also approved by the Institutional Animal Care and Use Committee of Boston Biomedical Inc. The animals were housed in groups of four in wood chip bedded cages in a room having controlled temperature (68° F.-72° F.), light (12-h light-dark cycle), and humidity (45-55%). The animals were allowed free access to water and food during the experiment.

Example 13: Clinical Trial: Safety and Efficacy 2-acetylnaphtho[2,3-b]furan-4,9-dione was chosen to enter Phase I clinical trial after receiving IND approval from US FDA and Health Canada, which was a dose escalation study in adult patients with advanced cancer who had failed standard therapies. A cycle consists of twice-daily oral administration of the compound for 4 weeks. Cycles were repeated every 4 weeks (28 days) until progression of disease, unacceptable toxicity, or another discontinuation criterion is met. The dose escalation trial was conducted as open label and multicenter trial. A modified Simon accelerated titration scheme was used for dose escalation.

The primary objective of the trial was to determine the safety, tolerability, and recommended phase II dose (RP2D). The secondary objectives of the trial were to determine the pharmacokinetic profile of the compound, pharmacodynamics of the compound, and preliminary antitumor activity of the compound.

The inclusion criteria included histologically or cytologically confirmed solid tumor that is metastatic, unresectable, or recurrent; ≥18 years of age; Measurable disease by RECIST; and Karnofsky ≥70%. The exclusion criteria included chemotherapy, radiotherapy, immunotherapy or investigational agent within 4 weeks of first dose; surgery within 4 weeks of first dose; and known brain metastases.

As of Feb. 7, 2011, 42 cancer patients with various advanced solid tumors who have failed chemotherapies were enrolled in the study. The demographics and baseline disease characteristics of the patients selected under above criteria were summarized in Table 7.

TABLE 7

| Demographics and Baseline Disease Characteristics | | |
|---|---|---|
| | | Patients (N = 42) |
| Age (years) | Mean | 59.6 (12.7) |
| | Min, Max | 28, 91 |
| Sex [N (%)] | Male | 29 (70.7%) |
| | Female | 12 (29.3%) |
| Race [N (%)] | Causasian | 33 (80.5%) |
| | Asian | 3 (7.3%) |
| | Black | 1 (2.4%) |
| | Other | 2 (4.9%) |
| | Hispanic | 0 (0%) |
| Prior Therapies[1] | >3 | 20 |
| | 2 | 2 |
| | 1 | 4 |

Of those 42 patients, 10 cohorts were assessed at doses ranging from 20 mg to 2000 mg/day. The dose escalation was well tolerated and no dose limiting toxicity was observed. Adverse events were generally mild with the most common being: diarrhea, nausea, and fatigue. Grade 3 or greater events include: fatigue and diarrhea. These adverse events are recordings on what these late stage cancer patients experience while on the clinical trial, which may or may not be related to Compound 1. The adverse events were summarized in Table 8

TABLE 8

| | Summary of Adverse Events | | | | | | | |
|---|---|---|---|---|---|---|---|---|
| | Any Grade | | Grade 1 | | Grade 2 | | Grade 3 | |
| Event Term | # of Events | % of Total | # of Events | % of Total | # of Events | % of Total | # of Events | % of Total |
| Diarrhea | 23 | 28.4% | 20 | 24.7% | 2 | 2.5% | 2 | 2.5% |
| Vomiting | 14 | 17.3% | 13 | 16.0% | 1 | 1.2% | 0 | 0.0% |
| Nausea | 10 | 12.3% | 8 | 9.9% | 2 | 2.5% | 0 | 0.0% |
| abdominal cramps | 6 | 7.4% | 5 | 6.2% | 1 | 1.2% | 0 | 0.0% |
| weakness | 5 | 6.2% | 2 | 2.5% | 3 | 3.7% | 0 | 0.0% |
| Fatigue | 4 | 4.9% | 1 | 1.2% | 2 | 2.5% | 1 | 1.2% |
| Anorexia | 4 | 4.9% | 3 | 3.7% | 1 | 1.2% | 0 | 0.0% |
| Dysgusia | 3 | 3.7% | 3 | 3.7% | 0 | 0.0% | 0 | 0.0% |
| decreased appetite | 2 | 2.5% | 1 | 1.2% | 1 | 1.2% | 0 | 0.0% |
| Fever | 2 | 2.5% | 1 | 1.2% | 1 | 1.2% | 0 | 0.0% |
| Skin Rash | 2 | 2.5% | 2 | 2.5% | 0 | 0.0% | 0 | 0.0% |
| dizzyness | 2 | 2.5% | 2 | 2.5% | 0 | 0.0% | 0 | 0.0% |
| Loose stools | 2 | 2.5% | 2 | 2.5% | 0 | 0.0% | 0 | 0.0% |
| Urine Color Change | 2 | 2.5% | 2 | 2.5% | 0 | 0.0% | 0 | 0.0% |

To date, neither MTD nor RP2D has been reached. Doses through about 1000 mg/day of the compound exhibited favorable pharmacokinetics with apparent linear pharmacokinetics and no evidence of drug accumulation upon repeated daily dosing every 28 days. At the 320 mg/day dose level, the plasma concentration of the compound was sustained for over 8 hours at a concentration of at least 1.5 µM ($IC_{50}$ of the compound in vitro: 30-500 nM). The mean plasma concentrations of different dose groups were shown in FIG. 12.

Of the 42 patients dosed, 24 were evaluable for tumor response as of Feb. 7, 2011; 16 (16/24 evaluable patients) achieved stable disease (8 to 75+ weeks). The patients enrolled to date were summarized in Table 9.

TABLE 9

| | | | | | |
|---|---|---|---|---|---|
| Patient | Total Daily Dose (mg) | Schedule | Diagnosis | Best Response (RECIST 1.1) | New Lesions |
| 0001 | 20 | qd | Colon adenocarcinoma | MR (regression 27.6%) | 1 |
| 0002 | 40 | qd | Gastric adenocarcinoma | PD | 3 |
| 0003 | 80 | qd | Head and Neck carcinoma | SD | 0 |
| 0004 | 80 | bid | Colon adenocarcinoma | PD | 0 |
| 0005 | 160 | bid | Melanoma | n.e | n.e. |
| 0006 | 160 | bid | Lung adenocarcinoma | SD | 0 |
| 0007 | 320 | bid | Lung adenocarcinoma | n.e | n.e. |
| 0008 | 320 | bid | Colon adenocarcinoma | SD | 2 |
| 0009 | 320 | bid | Head and neck carcinoma | n.e | n.e. |
| 0010 | 320 | bid | Colon adenocarcinoma | SD | 0 |
| 0011 | 320 | bid | Angiosarcoma | SD | 0 |
| 0012 | 320 | bid | Prostate cancer | PD | 0 |
| 0013 | 400 | bid | Gastric adenocarcinoma | SD (signs of regression) | 0 |
| 0014 | 400 | bid | Ovarian cancer | SD (CA 125 normalization) | 0 |
| 0015 | 400 | bid | Colon adenocarcinoma | SD (CEA ? >30-50%) | 0 |
| 0016 | 600 | bid | Pancreatic adenocarcinoma | PD | 0 |
| 0017 | 600 | bid | Rectal cancer | n.e | n.e. |
| 0018 | 600 | bid | Prostate cancer | n.e | n.e. |
| 0019 | 600 | bid | NSC lung cancer | n.e | n.e. |
| 0020 | 600 | bid | Breast Cancer | SD (hollow tumor) | 0 |
| 0021 | 800 | bid | Chondrosarcoma | SD | 0 |
| 0022 | 800 | bid | Prostate cancer | PD | 0 |
| 0023 | 800 | bid | Adenocorticoid | SD | 0 |
| 0024 | 1000 | bid | Rectal cancer | SD | 0 |
| 0025 | 1000 | bid | Sarcoma | PD | — |
| 0026 | 1000 | bid | Pancreatic adenocarcinoma | n.e. | n.e. |
| 0027 | 1400 | bid | Colon adenocarcinoma | PD | 2 |
| 0028 | 1400 | bid | Colon adenocarcinoma | PD | — |
| 0029 | 1400 | bid | Melanoma | SD | — |
| 0030 | 1000 | bid | Colon adenocarcinoma | n.e | n.e. |
| 0031 | 1000 | bid | Colon adenocarcinoma | n.e | n.e. |
| 0032 | 200 | tid | Colon adenocarcinoma | SD | 0 |
| 0033 | 500 | tid | Colon adenocarcinoma | n.e | n.e. |
| 0034 | 500 | tid | Bladder adenocarcinoma | n.e | n.e. |
| 0035 | 500 | tid | Colorectal cancer | n.e | n.e. |

TABLE 9-continued

Patients Enrolled To Date

| Patient | Total Daily Dose (mg) | Schedule | Diagnosis | Best Response (RECIST 1.1) | New Lesions |
|---|---|---|---|---|---|
| 0036 | 500 | tid | Rectal cancer | n.e | n.e. |
| 0037 | 500 | tid | Colon adenocarcinoma | SD | 0 |
| 0038 | 500 | tid | Pancreatic cancer | n.e | n.e. |
| 0039 | 200 | tid | GEJ cancer | — | — |
| 0040 | 500 | bid | Colorectal cancer | — | — |
| 0041 | 500 | bid | Colorectal cancer | — | — |
| 0042 | 500 | bid | Colon adenocarcinoma | — | — |

16/24 evaluable patients show SD/MR with 12 showing prolonged SD (>12 weeks) by RECIST 1.1; New metastatic lesions were prevented in 83% of patients dosed.

Figure 19:
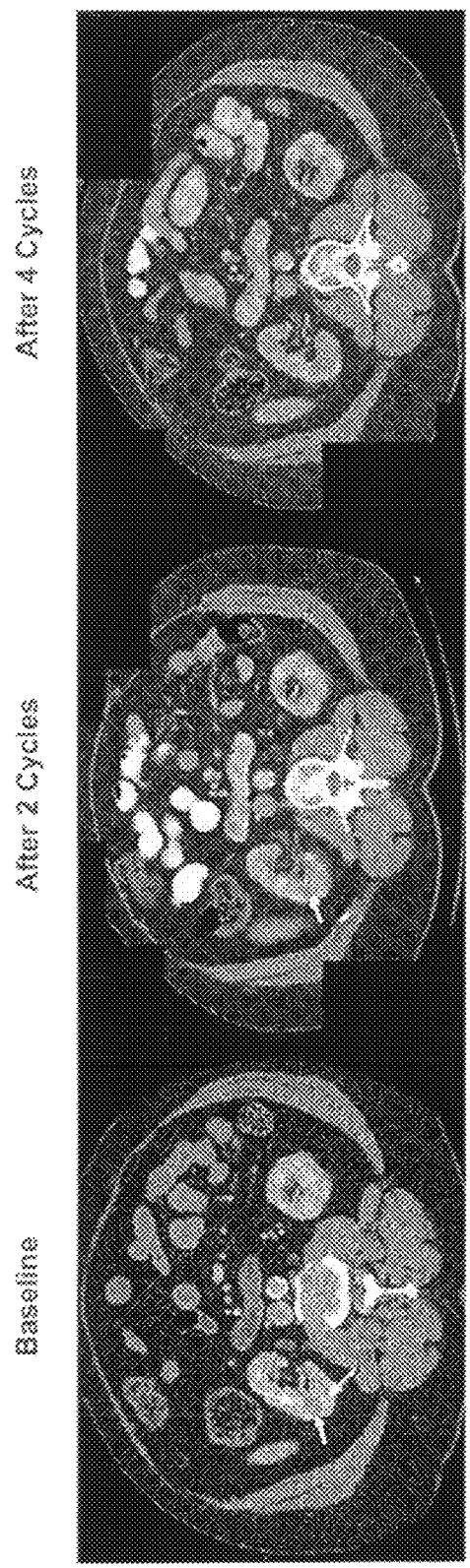
FIG. 19 is an illustration depicting a complete regression of a colon cancer metastatic lesion to kidney.

The complete regression of a colon cancer metastatic lesion to kidney in patient 0001 is shown in FIG. 19. In the 20 mg daily administration, a high concentration of the compound in urine of the patient was observed. The enrichment of the compound in urine (Table 10) explains the observed complete regression at relative low dosage.

The complete regression of a colon cancer metastatic lesion to kidney in patient 0001 is shown in FIG. 19. In the 20 mg daily administration, a high concentration of the compound in urine of the patient was observed. The enrichment of the compound in urine might help explain the observed complete regression at relative low dosage.

TABLE 10

Compound 1 is Present at High Concentration in Patient Urine

| Patient | Total Daily Dose (mg) | Time Post Dose (min) | BBI608 (uM) |
|---|---|---|---|
| 7 | 320 | 120-240 | 4.3 |
|   |     | 360-480 | 23.1 |
| 8 | 320 | 120-240 | 7.9 |
|   |     | 360-480 | 1.8 |
| 9 | 320 | 120-240 | 8.9 |
|   |     | 360-480 | 23.6 |
| 10 | 320 | 120-240 | 22.7 |
|    |     | 360-480 | 26.2 |
| 11 | 320 | 120-240 | 1.8 |
|    |     | 360-480 | 4.5 |
| 12 | 400 | 120-240 | 4.11 |
|    |     | 360-480 | 3.86 |
| 14 | 400 | 120-240 | 1.42 |
|    |     | 360-480 | 5 |
| 15 | 600 | 120-240 | 3.1 |
|    |     | 360-480 | 10.65 |
| 17 | 600 | 120-240 | 1.66 |
|    |     | 360-480 | 45.35 |
| 18 | 600 | 120-240 | 2.41 |
|    |     | 360-480 | 6.3 |
| 20 | 800 | 120-240 | 6.17 |
|    |     | 360-480 | 118.25 |
| 21 | 800 | 120-240 | 0.42 |
|    |     | 360-480 | 7.42 |
| 23 | 800 | 120-240 | 2.51 |
|    |     | 360-480 | 11.97 |

Accordingly, the compound showed an excellent safety profile. No dose limiting toxicity was observed to date.

A favorable PK profile with oral bid dosing was also observed. The plasma concentration reached several folds over efficacious concentration (in vitro $IC_{50}$). AUC data is shown in Table 11.

TABLE 11

AUC summary for different dose levels

| Total daily dose (mg) BID dosing | $AUC_{0-24}$ (uM * hr) | SD |
|---|---|---|
| 80 | 7.95 |  |
| 160 | 9.52 | 0.91 |
| 320 | 29.79 | 14.95 |
| 400 | 53.61 | 19.55 |
| 600 | 27.27 | 5.97 |
| 800 | 26.43 | 5.27 |
| 1000 | 42.61 | 8.94 |
| 1400 | 28.38 | 3.95 |
| 2000 | 39.09 | 18.66 |

Moreover, signs of anti-tumor activity were observed. 16 out of 24 patients showed SD/MR by RECIST in a range of tumors that are refractory to chemotherapies, including colorectal adenocarcinoma, head and neck cancer, lung cancer, breast cancer, gastric cancer, and ovarian cancer, melanoma. There was one complete regression of a colon cancer metastatic lesion to kidney (FIG. 19). Patients treated with Compound 1 exhibited a dramatic lack of new metastatic tumor lesions. Out of 24 evaluable patients with advanced refractory cancers, over 80% showed no metastatic tumors.

Figure 25:
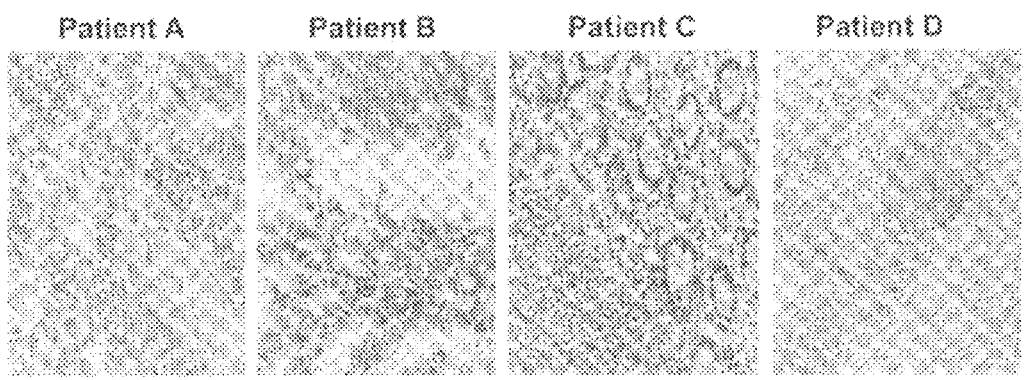
FIG. 25 is a photograph illustrating that patients achieved prolong stable disease (>16 weeks) during BBI608 treatment have high levels of p-STAT3 in their tumor tissues prior to the treatment.

The patients achieved prolong stable disease (>16 weeks) during BBI608 treatment were found to have high levels of p-STAT3 in their tumor tissues prior to the treatment by immunohistochemistry using anti-p-STAT3 antibody (FIG. 25).

Example 14: Dosing Regimens

The therapeutically effective amount of the pharmaceutical composition including particles, polymorphs and/or purified forms of a Compound of the Invention can be a total daily dose in the range of from about 20 mg to about 2000 mg, from about 240 mg to about 1500 mg, or from about 400 mg to about 1000 mg.

Suitable dosing regimens include administering particles, polymorphs and/or purified forms of a Compound of the Invention in a single daily dose. For example, the particles, polymorphs and/or purified forms of a Compound of the Invention are administered in a single daily dose in a range of from about 20 mg QD to about 1000 mg QD.

Suitable dosing regimens include administering particles, polymorphs and/or purified forms of a Compound of the Invention in more than one daily dose. For example, the particles, polymorphs and/or purified forms of a Compound of the Invention are administered in two daily doses, where the total daily dose is in a range of from about 40 mg to about 2000 mg. For example, the particles, polymorphs and/or purified forms of a Compound of the Invention are administered in two daily doses, where each dose is in a range of from about 20 mg to 1000 mg. For example, the particles, polymorphs and/or purified forms of a Compound of the Invention are administered in two daily doses, where each dose is in a range of from about 160 mg to 600 mg. For example, the particles, polymorphs and/or purified forms of a Compound of the Invention are administered in two daily doses, where each dose is in a range of from about 200 mg to 500 mg. For example, the particles, polymorphs and/or purified forms of a Compound of the Invention are administered in two daily doses, where each dose is about 500 mg.

Suitable dosing regimens include administering particles, polymorphs and/or purified forms of a Compound of the Invention in three daily doses, where the total daily dose is in a range of from about 60 mg to about 1500 mg. For example, the particles, polymorphs and/or purified forms of a Compound of the Invention are administered in three daily doses, where each dose is in a range of from about 20 mg to 500 mg. For example, the particles, polymorphs and/or purified forms of a Compound of the Invention are administered in three daily doses, where each dose is in a range of from 160 mg to 500 mg.

Figure 20:
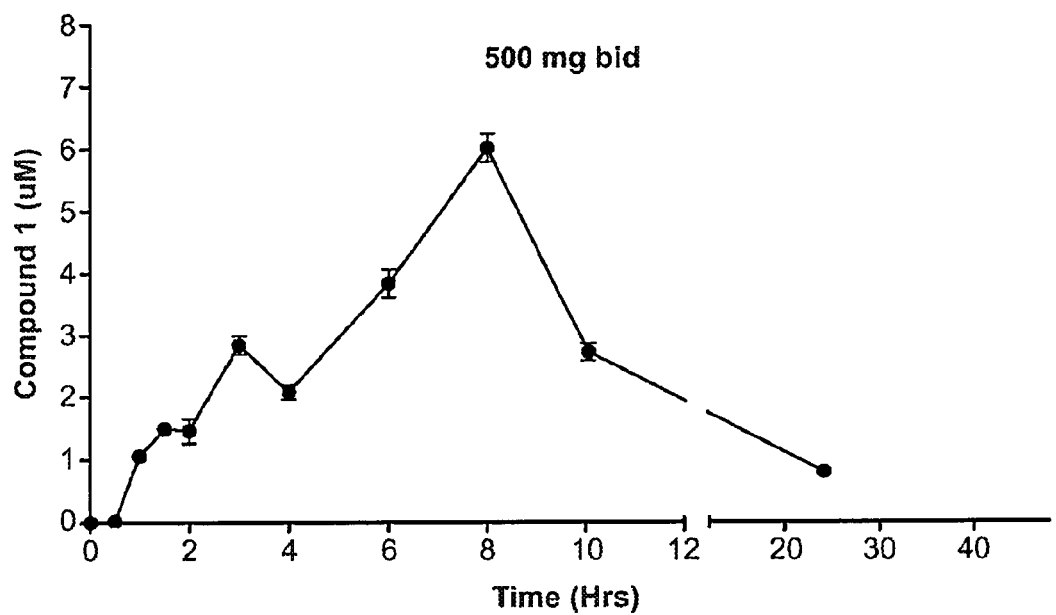
FIG. 20 is a graph that illustrates the pharmacokinetics of BID dosing in patients, where the patients were dosed at 500 mg twice daily (1000 mg total daily dose).

The dosing regimen in which human subjects received about 500 mg of Compound 1 twice daily (i.e., 1000 mg total daily dose) has shown achievement of best selective pharmacokinetics in almost all patients treated. This dosing regimen, which is referred to herein as 500 mg BID, has demonstrated the desired pharmacokinetic properties of Compound 1 in humans (FIG. 20).

In another suitable dosing regimen, 500 mg of Compound 1 are administered three times a day (TID) to human subjects. While the level of exposure of Compound 1 is not significantly improved by three times a day dosing as compared to twice daily dosing, the TID dosing does increase the exposure time of the drug in humans. This dose regimen, referred to herein as 500 mg TID, has shown good tolerability in humans with no significant drug related adverse events observed.

Figure 21:
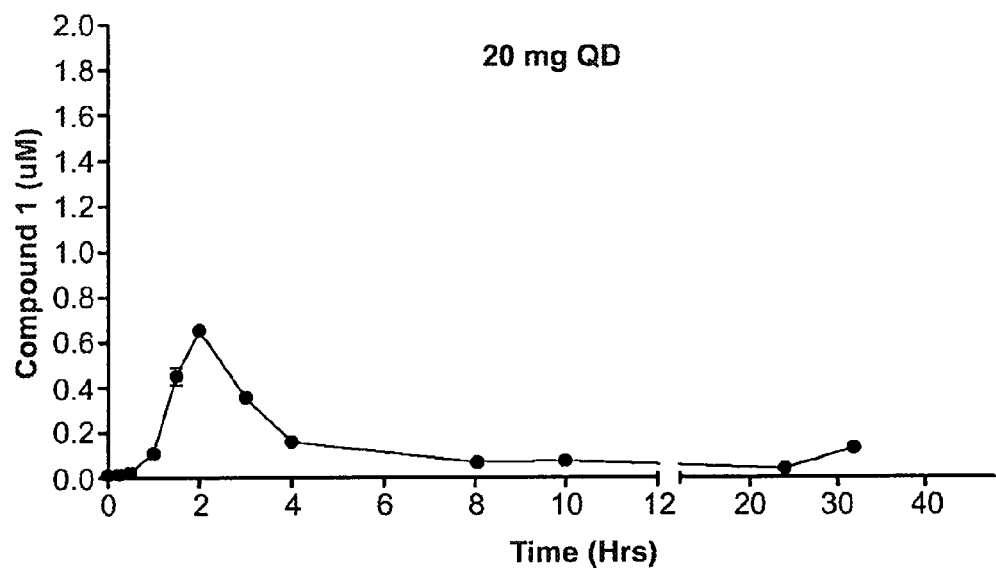
FIG. 21 is a graph that illustrates the pharmacokinetics of once daily dosing in patients, where the patients were dosed at 20 mg once daily.

In yet another suitable dosing regimen, at about or above 20 mg of Compound 1 is administered once daily to human subjects. This dosing regimen, referred to herein as 20 mg QD, has shown therapeutically active levels in patients, but is rapidly cleared from the blood in humans (FIG. 21). This dose regimen has shown good tolerability in humans and signs of potent antitumor activity in a colon cancer lesion in Kidney due to very high concentration of the drug in urine.

In yet another suitable dosing regimen, Compound 1 is administered with milk with empty stomach which gives desirable pharmacokinetics (Table 12).

TABLE 12

Effect of Milk on Compound 1 Pharmacokinetics

| PK Parameter | Fasting | with Milk | Fold Change |
|---|---|---|---|
| Cmax (uM) | 2.01 | 3.05 | 1.52 |
| $AUC_{0-24\,hrs}$ | 20.12 | 31.40 | 1.56 |
| Cmax (uM) | 2.55 | 2.89 | 1.13 |
| $AUC_{0-24\,hrs}$ | 20.72 | 32.16 | 1.55 |

In yet another suitable dosing regimen, Compound 1 is administered with food which delays the Tmax (Table 13).

TABLE 13

Taking Compound 1 with Food Causes a Delay in Tmax

| | Tmax (hr) | | |
|---|---|---|---|
| Patient | Fasting | With Milk | With Food |
| 20 | 2 | 2 | 8 |
| 21 | 6 | 6 | 6 |
| 22 | 8 | 8 | 10 |
| 24 | — | 6.3 | 10 |
| 27 | — | 0.5 | 6 |
| 28 | — | 6 | 10 |

Example 15: Naphthofuran Compounds Prolong Progression Free Survival

Figure 22:
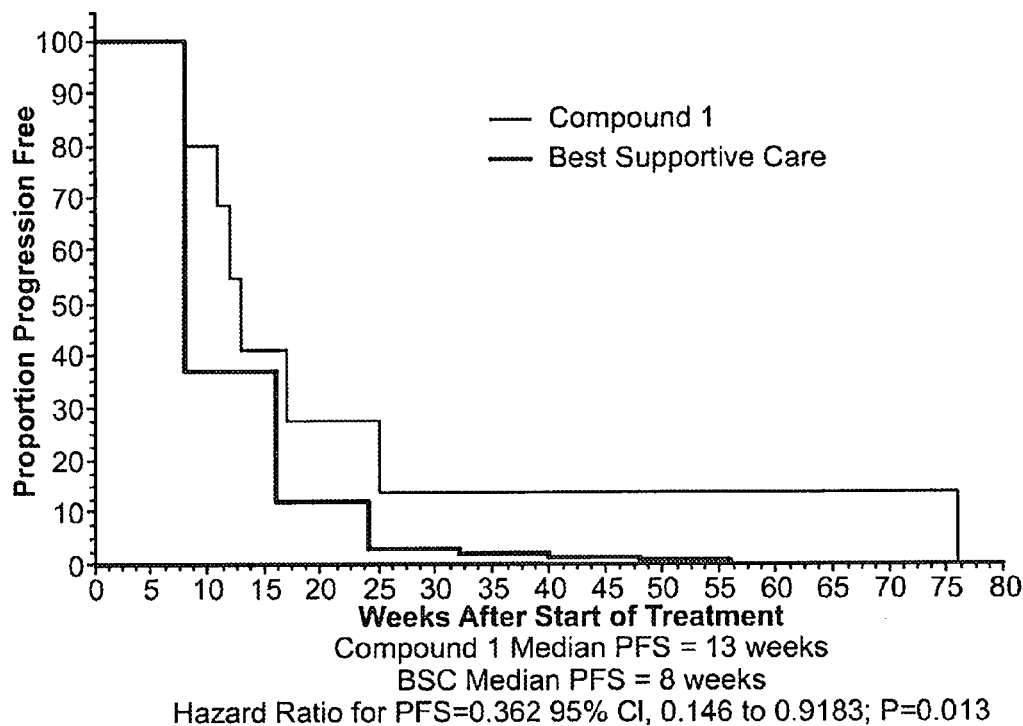
FIG. 22 is a graph that illustrates the comparison of progression free survival of colorectal cancer patients treated with Compound 1. The progression free survival (PFS) of evaluable patients with colorectal cancer treated with Compound 1 was compared against historical PFS data for best supportive care in patients with colorectal cancer.

Prolongation of progression free survival (PFS) has been shown in patients with advanced colorectal cancer which are refractory to chemotherapy (FIG. 22). Prolongation of progression free survival has also been seen in patients with head and neck cancer, gastric cancer, ovarian cancer, triple negative breast cancer, melanoma, adrenocorticoid cancer, and lung cancer.

Figure 23:
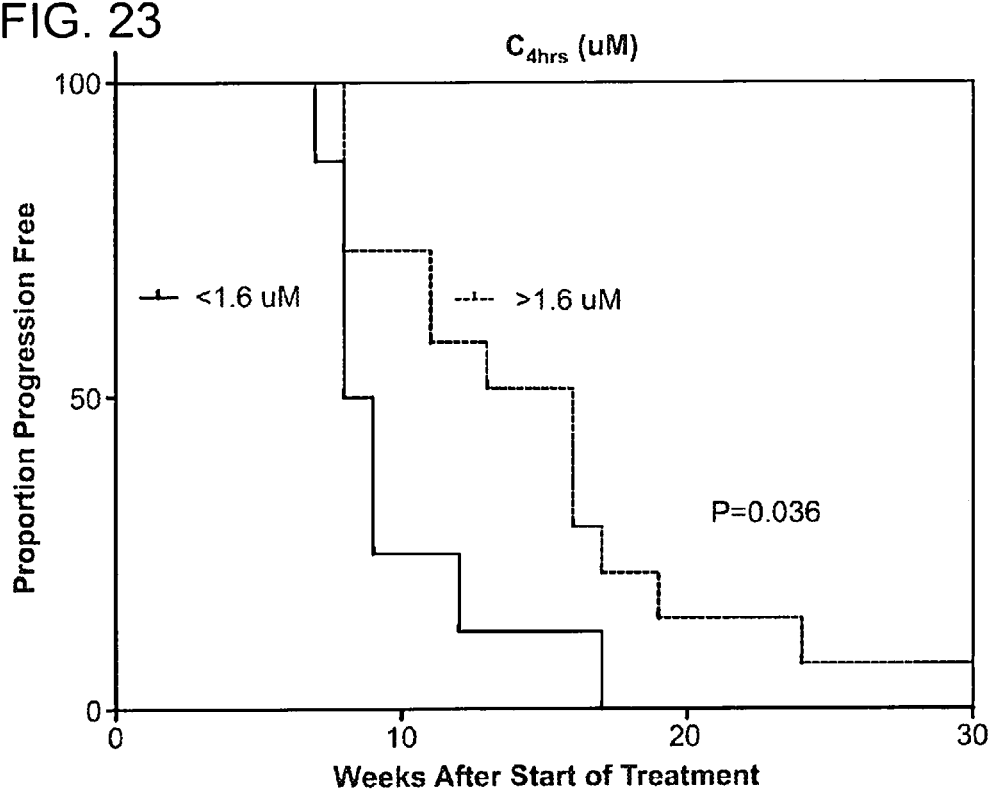
FIG. 23 is a graph that illustrates the comparison of progression free survival (PFS) versus pharmacokinetic exposure. The PFS of evaluable patients receiving Compound 1 was compared against Compound 1 exposure above or below 1.6 uM for at least 4 hours.

Blood drug concentration of Compound 1 above 1 uM correlated with an increase in progression free survival (FIG. 23) in patients with diverse cancers including colorectal, gastric, head and neck, melanoma, chondrosarcoma, lung, prostate, ovarian, adrenocorticoid and angiosarcoma.

Example 16: Pharmacokinetic Profile of Compound 1

Figure 24:
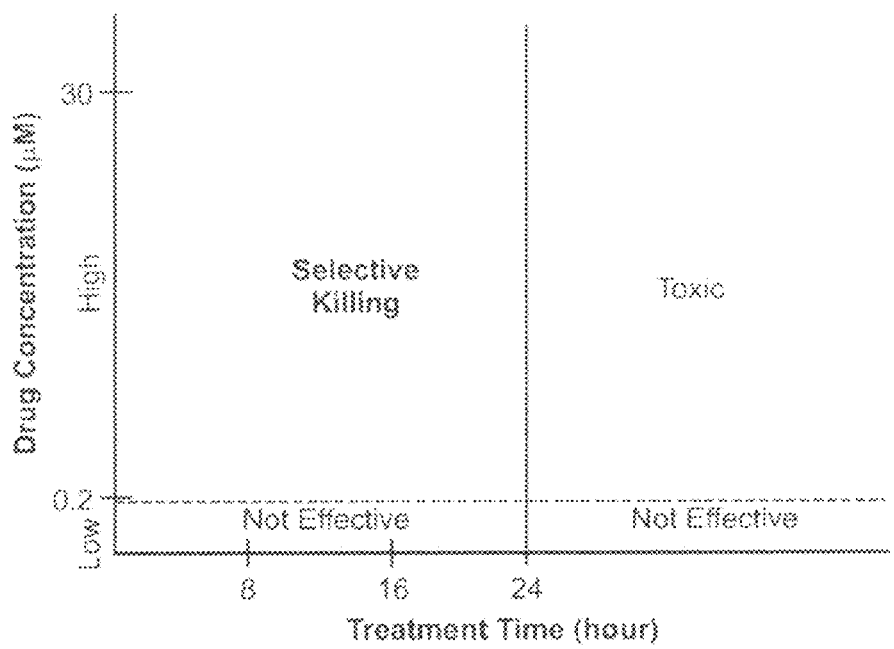
FIG. 24 is a graph that illustrates the desirable PK pattern for improved safety and efficacy.

Compound 1 was found to be equally toxic to cancer cells and normal cells, and was concluded to be no potential for treating cancer (K. Hirai K. et al., Cancer Detection and Prevention, 23(6) (1999) 539-550; Takano A. et al., Anti-cancer Research 29:455-464, 2009). The studies described herein discovered counter-intuitively that cancer cells and cancer stem cells requires much shorter exposure than normal cells to be killed by Compound 1. Normal cells can tolerate up to 24 hours of exposure to Compound 1. Furthermore, the studies here discovered that normal cells can recover after a short period of no-drug exposure, while cancer cells cannot recover once they are exposed to a certain concentration of the Compound 1 for at least 2 hours. Based on these studies, a special pharmacokinetic exposure [termed selective pharmacokinetic profile (SPP), or preferred pharmacokinetic profile (PPP), which is used interchangeably in this publication] was designed for Compound 1 using the data shown below in Table 14 for achieving selective antitumor activity in patients (FIG. 24).

TABLE 14

Use of particle size to achieve preferred pharmacokinetic (PK) exposure for increasing plasma drug concentration and reducing toxicity to normal cells

| | Compound 608 IC50 (uM) | | | | |
|---|---|---|---|---|---|
| | Normal Cells | | | | |
| Treatment Time | $CD34^+$ BM Erythroid | $CD34^+$ BM Myeloid | PMBCs | Cancer Cells | |
| | | | | DU145 | HT29 |
| 4-12 h | | | | <0.2 | <0.5 |
| 12-24 h | >30 | >30 | 14 | <0.2 | <0.5 |
| 72 h | | | 3 | | |

Suitable SPP or PPP exposure to a Compound of the Invention such as Compound 1, particles, polymorphs and/or purified forms thereof, is at least or above 1.0 µM for at least 2 hours, and blood drug concentration has to be cleared substantially within 24 hours.

For example, the patient maintains an exposure to a concentration of a Compound of the Invention such as Compound 1, particles, polymorphs and/or purified forms thereof of at least 1.5 µM for a defined period of time, preferably at least 2 hours and the drug has to be substantially cleared within 24 hours. Longer exposure to the compound can lead to toxicity and/or loss of selectivity.

To achieve this desired SPP or PPP, a Compound of the Invention can be administered in a dose to achieve a blood concentration in a subject, e.g., a patient, of compound in the range of from at least about 0.02 µM to about 30 µM. For example, a Compound of the Invention can be administered in a dose to achieve a blood concentration in a subject of compound at least about above 0.5 µM for a time of at least 2 hours, but less than 24 hours. For example, a Compound of the Invention can be administered in a dose to achieve a blood concentration in a subject of compound at least about 2 µM for a time of at least 2 hours, but less than 24 hours.

Preferably, cancer cells must be exposed to a Compound of the Invention such as Compound 1, particles, polymorphs and/or purified forms thereof for 4 hours at concentration greater than 0.2 µM in order to induce cancer cell death. However, prolonged exposure does not contribute significantly to the efficacy of a Compound of the Invention such as Compound 1, particles, polymorphs and/or purified forms thereof in killing cancer cells. Compound 1 exhibited selective activity in killing cancer cells and sparing normal cells when the concentration of Compound 1 was maintained at greater than from about 0.5 to about 3 µM for less than 24 hours. A reduced particle size of Compound 1 achieved this preferred pharmacokinetic pattern and selective activity.

The selective activity of Compound 1 in killing cancer cells and sparing normal cells is represented by the data in Table 14 and illustrated in FIG. 24. Exposure of cancer cells to Compound 1 at concentrations of about or above 0.2 and 30 µM for from about 4 hours up to about 24 hours showed selective killing of cancer cells and sparing of normal cells. Continuous exposure at these concentrations for durations of greater than 24 hours resulted in a loss of selectivity, in that normal cells were also damaged. Exposure to Compound 1 at blood concentrations of less than 0.5 µM resulted in no killing of cancer cells regardless of the amount of exposure time.

Figure 12:
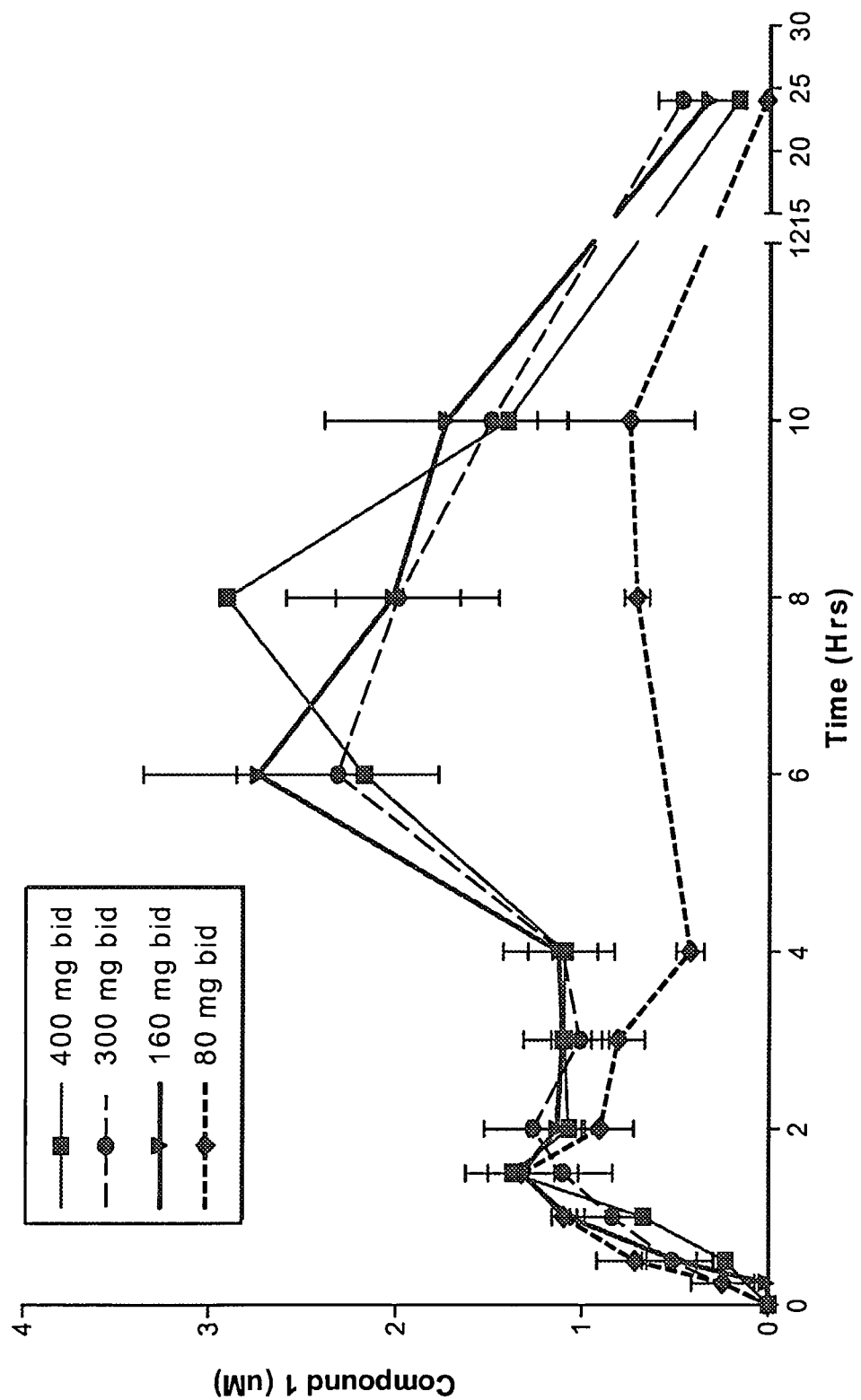
FIG. 12 is a graph depicting clinical PK data of Crystal Form 3 in cancer patients.

The dosing regimens described herein exhibit this preferred PK pattern. For example, the PK exhibited in patients receiving 500 mg BID in patients is this preferred PK exposure pattern (FIG. 20) which shows sustained exposure of Compound 1 above the therapeutic levels with substantial clearance of the drug by 24 hours. From 80 mg BID to 200 mg BID, SPP or PPP was achieved in patients with plasma drug concentration increase dose dependently. At 300 mg BID and 400 mg BID, it appeared plasma drug concentration appeared to have limited further increase over 200 mg BID. However, it was found that 500 mg BID can surprisingly help reduce inter-patient variation, namely all treated patients can achieve SPP with sufficiently high plasma drug concentration (FIG. 12). Finally, patients having exposure of Compound 1 above 1.6 uM for at least 4 hours show an improvement in progression free survival showing that this exposure pattern leads to improved efficacy in humans. PK exposure of Compound 1 above 1 uM correlates with an increase in progression free survival (FIG. 23) in patients with diverse cancers including colorectal, gastric, head and neck, melanoma, chondrosarcoma, lung, prostate, ovarian, adrenocorticoid and angiosarcoma. These data are very different than what one would expect from preclinical experiments. In preclinical studies, Compound showed to kill cancer cells or cancer stem cells with IC50 at about 100 to 200 nM. However, it was observed clinically in patients that those concentrations are not associated with clinical activity. In contrast, plasma concentration has to reach above 1 uM to have signs of activity. Further increase of plasma drug concentration to about or above 2 uM or 3 uM are associated with improved signs of antitumor activity.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for treating a cancer in a human subject comprising administering to a subject in need thereof a therapeutically effective amount of a compound having the structure

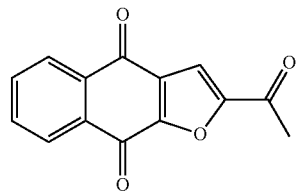 [SMILES: CC(=O)c1cc2c(o1)C(=O)c1ccccc1C2=O]

or a pharmaceutically acceptable salt or hydrate thereof,
wherein the compound is administered orally to the subject at a total daily dose in a range of from about 20 mg to about 1000 mg, and
the compound is in the form of crystalline particles, the particles having diameters of from about 0.002 µm to about 200 µm.

2. The method of claim 1, wherein the compound is administered to the subject at a total daily dose in a range of from about 400 mg to about 1000 mg.

3. The method of claim 1, wherein the compound is administered to the subject in a single daily dose in a range of from about 20 mg to about 1000 mg.

4. The method of claim 1, wherein the compound is administered to the subject in two daily doses.

5. The method of claim 4, wherein each dose is in a range of from about 200 mg to about 500 mg.

6. The method of claim 4, wherein each dose is about 500 mg.

7. The method of claim 1, wherein the compound is administered to the subject in three daily doses.

8. The method of claim 7, wherein each dose is in a range of from about 200 mg to about 500 mg.

9. The method of claim 1, wherein the compound is administered orally in conjunction with milk on an empty stomach.

10. The method of claim 1, wherein the particles have diameters of equal to or less than about 20 μm.

11. The method of claim 1, wherein the compound is in a pharmaceutical composition comprising a population of particles of the compound, and a fraction of the cumulative total of the particles have a diameter in the range of about 0.2 μm to about 20 μm.

12. The method of claim 1, wherein the compound is in a pharmaceutical composition comprising a population of particles of the compound, and 50% of the cumulative total of the particles ($D_{50}$) have a diameter of about 2 μm.

13. The method of claim 1, wherein the compound is administered in a purified composition having a purity greater than or equal to about 95.0%.

14. The method of claim 1, wherein the cancer is colorectal cancer, breast cancer, ovarian cancer, head and neck cancer, melanoma, angiosarcoma, gastric adenocarcinoma, pancreatic cancer, gastroesophageal junction (GEJ) cancer, gastric cancer, esophageal cancer, leukemia, lymphoma, multiple myeloma, brain tumor, hepatocellular carcinoma, lung cancer, prostate cancer, bile duct cancer, endometrial cancer, bladder cancer, renal cancer, or adrenocorticoid cancer.

15. The method of claim 1, wherein the cancer is colorectal cancer.

16. The method of claim 1, wherein the cancer is ovarian cancer.

17. The method of claim 1, wherein the cancer is breast cancer.

18. The method of claim 1, wherein the cancer is lung cancer.

19. The method of claim 1, wherein the cancer is refractory cancer.

20. The method of claim 1, wherein the cancer is recurrent cancer.

21. The method of claim 1, wherein the cancer is metastatic cancer.

22. The method of claim 1, wherein the cancer is associated with the expression of activated STAT3.

23. The method of claim 1, the method further comprising detecting a level of activated STAT3, where the level of activated STAT3 expression is used as a biomarker for patient selection.

24. The method of claim 1, wherein the cancer is gastroesophageal junction (GEJ) cancer.

25. The method of claim 1, wherein the cancer is hepatocellular carcinoma.

26. The method of claim 1, wherein the cancer is melanoma.

27. The method of claim 1, wherein the cancer is brain tumor.

28. The method of claim 1, wherein the cancer is leukemia, lymphoma, or multiple myeloma.

29. The method of claim 1, wherein the cancer is pancreatic cancer.

30. The method of claim 1, wherein the cancer is a sarcoma.

31. The method of claim 1, wherein the cancer is a carcinoma.

32. The method of claim 1, wherein the cancer is a hematological malignancy.

33. The method of claim 1 comprising administering one or more unit dosage forms of the compound.

34. The method of claim 33, wherein each unit dosage form comprises about 20 mg of the compound.

35. The method of claim 33, wherein each unit dosage form comprises about 40 mg of the compound.

36. The method of claim 33, wherein each unit dosage form comprises about 50 mg of the compound.

37. The method of claim 33, wherein each unit dosage form comprises about 80 mg of the compound.

* * * * *